United States Patent
Bassaganya-Riera et al.

(10) Patent No.: US 11,597,717 B2
(45) Date of Patent: *Mar. 7, 2023

(54) SUBSTITUTED IMIDAZOLES AS PLXDC2 LIGANDS

(71) Applicant: Landos Biopharma, Inc., Blacksburg, VA (US)

(72) Inventors: Josep Bassaganya-Riera, Blacksburg, VA (US); Andrew Leber, Blacksburg, VA (US); Raquel Hontecillas, Blacksburg, VA (US); Nuria Tubau-Juni, Blacksburg, VA (US)

(73) Assignee: Landos Biopharma, Inc., Blacksburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/488,984

(22) Filed: Sep. 29, 2021

(65) Prior Publication Data

US 2022/0017488 A1    Jan. 20, 2022

Related U.S. Application Data

(63) Continuation of application No. 17/212,425, filed on Mar. 25, 2021, now Pat. No. 11,180,473.

(60) Provisional application No. 63/081,011, filed on Sep. 21, 2020, provisional application No. 63/000,815, filed on Mar. 27, 2020.

(51) Int. Cl.
| | |
|---|---|
| *A61K 31/4164* | (2006.01) |
| *C07D 233/90* | (2006.01) |
| *C07D 401/12* | (2006.01) |
| *A61P 37/00* | (2006.01) |
| *A61P 19/02* | (2006.01) |
| *A61P 35/04* | (2006.01) |
| *C07D 405/12* | (2006.01) |

(52) U.S. Cl.
CPC ............ *C07D 401/12* (2013.01); *A61P 19/02* (2018.01); *A61P 35/04* (2018.01); *A61P 37/00* (2018.01); *C07D 405/12* (2013.01)

(58) Field of Classification Search
CPC .......................... A61K 31/4164; C07D 233/90
USPC ........................................ 514/400; 548/341.5
See application file for complete search history.

(56) References Cited

U.S. PATENT DOCUMENTS

| | | | |
|---|---|---|---|
| 4,820,757 A | 4/1989 | Spang et al. | |
| 4,994,478 A | 2/1991 | Kishimoto et al. | |
| 6,159,938 A | 12/2000 | Gyorkos et al. | |
| 6,201,016 B1 | 3/2001 | Cai et al. | |
| 7,598,274 B2 | 10/2009 | Finsinger et al. | |
| 8,143,285 B2 | 3/2012 | Kugimiya et al. | |
| 2004/0138269 A1 | 7/2004 | Sun et al. | |
| 2008/0090882 A1 | 4/2008 | Dorsch et al. | |
| 2009/0233972 A1 | 9/2009 | Or et al. | |
| 2010/0152045 A1 | 6/2010 | Lyga et al. | |
| 2010/0168138 A1 | 7/2010 | DeGoey et al. | |
| 2011/0070297 A1 | 3/2011 | Cao et al. | |
| 2011/0112073 A1 | 5/2011 | Thiele et al. | |
| 2011/0294853 A1 | 12/2011 | Pelcman et al. | |
| 2012/0110704 A1 | 5/2012 | Le Vezouet et al. | |
| 2012/0122681 A1 | 5/2012 | Le Vezouet et al. | |
| 2012/0208826 A1 | 8/2012 | Reddy et al. | |
| 2013/0012381 A1 | 1/2013 | Le Vezouet et al. | |
| 2013/0012382 A1 | 1/2013 | Le Vezouet et al. | |
| 2013/0072490 A1 | 3/2013 | Clark et al. | |
| 2013/0079326 A1 | 3/2013 | Tsui et al. | |
| 2014/0171348 A1 | 6/2014 | Patil et al. | |
| 2014/0235653 A1 | 8/2014 | Sandanayaka et al. | |
| 2014/0336185 A1 | 11/2014 | Boehm et al. | |
| 2016/0272657 A1 | 9/2016 | Ziegler et al. | |
| 2017/0001962 A1 | 1/2017 | Russo et al. | |
| 2017/0233405 A1 | 8/2017 | Koehler et al. | |
| 2018/0228923 A1 | 8/2018 | Lai et al. | |

(Continued)

FOREIGN PATENT DOCUMENTS

| | | |
|---|---|---|
| CN | 108516985 A | 9/2018 |
| CN | 111825661 A | 10/2020 |

(Continued)

OTHER PUBLICATIONS

International Search Report and Written Opinion. PCT/US2021/024122, dated May 17, 2021.

(Continued)

*Primary Examiner* — Douglas M Willis

(74) *Attorney, Agent, or Firm* — Daniel A. Blasiole; DeWitt LLP

(57) ABSTRACT

Provided are compounds of Formula Y-Z:

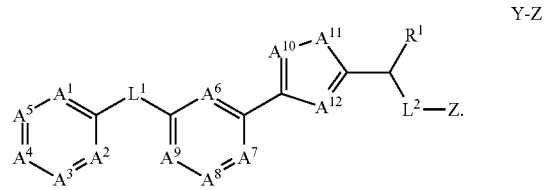

The compounds target plexin domain containing 2 (PLXDC2). The compounds can be used to treat conditions such as inflammatory or immune-mediated diseases, diabetes, infectious diseases, and cancers. The compounds can be used to treat such specific conditions as systemic lupus erythematosus, rheumatoid arthritis, multiple sclerosis, autoimmune encephalitis, diabetic nephropathy, diabetic retinopathy, psoriasis, and inflammatory bowel disease, among other conditions.

31 Claims, 23 Drawing Sheets

(56) References Cited

U.S. PATENT DOCUMENTS

| | | |
|---|---|---|
| 2019/0119250 A1 | 4/2019 | Willot et al. |
| 2020/0031816 A1 | 1/2020 | Min et al. |

FOREIGN PATENT DOCUMENTS

| | | | |
|---|---|---|---|
| EP | 3453706 A1 | 3/2019 | |
| EP | 3470404 A1 | 4/2019 | |
| JP | 01261381 A | 10/1989 | |
| JP | 2010241694 A | 10/2010 | |
| WO | WO-9507278 A1 * | 3/1995 | ............. A01N 43/54 |
| WO | WO 2001/017992 A1 | 3/2001 | |
| WO | WO 2005/000300 A1 | 1/2005 | |
| WO | WO 2005/049603 A1 | 6/2005 | |
| WO | WO 2006/024034 A1 | 3/2006 | |
| WO | WO 2006/074445 A2 | 7/2006 | |
| WO | WO 2007/016292 A2 | 2/2007 | |
| WO | WO 2007/024744 A2 | 3/2007 | |
| WO | WO 2008/064318 A2 | 5/2008 | |
| WO | WO 2009/011850 A2 | 1/2009 | |
| WO | WO 2009/156315 A1 | 12/2009 | |
| WO | WO 2010/108921 A1 | 9/2010 | |
| WO | WO 2011/117198 A2 | 9/2011 | |
| WO | WO 2011/117213 A1 | 9/2011 | |
| WO | WO 2012/035023 A1 | 3/2012 | |
| WO | WO 2012/064715 A1 | 5/2012 | |
| WO | WO 2012/139930 A1 | 10/2012 | |
| WO | WO 2013/131018 A1 | 9/2013 | |
| WO | WO 2015/173321 A1 | 11/2015 | |
| WO | WO 2017/011920 A1 | 1/2017 | |
| WO | WO 2018/187479 A1 | 10/2018 | |
| WO | WO 2018/215799 A1 | 11/2018 | |
| WO | WO 2020/092196 A1 | 5/2020 | |

OTHER PUBLICATIONS

Abreu, M.T., Toll-like receptor signalling in the intestinal epithelium: how bacterial recognition shapes intestinal function. *Nat Rev Immunol*, 2010. 10(2): p. 131-44.

Belkacemi, L. and S.X. Zhang, Anti-tumor effects of pigment epithelium-derived factor (PEDF): implication for cancer therapy. A mini-review. *J Exp Clin Cancer Res*, 2016. 35: p. 4.

CAS Registry No. 1818901-77-7, entered into the Registry File on Nov. 10, 2015.

Cheng, G., et al., Identification of PLXDC1 and PLXDC2 as the transmembrane receptors for the multifunctional factor PEDF. *Elife*, 2014. 3: p. e05401.

Dattatreya et al., A Brief Review on Immune Mediated Diseases. *J Clin Cell Immunol* 2011, S11. DOI: 10.4172/2155-9899.S11-001 ISSN:2155-9899 JCCI.

Dawson, D.W., et al., Pigment epithelium-derived factor: a potent inhibitor of angiogenesis. *Science*, 1999. 285(5425): p. 245-8.

Doll, J.A., et al., Pigment epithelium-derived factor regulates the vasculature and mass of the prostate and pancreas. *Nat Med*, 2003. 9(6): p. 774-80.

O'Connell, G.C., et al., Shifts in Leukocyte Counts Drive the Differential Expression of Transcriptional Stroke Biomarkers in Whole Blood. *Transl Stroke Res*, 2019. 10(1): p. 26-35.

Kondkar, Altaf A., et al. Plexin Domain Containing 2 (PLXDC2) gene Polymorphism rs7081455 may not influence POAG risk in a Saudi cohort,: BMC Res Notes (2018) 11:733.

Sanchez, A., et al., Pigment epithelium-derived factor (PEDF) protects cortical neurons in vitro from oxidant injury by activation of extracellular signal-regulated kinase (ERK) 1/2 and induction of Bcl-2. *Neurosci Res*, 2012. 72(1): p. 1-8.

Shurin MR, Smolkin YS. Immune-mediated diseases: where do we stand? *Adv Exp Med Biol*. 2007;601:3-12.

Wang, J.J., et al., Decreased expression of pigment epithelium-derived factor is involved in the pathogenesis of diabetic nephropathy. *Diabetes*, 2005. 54(1): p. 243-50.

Wang, J.J., et al., Anti-inflammatory effects of pigment epithelium-derived factor in diabetic nephropathy. *Am J Physiol Renal Physiol*, 2008. 294(5): p. F1166-73.

Yoshida, Y., et al., Protective role of pigment epithelium-derived factor (PEDF) in early phase of experimental diabetic retinopathy. Diabetes *Metab Res Rev*, 2009. 25(7): p. 678-86.

Zamiri, P., et al., Pigment epithelial growth factor suppresses inflammation by modulating macrophage activation. *Invest Ophthalmol Vis Sci*, 2006. 47(9): p. 3912-8.

Zhang, S.X., et al., Pigment epithelium-derived factor (PEDF) is an endogenous anti inflammatory factor. *FASEB J*, 2006. 20(2): p. 323-5.

U.S. Appl. No. 17/212,425, filed Mar. 25, 2021, Josep Bassaganya-Riera.

* cited by examiner

| Identifier | Structure | Affinity |
|---|---|---|
| PX-02 | 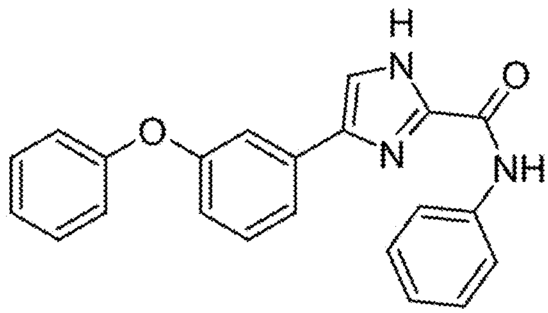 | -10.4 |
| PX-03 | 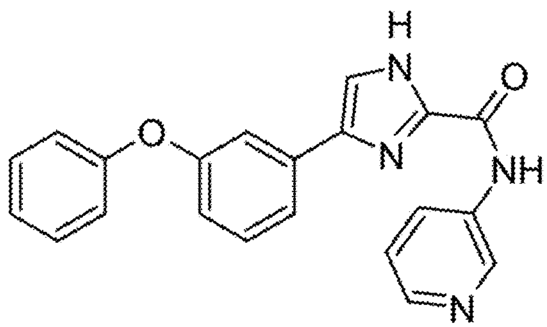 | -10.5 |
| PX-04 | 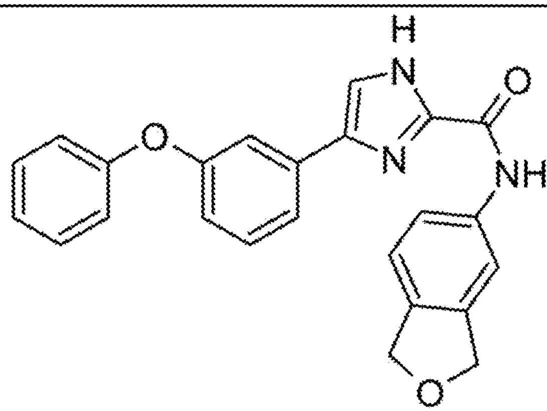 | -11.8 |
| PX-05 | 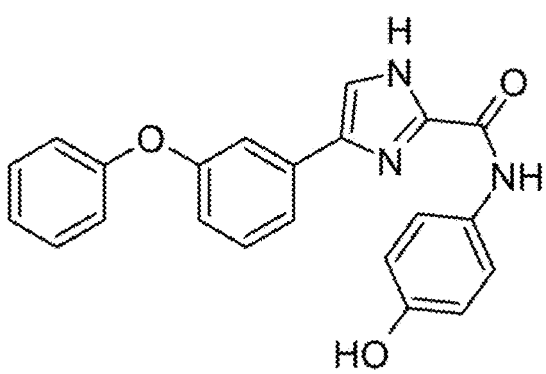 | -11.0 |

| Identifier | Structure | Affinity |
|---|---|---|
| PX-06 | 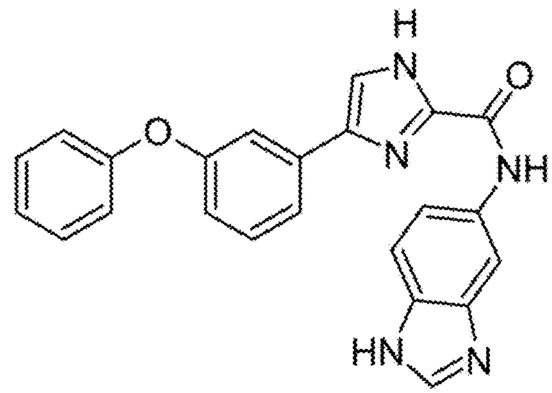 | -11.2 |
| PX-07 | 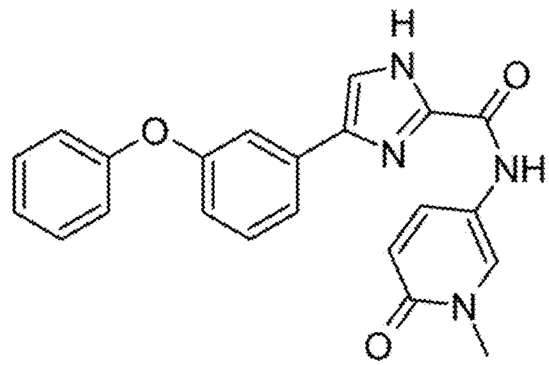 | -11.9 |
| PX-08 | 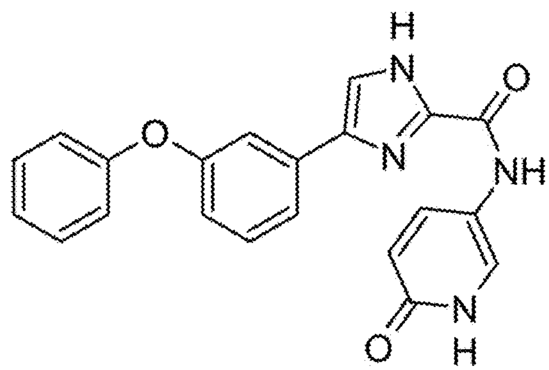 | -11.4 |
| PX-09 | 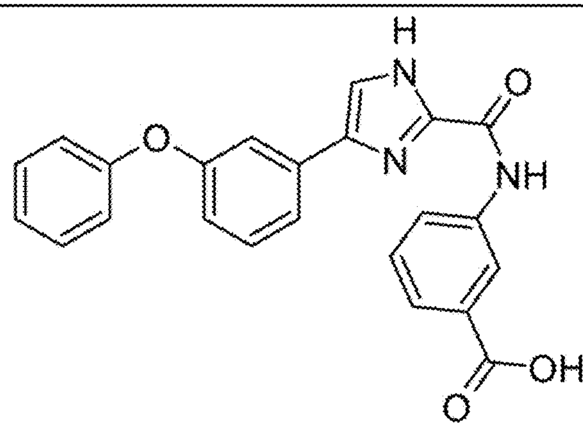 | -11.7 |

| Identifier | Structure | Affinity |
|---|---|---|
| PX-10 | 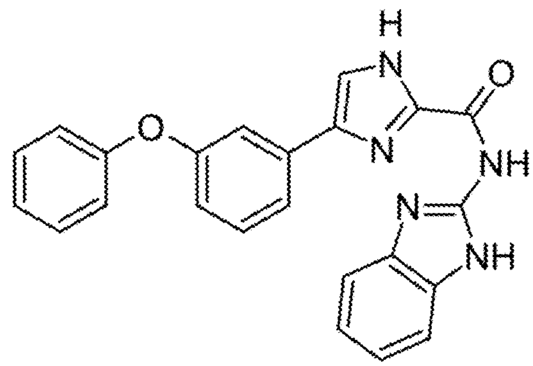 | -11.2 |
| PX-11 | 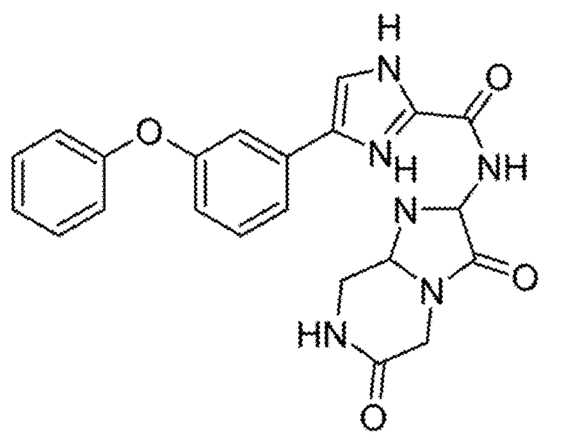 | -12.6 |
| PX-12 | 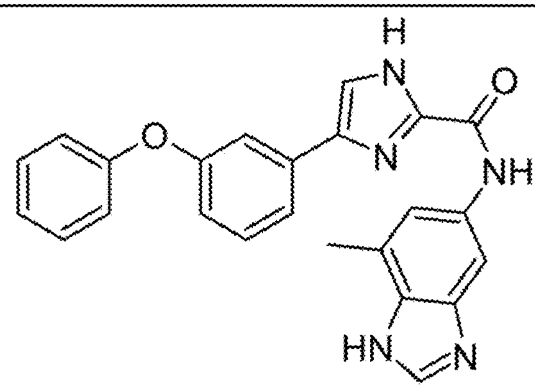 | -11.5 |
| PX-13 | 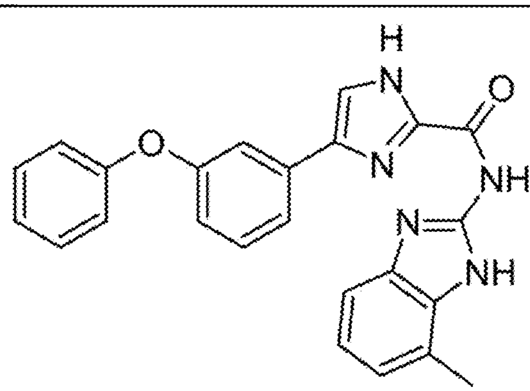 | -11.4 |

| Identifier | Structure | Affinity |
|---|---|---|
| PX-14 | 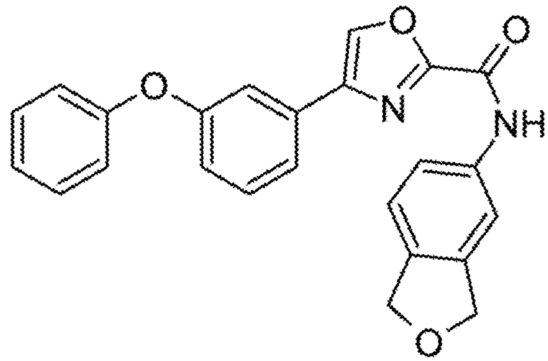 | -11.5 |
| PX-15 | 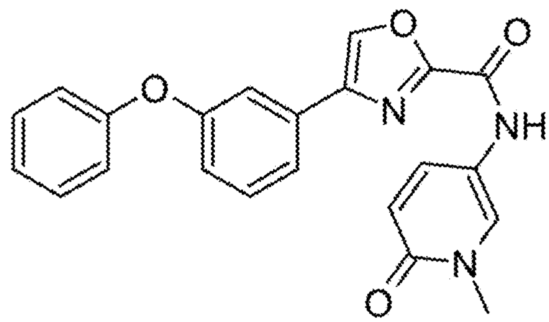 | -11.5 |
| PX-16 | 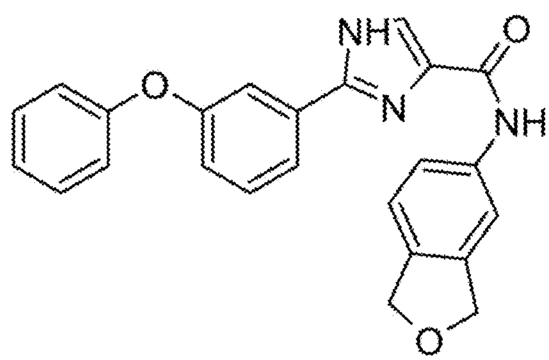 | -11.7 |
| PX-17 | 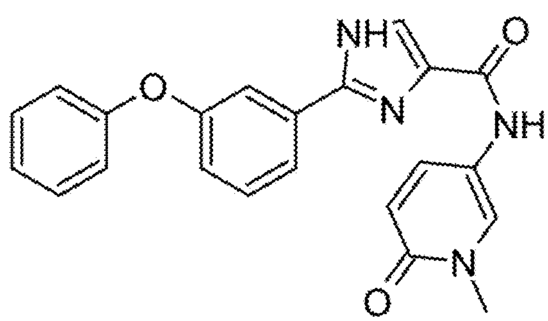 | -11.9 |

| Identifier | Structure | Affinity |
|---|---|---|
| PX-18 | 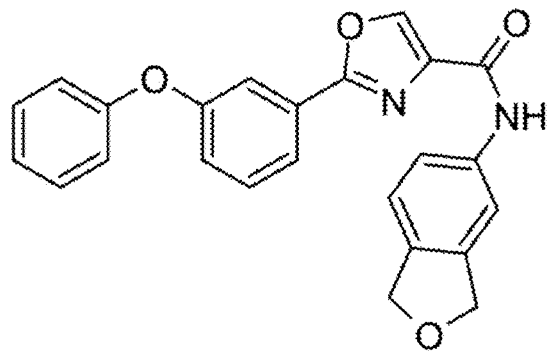 | -11.2 |
| PX-19 | 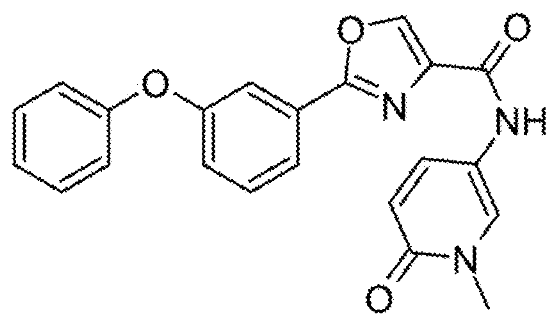 | -11.0 |
| PX-20 | 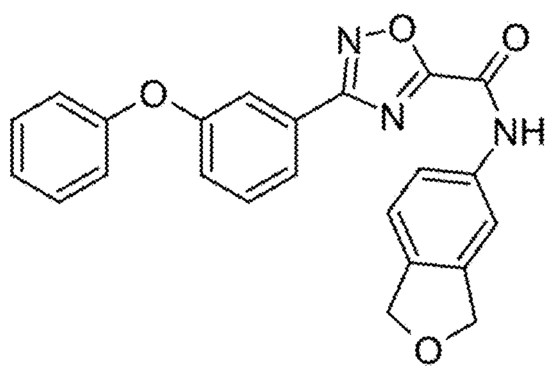 | -12.0 |
| PX-21 | 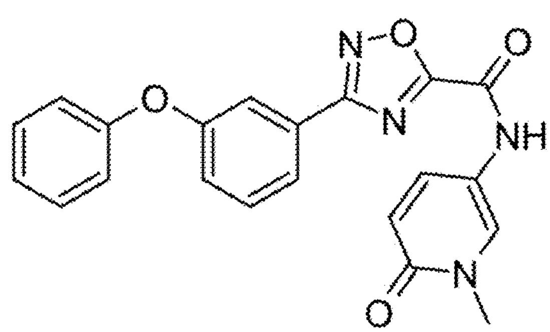 | -11.9 |

| Identifier | Structure | Affinity |
|---|---|---|
| PX-22 | 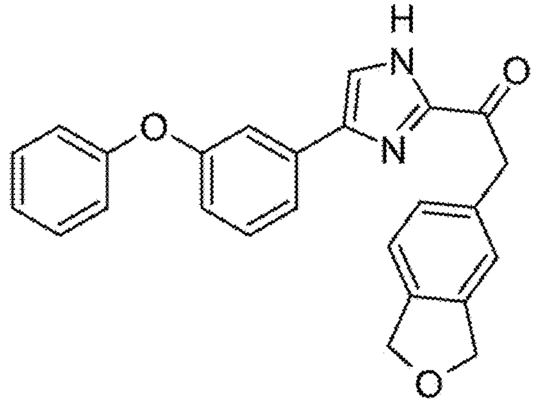 | -11.8 |
| PX-23 | 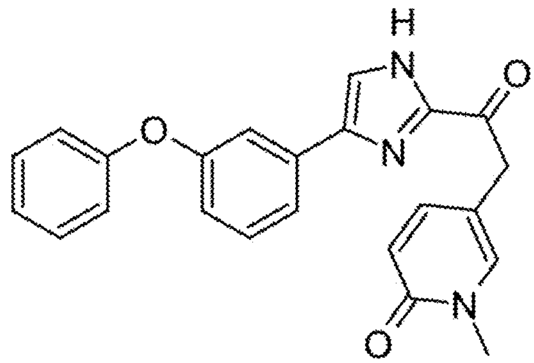 | -11.6 |
| PX-24 | 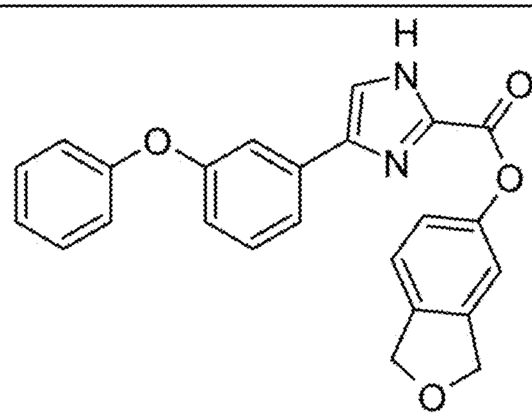 | -11.9 |
| PX-25 | 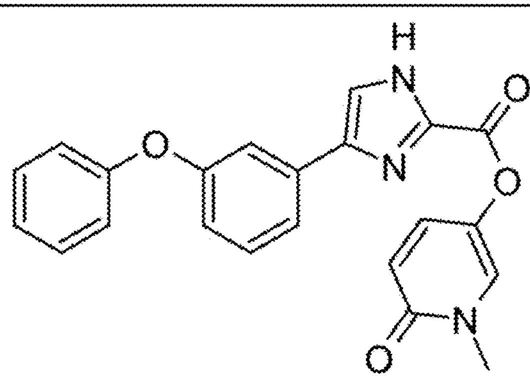 | -12.1 |

FIG. 1F

| Identifier | Structure | Affinity |
|---|---|---|
| PX-26 | 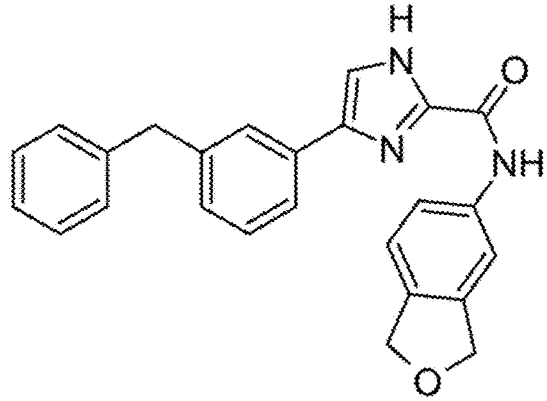 | -11.3 |
| PX-27 | 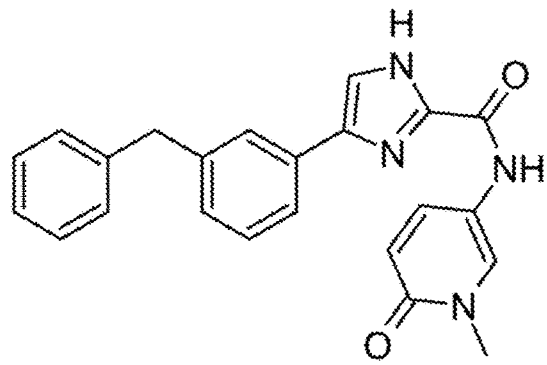 | -11.4 |
| PX-28 | 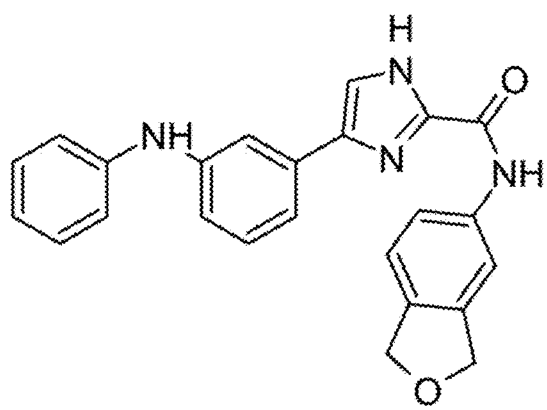 | -10.9 |
| PX-29 | 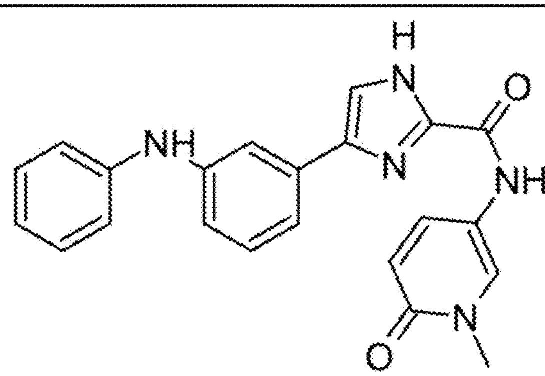 | -11.5 |

| Identifier | Structure | Affinity |
|---|---|---|
| PX-30 | 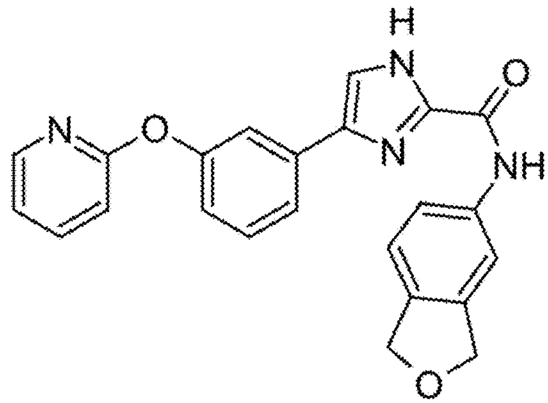 | -11.7 |
| PX-31 | 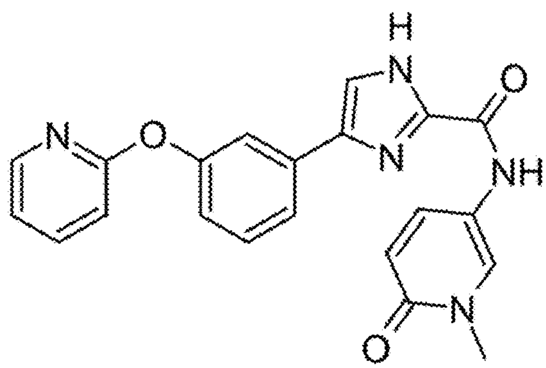 | -11.8 |
| PX-32 | 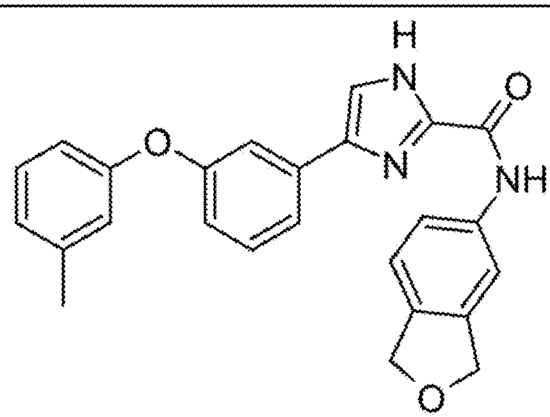 | -12.1 |
| PX-33 | 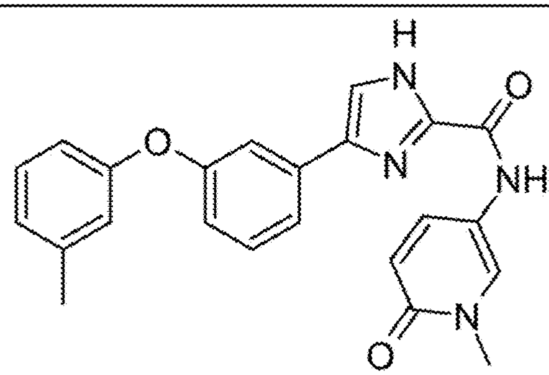 | -12.1 |

FIG. 1H

| Identifier | Structure | Affinity |
|---|---|---|
| PX-34 | 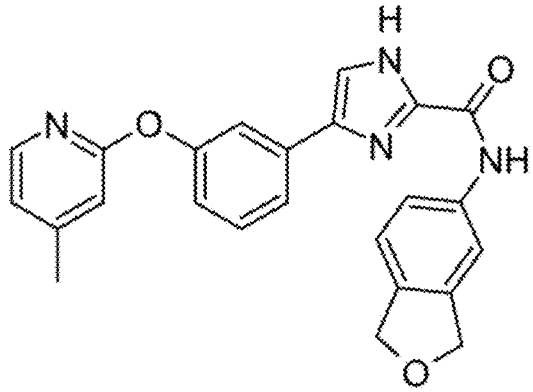 | -12.1 |
| PX-35 | 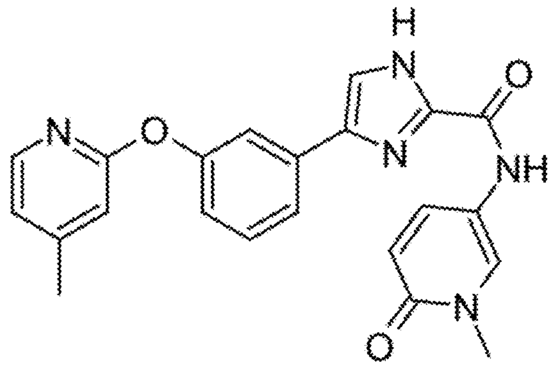 | -12.0 |
| PX-36 | 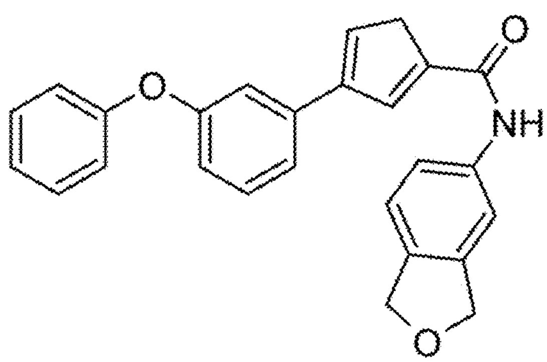 | -11.1 |
| PX-37 | 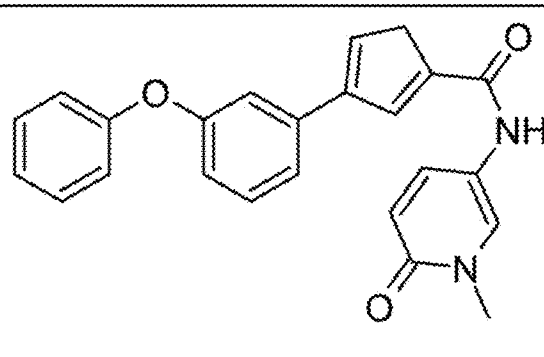 | -11.4 |

SUBSTITUTED IMIDAZOLES AS PLXDC2 LIGANDS

FIELD OF THE INVENTION

The invention is directed to compounds that target plexin domain containing 2 (PLXDC2). The invention is also directed to use of the compounds in the treatment of inflammatory or immune-mediated diseases, diabetes, and other conditions, including such conditions as systemic lupus erythematosus, rheumatoid arthritis, multiple sclerosis, autoimmune encephalitis, diabetic nephropathy and diabetic retinopathy, non-alcoholic fatty liver disease, non-alcoholic steatohepatitis, cirrhosis, asthma, allergy, psoriasis, and inflammatory bowel disease, among other conditions.

BACKGROUND

Plexin domain containing 2 (PLXDC2) is a transmembrane protein recently identified as a receptor of pigment epithelial-derived factor (PEDF) (Cheng et al. 2014), an anti-angiogenic, anti-tumoral and neuroprotective protein (Belkacemi et al. 2016, Dawson et al. 1999, Doll et al. 2003, Sanchez et al. 2012), also associated with the induction of anti-inflammatory mechanisms in immune and non-immune cells (Zhang et al. 2006, Wang et al. 2008, Zamiri et al. 2006). Loss of Plxdc2, through silencing or genetic knockout, results in a phenotypic shift in macrophages, supported by the downregulated expression of M2-associated genes, such as Retnla and Arg1, and increased secretion of pro-inflammatory cytokines, such as IL-6 and TNFα. PLXDC2 is expressed in high amounts in neutrophils and monocytes within human blood (O'Connell et al. 2019). While differentially expressed in myeloid cells, loss of PLXDC2 also results in greater T helper 17 (Th17) differentiation in vitro and lesser regulatory CD4+ T cells (Treg) in murine models in vivo. In models of *Helicobacter pylori* infection and DSS colitis, mice lacking PLXDC2 develop greater inflammation as measured through histopathology, gene expression and flow cytometry identification of neutrophils and inflammatory macrophages. Meanwhile, decreased PEDF results in oxidative stress in relation to diabetic conditions, such as diabetic retinopathy (Yoshida et al. 2009) and diabetic nephropathy (Wang et al. 2005). Thus, PLXDC2 activation may help to treat overall disease and complications from autoimmune and infectious diseases and other conditions.

There are clear unmet clinical needs for safer, more effective treatments for diseases in which PLXDC2 is implicated. These include autoimmune diseases, such as systemic lupus erythematosus, rheumatoid arthritis, multiple sclerosis, and type 1 diabetes, type 2 diabetes, chronic and inflammatory cardiovascular diseases, cancers, and infectious diseases. Due to low efficacy and poor safety, current autoimmune treatments require frequent monitoring, shifting treatment paradigms, and complex delivery methods. Thus, new treatments capable of being dosed orally for long-term management of disease are needed. In infectious diseases, high mutation rates in various microbes necessitate the development of novel non-antimicrobial treatments that spare the use of antibacterials, antifungals, and antivirals. Further, new strains and epidemic infections create a lag period between the emergence of a pathogen and the availability of microbe-specific interventions, creating a need for novel host-targeted therapeutics. There is therefore a need to develop ligands of the PLXDC2 pathway.

The present invention provides new compounds that bind to PLXDC2 and induce a beneficial response in various disease conditions. These disease conditions include but are not limited to inflammatory, immune-mediated, or chronic diseases, cancers, and infectious diseases of bacterial, fungal and viral origin generally, and such specific conditions as systemic lupus erythematosus, rheumatoid arthritis, multiple sclerosis, autoimmune encephalitis, diabetic nephropathy, diabetic retinopathy, psoriasis, and inflammatory bowel disease, non-alcoholic fatty liver disease, non-alcoholic steatohepatitis, cirrhosis, asthma, and allergy.

SUMMARY OF THE INVENTION

The invention provides compounds of Formula Y-Z, or a salt or ester thereof, wherein:
Y is:

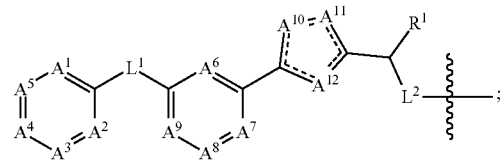

Z is $Z^1$ or $Z^2$;
$Z^1$ is:

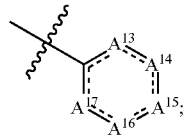

$Z^2$ is:

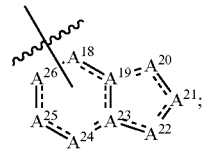

$A^1$, $A^2$, $A^3$, $A^4$, $A^5$, $A^6$, $A^7$, $A^8$, and $A^9$, are each independently $C(R^2)$ or N;

$A^{10}$, $A^{11}$, $A^{12}$, $A^{13}$, $A^{14}$, $A^{15}$, $A^{16}$, $A^{17}$, $A^{18}$, $A^{20}$, $A^{21}$, $A^{22}$, $A^{24}$, $A^{25}$, and $A^{26}$ are each independently O, $N(R^2)$, $C(R^2)_2$, $C(R^2)$, or N, with the proviso that at least one of $A^{18}$, $A^{20}$, $A^{21}$, $A^{22}$, $A^{24}$, $A^{25}$, and $A^{26}$ is $N(R^2)$, $C(R^2)_2$, or $C(R^2)$;

$A^{19}$ and $A^{23}$ are each independently $C(R^2)$, N, or C;

each --- between adjacent atoms represents a bond that is present or absent;

$L^1$ and $L^2$ are each independently O, $N(R^2)$, or $C(R^2)_2$;

$R^1$ is oxo, $N(R^2)_2$, methyl, ethyl, hydroxyl, unsubstituted C1-C2 alkyloxy, or halogen; and $R^2$ in each instance is independently hydrogen, halogen, oxo, optionally substituted alkyl, optionally substituted alkenyl, optionally substituted alkynyl, optionally substituted cycloalkyl, optionally substituted cycloalkenyl, hydroxyl, carboxyl, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkyl sulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted aryl sulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group, with the proviso that an $R^2$ of one of $A^{18}$, $A^{20}$, $A^{21}$, $A^{22}$, $A^{24}$, $A^{25}$ and $A^{26}$ is Y.

In some versions, $A^1$ is $C(R^2)$. In some versions, $A^1$ is N. In some versions, $A^2$ is $C(R^2)$. In some versions, $A^2$ is N. In some versions, $A^3$ is $C(R^2)$. In some versions, $A^3$ is N. In some versions, $A^4$ is $C(R^2)$. In some versions, $A^4$ is N. In some versions, $A^5$ is $C(R^2)$. In some versions, $A^5$ is N. In some versions, $A^6$ is $C(R^2)$. In some versions, $A^6$ is N. In some versions, $A^7$ is $C(R^2)$. In some versions, $A^7$ is N. In some versions, $A^8$ is $C(R^2)$. In some versions, $A^8$ is N. In some versions, $A^9$ is $C(R^2)$. In some versions, $A^9$ is N.

In some versions, $A^{10}$ is O. In some versions, $A^{10}$ is $N(R^2)$. In some versions, $A^{10}$ is $C(R^2)_2$. In some versions, $A^{10}$ is $C(R^2)$. In some versions, $A^{10}$ is N. In some versions, $A^{11}$ is O. In some versions, $A^{11}$ is $N(R^2)$. In some versions, $A^{11}$ is $C(R^2)_2$. In some versions, $A^{11}$ is $C(R^2)$. In some versions, $A^{11}$ is N. In some versions $A^{12}$ is O. In some versions $A^{11}$ is $N(R^2)$. In some versions $A^{12}$ is $C(R^2)_2$. In some versions $A^{12}$ is $C(R^2)$. In some versions $A^{12}$ is N. In some versions $A^{13}$ is O. In some versions $A^{13}$ is $N(R^2)$. In some versions $A^{13}$ is $C(R^2)_2$. In some versions $A^{11}$ is $C(R^2)$. In some versions $A^{11}$ is N. In some versions $A^{14}$ is O. In some versions $A^{14}$ is $N(R^2)$. In some versions $A^{14}$ is $C(R^2)_2$. In some versions $A^{14}$ is $C(R^2)$. In some versions $A^{14}$ is N. In some versions $A^{15}$ is O. In some versions $A^{15}$ is $N(R^2)$. In some versions $A^{15}$ is $C(R^2)_2$. In some versions $A^{15}$ is $C(R^2)$. In some versions $A^{15}$ is N. In some versions $A^{16}$ is O. In some versions $A^{16}$ is $N(R^2)$. In some versions $A^{16}$ is $C(R^2)_2$. In some versions $A^{16}$ is $C(R^2)$. In some versions $A^{16}$ is N. In some versions $A^{17}$ is O. In some versions $A^{17}$ is $N(R^2)$. In some versions $A^{17}$ is $C(R^2)_2$. In some versions $A^{17}$ is $C(R^2)$. In some versions $A^{17}$ is N. In some versions $A^{18}$ is O. In some versions $A^{18}$ is $N(R^2)$. In some versions $A^{18}$ is $C(R^2)_2$. In some versions $A^{18}$ is $C(R^2)$. In some versions $A^{18}$ is N. In some versions $A^{20}$ is O. In some versions $A^{20}$ is $N(R^2)$. In some versions $A^{20}$ is $C(R^2)_2$. In some versions $A^{20}$ is $C(R^2)$. In some versions $A^{20}$ is N. In some versions $A^{21}$ is O. In some versions $A^{21}$ is $N(R^2)$. In some versions $A^{21}$ is $C(R^2)_2$. In some versions $A^{21}$ is $C(R^2)$. In some versions $A^{21}$ is N. In some versions $A^{22}$ is O. In some versions $A^{22}$ is $N(R^2)$. In some versions $A^{22}$ is $C(R^2)_2$. In some versions $A^{22}$ is $C(R^2)$. In some versions $A^{22}$ is N. In some versions $A^{24}$ is O. In some versions $A^{24}$ is $N(R^2)$. In some versions $A^{24}$ is $C(R^2)_2$. In some versions $A^{24}$ is $C(R^2)$. In some versions $A^{24}$ is N. In some versions $A^{25}$ is O. In some versions $A^{25}$ is $N(R^2)$. In some versions $A^{25}$ is $C(R^2)_2$. In some versions $A^{25}$ is $C(R^2)$. In some versions $A^{25}$ is N. In some versions $A^{26}$ is O. In some versions $A^{26}$ is $N(R^2)$. In some versions $A^{26}$ is $C(R^2)_2$. In some versions $A^{26}$ is $C(R^2)$. In some versions $A^{26}$ is N. In some versions, $A^{19}$ is $C(R^2)$. In some versions, $A^{19}$ is N. In some versions, $A^{19}$ is C. In some versions, $A^{23}$ is $C(R^2)$. In some versions, $A^{23}$ is N. In some versions, $A^{23}$ is C.

In some versions, the --- between $A^{10}$ and $A^{11}$ is a bond that is present. In some versions, the --- between $A^{10}$ and $A^{11}$ is absent. In some versions, the --- between $A^{11}$ and the carbon directly between $A^{10}$ and $A^{11}$ is a bond that is present. In some versions, the --- between $A^{11}$ and the carbon directly between $A^{11}$ and $A^{12}$ is absent. In some versions, the --- between $A^{12}$ and the carbon directly between $A^{11}$ and $A^{12}$ is a bond that is present. In some versions, the --- between $A^{12}$ and the carbon directly between $A^{11}$ and $A^{12}$ is absent. In some versions, the --- between $A^{12}$ and the carbon directly between $A^{12}$ and $A^{10}$ is a bond that is present. In some versions, the --- between $A^{12}$ and the carbon directly between $A^{12}$ and $A^{10}$ is absent. In some versions, the --- between $A^{10}$ and the carbon directly between $A^{12}$ and $A^{10}$ is a bond that is present. In some versions, the --- between $A^{10}$ and the carbon directly between $A^{12}$ and $A^{10}$ is absent. In some versions, the --- between $A^{13}$ and $A^{14}$ is a bond that is present. In some versions, the --- between $A^{13}$ and $A^{14}$ is absent. In some versions, the --- between $A^{14}$ and $A^{15}$ is a bond that is present. In some versions, the --- between $A^{14}$ and $A^{15}$ is absent. In some versions, the --- between $A^{15}$ and $A^{16}$ is a bond that is present. In some versions, the --- between $A^{15}$ and $A^{16}$ is absent. In some versions, the --- between $A^{16}$ and $A^{17}$ is a bond that is present. In some versions, the --- between $A^{16}$ and $A^{17}$ is absent. In some versions, the --- between $A^{17}$ and the carbon directly between $A^{17}$ and $A^{13}$ is a bond that is present. In some versions, the --- between $A^{17}$ and the carbon directly between $A^{17}$ and $A^{11}$ is absent. In some versions, the --- between $A^{18}$ and $A^{19}$ is a bond that is present. In some versions, the --- between $A^{18}$ and $A^{19}$ is absent. In some versions, the --- between $A^{19}$ and $A^{20}$ is a bond that is present. In some versions, the --- between $A^{19}$ and $A^{20}$ is absent. In some versions, the --- between $A^{20}$ and $A^{21}$ is a bond that is present. In some versions, the --- between $A^{20}$ and $A^{21}$ is absent. In some versions, the --- between $A^{21}$ and $A^{22}$ is a bond that is present. In some versions, the --- between $A^{21}$ and $A^{22}$ is absent. In some versions, the --- between $A^{22}$ and $A^{23}$ is a bond that is present. In some versions, the --- between $A^{22}$ and $A^{23}$ is absent. In some versions, the --- between $A^{23}$ and $A^{24}$ is a bond that is present. In some versions, the --- between $A^{23}$ and $A^{24}$ is absent. In some versions, the --- between $A^{24}$ and $A^{25}$ is a bond that is present. In some versions, the --- between $A^{24}$ and $A^{25}$ is absent. In some versions, the --- between $A^{25}$ and $A^{26}$ is a bond that is present. In some versions, the --- between $A^{25}$ and $A^{26}$ is absent. In some versions, the --- between $A^{26}$ and $A^{18}$ is a bond that is present. In some versions, the --- between $A^{26}$ and $A^{18}$ is absent. The --- between any two adjacent atoms can be present or absent depending on the valency of the adjacent atoms.

In some versions, $L^1$ is O. In some versions, $L^1$ is $N(R^2)$. In some versions, $L^1$ is $C(R^2)_2$. In some versions, $L^2$ is O. In some versions, $L^2$ is $N(R^2)$. In some versions, $L^2$ is $C(R^2)_2$.

In some versions, $R^1$ is oxo. In some versions, $R^1$ is $N(R^2)_2$. In some versions, $R^1$ is methyl. In some versions, $R^1$ is ethyl. In some versions, $R^1$ is hydroxyl. In some versions, $R^1$ is unsubstituted C1-C2 alkyloxy. In some versions, $R^1$ is halogen.

In some versions, $A^2$, $A^4$, $A^5$, $A^7$, and $A^9$ are each independently $C(R^2)$; $A^{12}$ is N; $R^1$ is oxo; and $L^2$ is $N(R^2)$.

In some versions, $A^{11}$ is O or $N(R^2)$ and $A^{12}$ is N.

In some versions, $A^1$, $A^3$, $A^6$, and $A^8$ are each independently $C(R^2)$.

In some versions, $A^3$ is $C(R^2)$, and the $R^2$ of $A^3$ is optionally substituted C1-C6 alkyl.

In some versions, $A^{14}$ is $N(R^2)$ or N.

In some versions, $A^{14}$ is $N(R^2)$, and the $R^2$ of $A^{14}$ is optionally substituted C1-C6 alkyl.

In some versions, $A^{15}$ is $C(R^2)_2$ wherein one of the $R^2$ of $A^{15}$ is hydroxyl or optionally substituted alkyloxy.

In some versions, $A^{15}$ is $C(R^2)$, and the $R^2$ of $A^{15}$ is oxo.

In some versions, $A^{14}$ is $N(R^2)$, the $R^2$ of $A^{14}$ is optionally substituted C1-C6 alkyl, $A^{15}$ is $C(R^2)$, and the $R^2$ of $A^{15}$ is oxo.

In some versions, $A^{13}$, $A^{16}$, and $A^{17}$ are each independently $C(R^2)$.

In some versions, $A^2$, $A^4$, $A^5$, $A^7$, and $A^9$ are each independently $C(R^2)$; $A^{12}$ is N; $R^1$ is oxo; $L^2$ is $N(R^2)$; Z is $Z^1$; $A^{14}$ is $N(R^2)$, $A^{15}$ is $C(R^2)$, the $R^2$ of $A^{15}$ is oxo; and, optionally, the $R^2$ of $A^{14}$ is optionally substituted C1-C6 alkyl.

In some versions, $A^{18}$, $A^{24}$; $A^{25}$, and $A^{26}$ are each independently $C(R^2)$; the $R^2$ of $A^{26}$ is Y; $A^{19}$ and $A^{23}$ are each C; and, optionally, the $R^2$ of $A^{24}$ is hydrogen, halogen, or optionally substituted C1-C6 alkyl.

In some versions, $A^{21}$ is O, and $A^{20}$ and $A^{22}$ are each $C(R^2)_2$.

In some versions, $A^{20}$ is N, $A^{21}$ is $C(R^2)$, and $A^{22}$ is $N(R^2)$ or O.

In some versions, $A^2$, $A^4$, $A^5$, A', and $A^9$ are each independently $C(R^2)$; $A^{12}$ is N; $R^1$ is oxo; $L^2$ is $N(R^2)$; Z is $Z^2$; $A^{26}$ is $C(R^2)$; the $R^2$ of $A^{26}$ is Y; and either: $A^{21}$ is O; or $A^{20}$ is N and $A^{22}$ is $N(R^2)$ or O.

In some versions, each $R^2$, when present and except where defined otherwise, is independently hydrogen or halogen. In some versions, each $R^2$, when present and except where defined otherwise, is hydrogen.

In some versions, the compound has a structure of PX-02, PX-03, PX-04, PX-05, PX-06, PX-07, PX-08, PX-09, PX-10, PX-11, PX-12, PX-13, PX-14, PX-15, PX-16, PX-17, PX-18, PX-19, PX-20, PX-21, PX-22, PX-23, PX-24, PX-25, PX-26, PX-27, PX-28, PX-29, PX-30, PX-31, PX-32, PX-33, PX-34, PX-35, PX-36, or PX-37, or a salt of any of the foregoing.

The invention also provides methods of treating a condition in an animal with any one or more of the compounds described herein. The methods may comprise administering one or more of the compounds described herein to the animal in an amount effective to treat the condition. Conditions treatable with the compounds described herein include inflammatory or immune-mediated diseases, diabetes, infectious diseases, and cancers. Treatable inflammatory or immune-mediated diseases include autoimmune diseases. Treatable autoimmune diseases include systemic lupus erythematosus, rheumatoid arthritis, Sjogren's syndrome, multiple sclerosis, autoimmune encephalitis, type 1 diabetes, inflammatory bowel diseases (Crohn's disease, ulcerative colitis, inflammatory bowel syndrome, and complications arising from one or more of these conditions. Treatable diabetes conditions include diabetic nephropathy, diabetic retinopathy, chronic pain, neuropathy, deep vein thrombosis, or atherosclerosis. Treatable infectious diseases include infectious diseases of bacterial, fungal, and viral origin. Treatable cancers include pancreatic neuroendocrine carcinoma, non-small cell lung cancer, renal cell cancer, colorectal cancer, medullary thyroid cancer, hepatocellular carcinoma, thyroid carcinoma, cervical cancer, and cancers exhibiting metastasis in general.

The objects and advantages of the invention will appear more fully from the following detailed description of the preferred embodiment of the invention made in conjunction with the accompanying drawings.

BRIEF DESCRIPTION OF THE DRAWINGS

FIGS. 1A-1I. Computational prediction of binding of selected compounds to PLXDC2 in kcal/mol.

DETAILED DESCRIPTION OF THE INVENTION

Figure 1A:
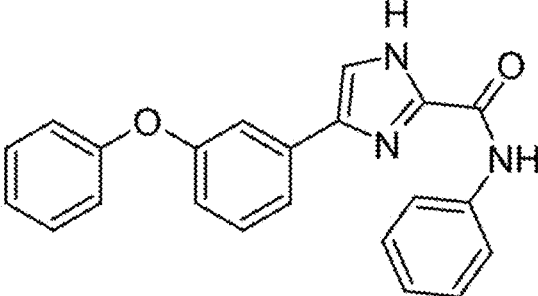
Figure 1A:
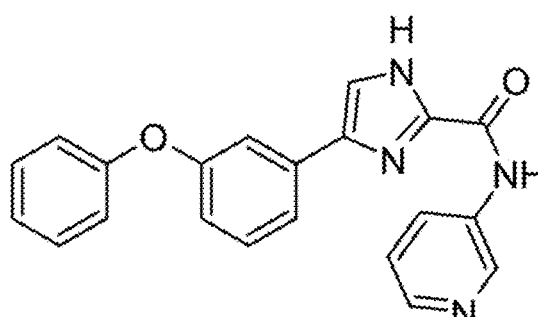
Figure 1A:
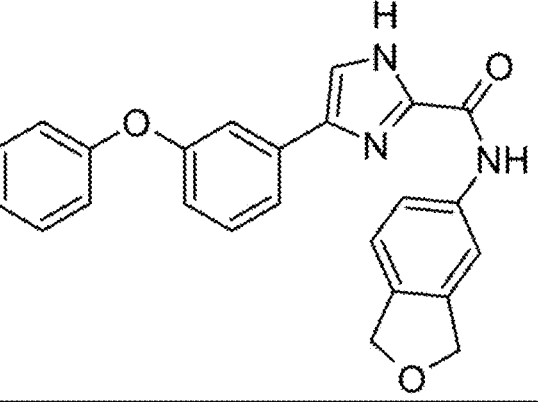
Figure 1A:
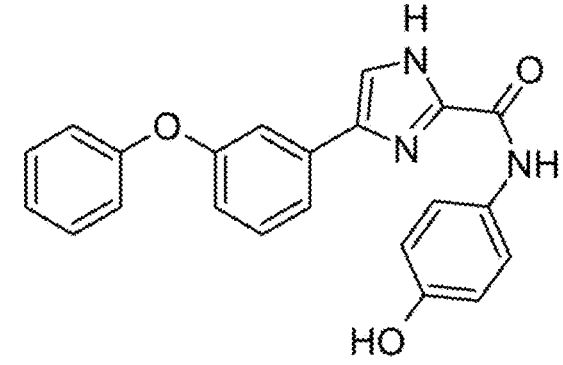
Figure 1B:
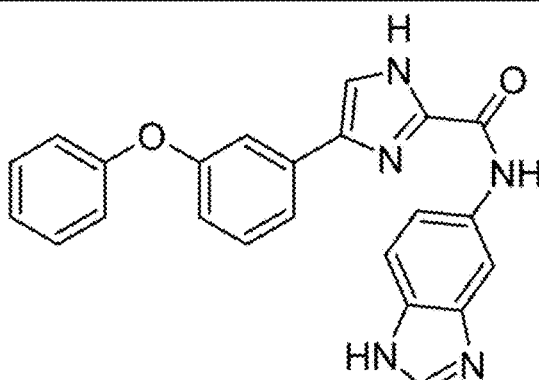
Figure 1B:
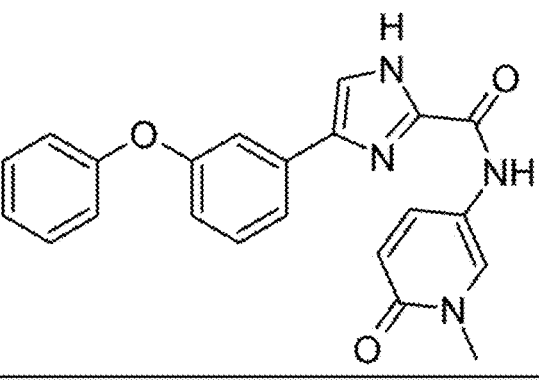
Figure 1B:
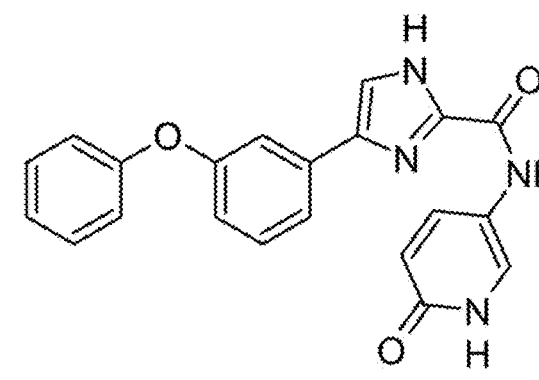
Figure 1B:
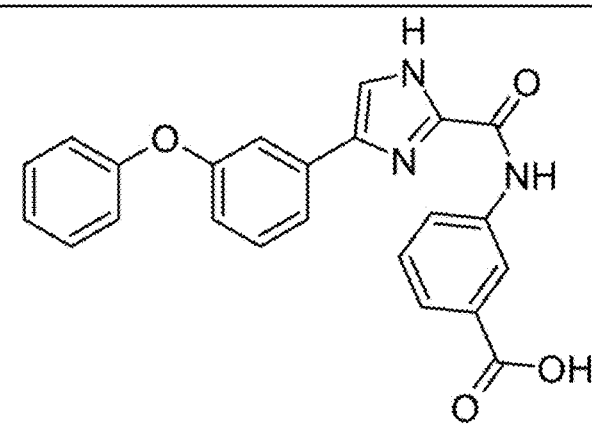
Figure 1C:
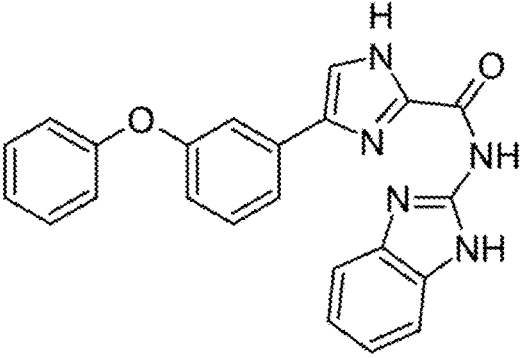
Figure 1C:
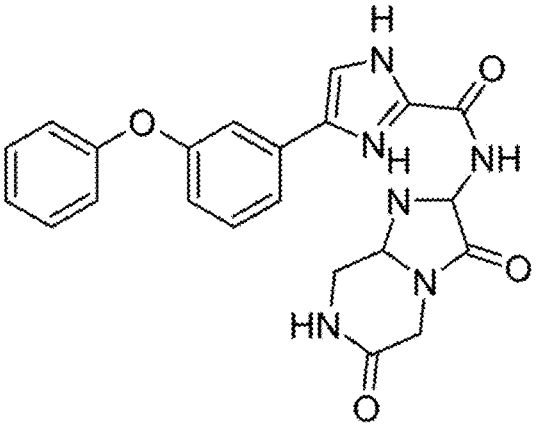
Figure 1C:
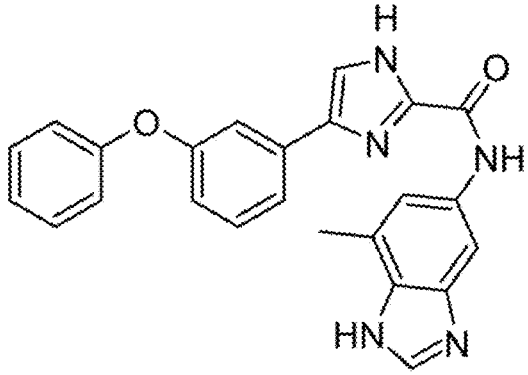
Figure 1C:
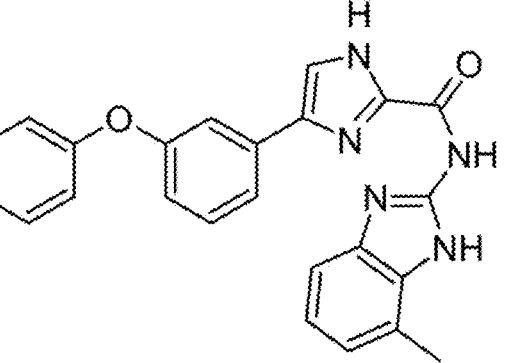
Figure 1D:
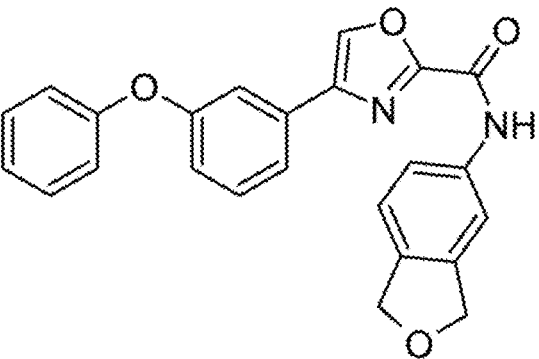
Figure 1D:
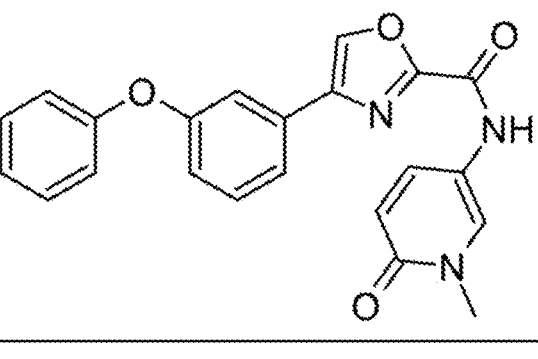
Figure 1D:
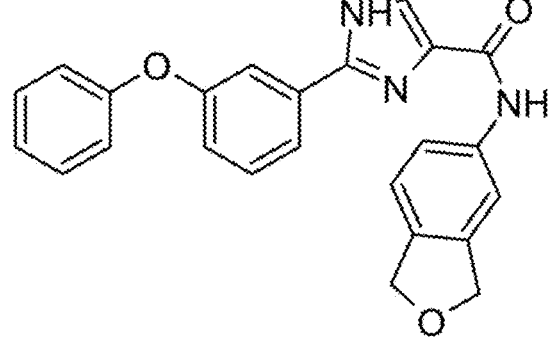
Figure 1D:
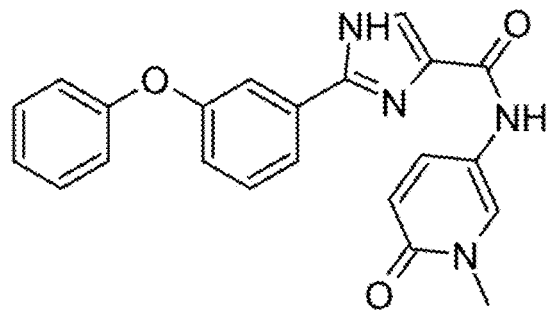
Figure 1E:
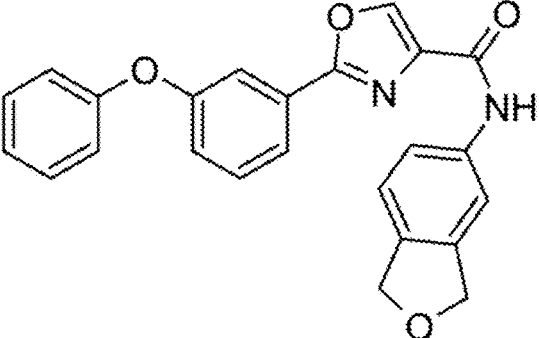
Figure 1E:
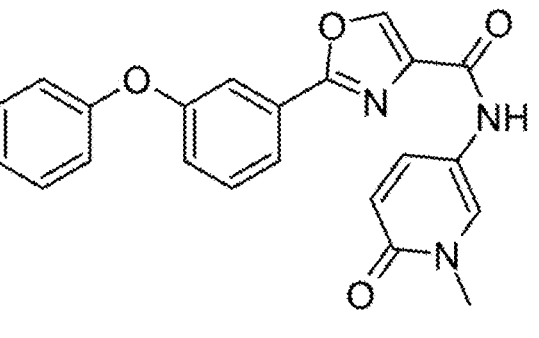
Figure 1E:
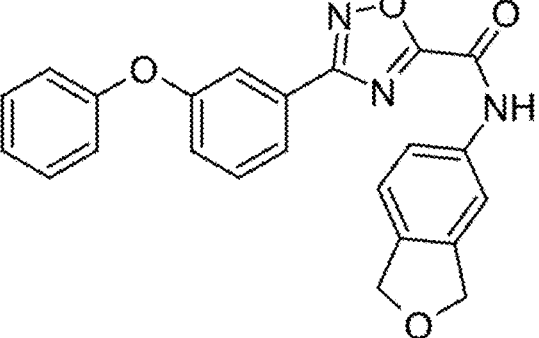
Figure 1E:
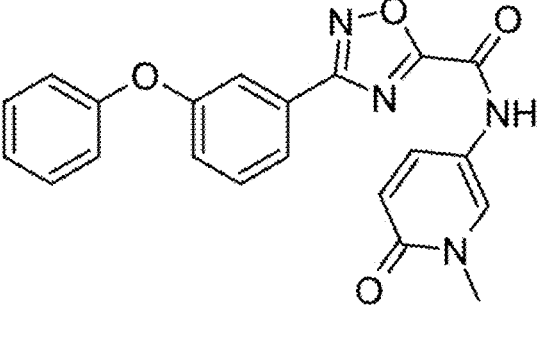
Figure 1G:
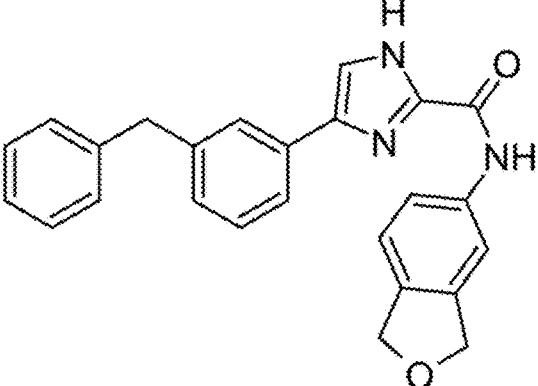
Figure 1G:
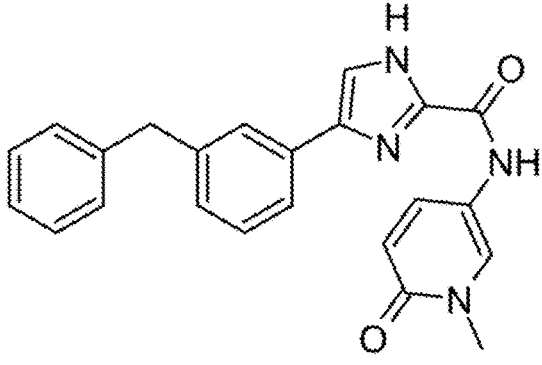
Figure 1G:
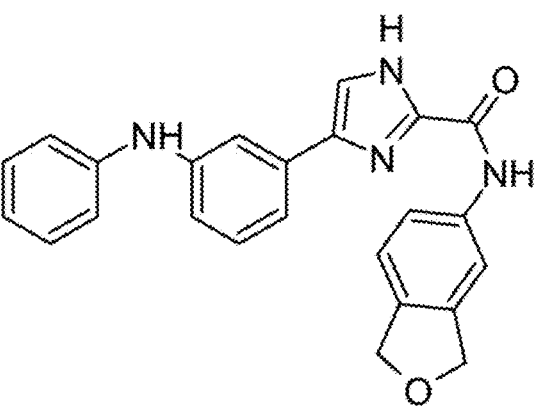
Figure 1G:
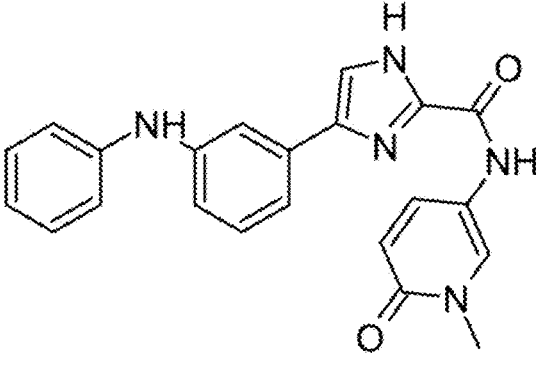
Figure 1I:
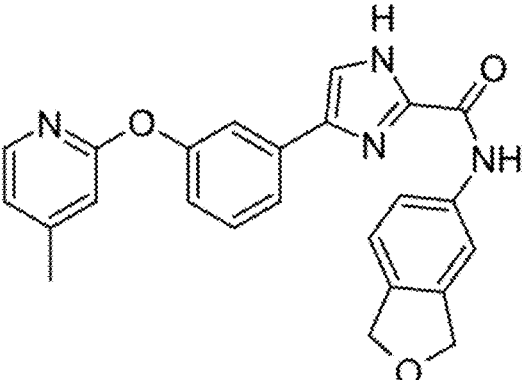
Figure 1I:
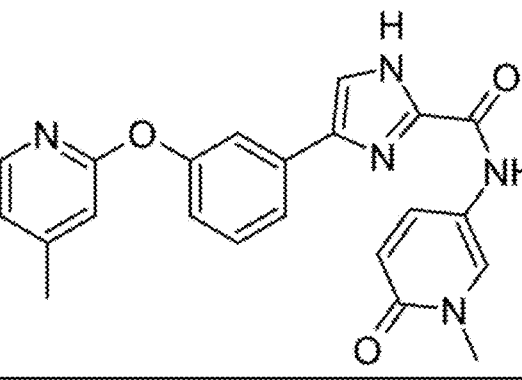
Figure 1I:
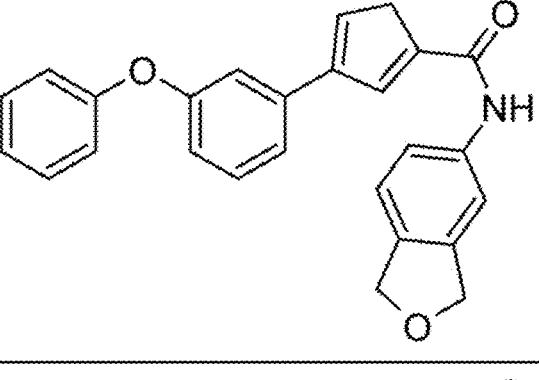
Figure 1I:
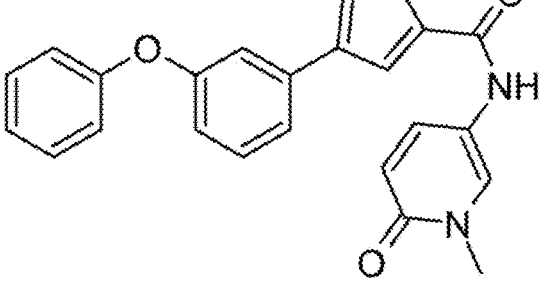

Unless otherwise stated, the following definitions are used throughout the present application.

Conjugated diene: A molecule containing two double bonds separated by a single bond.

Enantiomer: Optical isomer; chemical classification of molecules based on their ability to rotate the plain of polarization clockwise (+) or anti-clockwise (−).

Substantially pure: Having a purity of at least 90% by weight, preferably at least 95% by weight such as at least 98%, 99% or about 100% by weight.

IBD: Inflammatory bowel disease (IBD) involves chronic inflammation of all or part of your digestive tract. IBD primarily includes ulcerative colitis and Crohn's disease. Both usually involve severe diarrhea, pain, fatigue and weight loss. IBD can be debilitating and sometimes leads to life-threatening complications.

Ulcerative colitis (UC): UC is an IBD that causes long-lasting inflammation and sores (ulcers) in the innermost lining of the large intestine (colon) and rectum.

Crohn's Disease: Crohn's disease is an IBD that causes inflammation of the lining of the digestive tract. In Crohn's disease, inflammation often spreads deep into affected tissues. The inflammation can involve different areas of the digestive tract, such as the large intestine, small intestine or both.

IL-10: Interleukin-10 (IL-10), also known as human cytokine synthesis inhibitory factor (CSIF), is an anti-inflammatory cytokine. In humans, IL-10 is encoded by the IL10 gene.

TNF-alpha: Tumor necrosis factor (TNF, cachexin, or cachectin, and formerly known as tumor necrosis factor alpha or TNFα) is a cytokine involved in systemic inflammation and is a member of a group of cytokines that stimulate the acute phase reaction.

MCP1: Monocyte chemoattractant protein-1 is an older term for a CC cytokine critical for development of atherosclerotic lesions that is found in endothelial cells, macrophages and in vascular smooth muscle cells of patients undergoing coronary artery bypass procedures. The officially preferred term is now chemokine (C—C motif) ligand 2.

Interferon gamma: Interferon gamma is a pro-inflammatory dimerized soluble cytokine that is the only member of the type II class of interferons.

Leukocytic infiltration: Leukocyte infiltration refers to the process of moving or infiltrating of the leukocytes into the injured tissue to begin the repair process.

Type 1 diabetes: An autoimmune disease characterized as a chronic condition in which the pancreas produces little to no insulin as a result of immunological destruction of insulin-producing beta cells within pancreatic islets. The insulin deficiency leads to chronic hyperglycemia that can cause organ damage, shortened lifespan and reduced quality of life. The disease is also referred to as juvenile diabetes or insulin-dependent diabetes.

Systemic lupus erythematosus: An autoimmune disease in which the immune system reacts to nuclear antigens and forms immune complexes that can aggregate or cause damage to multiple organ systems including skin, joints, kidneys, brain, the heart and cardiovascular systems and other organs. As the most common form of lupus, systemic lupus erythematosus is often referred to simply as "lupus."

The term "halogen" refers to fluorine, chlorine, bromine, and iodine. Fluorine, chlorine, and bromine are preferable.

The term "hetero atom" refers to an oxygen atom, a sulfur atom, and a nitrogen atom.

The term "alkyl" includes a monovalent straight or branched hydrocarbon group having one to eight carbon atom(s). For example, methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl, and the like are exemplified. C1-C6 alkyl is preferred. C1-C4 alkyl is further preferred. When a number of carbon is specified, it means "alkyl" having the carbon number within the range.

The term "alkenyl" includes a monovalent straight or branched hydrocarbon group having two to eight carbon atoms and one or more double bond(s). For example, vinyl, allyl, 1-propenyl, 2-butenyl, 2-pentenyl, 2-hexenyl, 2-heptenyl, 2-octenyl, and the like are exemplified. C2-C6 alkenyl is preferred. Moreover, C2-C4 alkenyl is further preferred.

The term "alkynyl" includes a monovalent straight or branched hydrocarbon group having two to eight carbon atoms and one or more triple bond(s). For example, ethynyl, 1-propynyl, 2-propynyl, 2-butynyl, 2-pentynyl, 2-hexynyl, 2-heptynyl, 2-octynyl, and the like are exemplified. C2-C6 alkynyl is preferred. Moreover, C2-C4 alkynyl is further preferred.

The term "cycloalkyl" includes a cycloalkyl having three to eight carbon atoms. Cyclopropyl, cyclobutyl, cyclopentyl, cyclohexyl, cycloheptyl, cyclooctyl, and the like are exemplified. C3-C6 cycloalkyl is preferred.

The term "cycloalkenyl" includes a cycloalkenyl having three to eight carbon atoms. Cyclopropenyl, cyclobutenyl, cyclopentenyl, cyclohexenyl, cycloheptenyl, cyclooctenyl, and the like are exemplified. C3-C6 cycloalkenyl is preferred.

The term "alkyloxy" includes a group wherein an oxygen atom is substituted with one "alkyl" as described herein.

Methyloxy, ethyloxy, n-propyloxy, isopropyloxy, n-butyloxy, isobutyloxy, sec-butyloxy, tert-butyloxy, n-pentyloxy, isopentyloxy, 2-pentyloxy, 3-pentyloxy, n-hexyloxy, isohexyloxy, 2-hexyloxy, 3-hexyloxy, n-heptyloxy, n-octyloxy, and the like are exemplified. C1-C6 alkyloxy is preferred. Moreover, C1-C4 alkyloxy is further preferred. When a number of carbon is specified, it means "alkyloxy" having the carbon number within the range.

The term "alkenyloxy" includes a group wherein an oxygen atom is substituted with one "alkenyl" as described herein. Vinyloxy, allyloxy, 1-propenyloxy, 2-butenyloxy, 2-pentenyloxy, 2-hexenyloxy, 2-heptenyloxy, 2-octenyloxy, and the like are exemplified. C2-C6 alkenyloxy is preferred. Moreover, C2-C4 alkenyloxy is further preferred. When a number of carbon is specified, it means "alkenyloxy" having the carbon number within the range.

The term "alkynyloxy" includes a group wherein an oxygen atom is substituted with one "alkynyl" as described herein. Ethynyloxy, 1-propynyloxy, 2-propynyloxy, 2-butynyloxy, 2-pentynyloxy, 2-hexynyloxy, 2-heptynyloxy, 2-octynyloxy, and the like are exemplified. C2-C6 alkynyloxy is preferred. Moreover, C2-C4 alkynyloxy is further preferred. When a number of carbon is specified, it means "alkynyloxy" having the carbon number within the range.

The term "cycloalkyloxy" includes a group wherein an oxygen atom is substituted with one "cycloalkyl" as described herein. Cyclopropyloxy, cyclobutyloxy, cyclopentyloxy, cyclohexyloxy, cycloheptyloxy, and cyclooctyloxy are exemplified. C3-C6 cycloalkyloxy is preferred. When a number of carbon is specified, it means "cycloalkyloxy" having the carbon number within the range.

The term "cycloalkenyloxy" includes a group wherein an oxygen atom is substituted with one "cycloalkenyl" as described herein. Cyclopropenyloxy, cyclobutenyloxy, cyclopentenyloxy, cyclohexenyloxy, cycloheptenyloxy, and cyclooctenyloxy are exemplified. C3-C6 cycloalkenyloxy is preferred. When a number of carbon is specified, it means "cycloalkenyloxy" having the carbon number within the range.

The term "alkylthio" includes a group wherein a sulfur atom is substituted with one "alkyl" as described herein. Methylthio, ethylthio, n-propylthio, isopropylthio, n-butylthio, isobutylthio, sec-butylthio, tert-butylthio, n-pentylthio, isopentylthio, 2-pentylthio, 3-pentylthio, n-hexylthio, isohexylthio, 2-hexylthio, 3-hexylthio, n-heptylthio, n-octylthio, and the like are exemplified. C1-C6 Alkylthio is preferred. Moreover, C1-C4 alkylthio is further preferred. When a number of carbon is specified, it means "alkylthio" having the carbon number within the range.

The term "alkenylthio" includes a group wherein a sulfur atom is substituted with one "alkenyl" as described herein. Vinylthio, allylthio, 1-propenylthio, 2-butenylthio, 2-pentenylthio, 2-hexenylthio, 2-heptenylthio, 2-octenylthio, and the like are exemplified. C2-C6 Alkenylthio is preferred. Moreover, C2-C4 alkylthio is further preferred. When a number of carbon is specified, it means "alkenylthio" having the carbon number within the range. The term "alkynylthio" includes a group wherein a sulfur atom is substituted with one "alkynyl" as described herein. Ethynylthio, 1-propynylthio, 2-propynylthio, 2-butynylthio, 2-pentynylthio, 2-hexynylthio, 2-heptynylthio, 2-octynylthio, and the like are exemplified. C2-C6 alkynylthio is preferred. Moreover, C2-C4 alkynylthio is further preferred. When a number of carbon is specified, it means "alkynylthio" having the carbon number within the range.

The term "alkylsulfinyl" includes a group wherein sulfinyl is substituted with one "alkyl" as described herein. Methylsulfinyl, ethylsulfinyl, n-propylsulfinyl, isopropylsulfinyl, n-butylsulfinyl, isobutylsulfinyl, sec-butyl sulfinyl, tert-butylsulfinyl, n-pentyl sulfinyl, isopentylsulfinyl, 2-pentylsulfinyl, 3-pentyl sulfinyl, n-hexylsulfinyl, isohexylsulfinyl, 2-hexylsulfinyl, 3-hexyl sulfinyl, n-heptylsulfinyl, n-octylsulfinyl, and the like are exemplified. C1-C6 alkylsulfinyl is preferred. Moreover, C1-C4 alkylsulfinyl is further preferred.

The term "alkylsulfonyl" includes a group whereinsulfonyl is substituted with one "alkyl" as described herein. Methylsulfonyl, ethylsulfonyl, n-propylsulfonyl, isopropylsulfonyl, n-butylsulfonyl, isobutylsulfonyl, sec-butylsulfonyl, tert-butylsulfonyl, n-pentylsulfonyl, isopentylsulfonyl, 2-pentylsulfonyl, 3-pentylsulfonyl, n-hexylsulfonyl, isohexylsulfonyl, 2-hexylsulfonyl, 3-hexylsulfonyl, n-heptylsulfonyl, n-octylsulfonyl, and the like are exemplified. C1-C6 alkylsulfonyl is preferred. Moreover, C1-C4 alkylsulfonyl is further preferred.

The term "alkylsulfonyloxy" includes a group wherein an oxygen atom is substituted with one "alkylsulfonyl" as described herein. Methylsulfonyloxy, ethylsulfonyloxy, n-propylsulfonyloxy, isopropylsulfonyloxy, n-butylsulfonyloxy, isobutylsulfonyloxy, sec-butylsulfonyloxy, tert-butylsulfonyloxy, n-pentylsulfonyloxy, isopentylsulfonyloxy, 2-pentylsulfonyloxy, 3-pentylsulfonyloxy, n-hexylsulfonyloxy, isohexylsulfonyloxy, 2-hexylsulfonyloxy 3-hexylsulfonyloxy, n-heptylsulfonyloxy, n-octylsulfonyloxy, and the like are exemplified. C1-C6 alkylsulfonyl is preferred. Moreover, C1-C4 alkylsulfonyl is further preferred.

The term "cycloalkylthio" includes a group wherein a sulfur atom is substituted with one "cycloalkyl" as described herein. Cyclopropylthio, cyclobutylthio, cyclopentylthio, cyclohexylthio, cycloheptylthio, cyclooctylthio, and the like are exemplified. C3-C6 cycloalkylthio is preferred. When a number of carbon is specified, it means "cycloalkylthio" having the carbon number within the range.

The term "cycloalkylsulfinyl" includes a group in which sulfinyl is substituted with one "cycloalkyl" as described herein. Cyclopropylsulfinyl, cyclobutylsulfinyl, cyclopentylsulfinyl, cyclohexylsulfinyl, cycloheptylsulfinyl, and cyclooctylsulfinyl are exemplified. Preferably C3-C6 cycloalkylsulfinyl is exemplified.

The term "cycloalkylsulfonyl" includes a group in whichsulfonyl is substituted with one "cycloalkyl" as described herein. Cyclopropylsulfonyl, cyclobutylsulfonyl, cyclopentylsulfonyl, cyclohexylsulfonyl, cycloheptylsulfonyl, and cyclooctylsulfonyl are exemplified. Preferably C3-C6 cycloalkylsulfonyl is exemplified.

The term "cycloalkylsulfonyloxy" includes a group in which an oxygen atom is substituted with one "cycloalkylsulfonyl" as described herein. Cyclopropylsulfonyloxy, cyclobutylsulfonyloxy, cyclopentylsulfonyloxy, cyclohexylsulfonyloxy, cycloheptylsulfonyloxy, and cyclooctylsulfonyloxy are exemplified. Preferably C3-C6 cycloalkylsulfonyloxy is exemplified.

The term "cycloalkenylthio" includes a group in which a sulfur atom is substituted with one "cycloalkenyl" as described herein. Cyclopropenylthio, cyclobutenylthio, cyclopentenylthio, cyclohexenylthio, cycloheptenylthio, and cyclooctenylthio are exemplified. Preferably C3-C6 cycloalkenylthio is exemplified. When a number of carbon is specified, it means "cycloalkenylthio" having the carbon number within the range.

The term "cycloalkenylsulfinyl" includes a group in which sulfinyl is substituted with one "cycloalkenyl" as described herein. Cyclopropenylsulfinyl, cyclobutenylsulfinyl, cyclopentenylsulfinyl, cyclohexenylsulfinyl, cycloheptenylsulfinyl, and cyclooctenylsulfinyl are exemplified. Preferably C3-C6 cycloalkenylsulfinyl is exemplified. The term "cycloalkenylsulfonyl" includes a group in whichsulfonyl is substituted with one "cycloalkenyl" as described herein. Cyclopropenylsulfonyl, cyclobutenylsulfonyl, cyclopentenyl sul fonyl, cyclohexenylsulfonyl, cycloheptenylsulfonyl, and cyclooctenylsulfonyl are exemplified. Preferably C3-C6 cycloalkenylsulfonyl is exemplified.

The term "cycloalkenylsulfonyloxy" includes a group in which an oxygen atom is substituted with one "cycloalkenylsulfonyl" described as described herein. For example, cyclopropenylsulfonyloxy, cyclobutenylsulfonyloxy, cyclopentenylsulfonyloxy, cyclohexenylsulfonyloxy, cycloheptenylsulfonyloxy, and cyclooctenylsulfonyloxy are exemplified. Preferably C3-C6 cycloalkenylsulfonyloxy is exemplified.

The term "alkyloxycarbonyl" includes a group in which carbonyl is substituted with one "alkyloxy" as described herein. Methyloxycarbonyl, ethyloxycarbonyl, n-propyloxycarbonyl, isopropyloxycarbonyl, n-butyloxycarbonyl, tert-butyloxycarbonyl, and n-pentyl oxycarbonyl are exemplified. Preferably C1-C6 or C1-C4 alkyloxycarbonyl is exemplified. Moreover, C1-C2 alkyloxycarbonyl is further preferable.

The term "alkenyloxycarbonyl" includes a group in which carbonyl is substituted with one "alkenyloxy" as described herein. Vinyloxycarbonyl, allyloxycarbonyl, 1-propenyloxycarbonyl, 2-butenyloxycarbonyl, and 2-pentenyloxyarbonyl are exemplified. Preferably C2-C6 or C2-C4 alkyloxycarbonyl is exemplified.

The term "alkynyloxycarbonyl" includes a group in which carbonyl is substituted with one "alkynyloxy" as described herein. Ethynyloxycarbonyl, 1-propynyloxycarbonyl, 2-propynyloxycarbonyl, 2-butynyloxyarbonyl, and 2-pentynyloxycarbonyl are exemplified. Preferably C2-C6 or C2-C4 alkynyloxycarbonyl is exemplified.

The term "acyl" includes alkylcarbonyl wherein the part of alkyl is "alkyl" as described herein, alkenylcarbonyl wherein the part of alkenyl is "alkenyl" as described herein, alkynylcarbonyl wherein the part of alkynyl is "alkynyl" as described herein, cycloalkylcarbonyl wherein the part of cycloalkyl is "cycloalkyl" as described herein, arylcarbonyl wherein the part of aryl is "aryl" as described herein, heteroarylcarbonyl wherein the part of heteroaryl is "heteroaryl" as described herein, and non-aromatic heterocyclic-carbonyl wherein the part of non-aromatic heterocyclic group is "non-aromatic heterocyclic group" as described herein. "Alkyl," "alkenyl," "alkynyl," "cycloalkyl," "aryl," "heteroaryl," and "non-aromatic heterocyclic group" may be substituted respectively with substituent groups exemplified in "optionally substituted alkyl," "optionally substituted alkenyl," "optionally substituted alkynyl," "optionally substituted cycloalkyl," "optionally substituted aryl," "optionally substituted heteroaryl," and "optionally substituted non-aromatic heterocyclic group" as described herein. Examples of the acyl group include acetyl, propionyl, butyroyl, cyclohexylcarbonyl, benzoyl, pyridinecarbonyl, and the like.

The term "optionally substituted amino" includes an amino group which may be substituted with one or two group(s) of "alkyl" as described herein, "alkenyl" as described herein, "alkynyl" as described herein, "cycloalkyl" as described herein, "cycloalkynyl" as described herein, "aryl" as described herein, "heteroaryl" as described herein, "acyl" as described herein, "alkyloxycarbonyl" as described herein, "alkenyloxycarbonyl" as described herein, "alkynyloxycarbonyl" as described herein, "alkylsulfonyl," "alkenylsulfonyl," "alkynylsulfonyl," "arylsulfonyl," and/or "heteroarylsulfonyl" as described herein. Examples of the optionally substituted amino group include amino, methylamino, dimethylamino, ethylamino, diethylamino, ethylmethylamino, benzylamino, acetylamino, benzoylamino, methyloxycarbonylamino, and methanesulfonylamino. Preferably, amino, methylamino, dimethylamino, ethylmethylamino, diethylamino, acetylamino, and methanesulfonylamino are exemplified.

The term "optionally substituted carbamoyl" includes an aminocarbonyl group wherein the part of optionally substituted amino is "optionally substituted amino" as described herein. Examples of the optionally substituted carbamoyl group includes carbamoyl, N-methylcarbamoyl, N,N-dimethyl carbamoyl, N-ethyl-N-methylcarbamoyl, N,N-diethylcarbamoyl, N-phenylcarbamoyl, N-benzylcarbamoyl, N-acetylcarbamoyl, and N-methylsulfonylcarbamoyl etc. Preferably, carbamoyl, N-methylcarbamoyl, N,N-dimethylcarbamoyl, and N-methylsulfonylcarbamoyl etc. are exemplified.

The term "optionally substituted sulfamoyl" includes an aminosulfonyl group wherein the part of optionally substituted amino is "optionally substituted amino" as described herein. Examples of the optionally substituted sulfamoyl group include sulfamoyl, N-methylsulfamoyl, N,N-dimethylsulfamoyl, N-ethyl-N-methyl sulfamoyl, N,N-diethylsulfamoyl, N-phenylsulfamoyl, N-benzylsulfamoyl, N-acetylsulfamoyl, and N-methylsulfonylsulfamoyl etc. Preferably, sulfamoyl, N-methylsulfamoyl, N,N-dimethylsulfamoyl, and N-methylsulfonylsulfamoyl etc. are exemplified.

The term "alkylene" means a straight or branched alkylene group having one to eight carbon atom(s). Examples include methylene, ethylene, 1-methylethylene, trimethylene, 1-methyltrimethylene, pentamethylene, hexamethylene, and the like. Preferably C1-C4 alkylene is exemplified. Moreover, C1-C2 alkylene is further preferred.

The term "aryl" includes an aromatic monocyclic or aromatic fused cyclic hydrocarbons. It may be fused with "cycloalkyl" as described herein, "cycloalkenyl" as described herein or "non-aromatic heterocyclic group" as described herein at any possible position. Both of monocyclic ring and fused ring may be substituted at any position. Phenyl, 1-naphthyl, 2-naphthyl, anthryl, tetrahydronaphthyl, 1,3-benzodioxolyl, 1,4-benzodioxanyl etc. are exemplified. Phenyl, 1-naphthyl, and 2-naphthyl are preferred. Moreover, phenyl is further preferred.

The term "non-aromatic heterocyclic group" includes a 5- to 7-membered non-aromatic heterocyclic ring containing one or more of heteroatom(s) selected independently from oxygen, sulfur, and nitrogen atoms or a multicyclic ring formed by fusing the two or more rings thereof. Pyrrolidinyl (e.g., 1-pyrrolidinyl, 2-pyrrolidinyl), pyrrolinyl (e.g., 3-pyrrolinyl), imidazolidinyl (e.g., 2-imidazolidinyl), imidazolinyl (e.g., imidazolinyl), pyrazolidinyl (e.g., 1-pyrazolidinyl, 2-pyrazolidinyl), pyrazolinyl (e.g., pyrazolinyl), piperidyl (e.g., piperidino, 2-piperidyl), piperazinyl (e.g., 1-piperazinyl), indolinyl (e.g., 1-indolinyl), isoindolinyl (e.g., isoindolinyl), morpholinyl (e.g., morpholino, 3-morpholinyl) etc. are exemplified.

The term "heteroaryl" includes a 5- to 6-membered aromatic ring containing one or more of heteroatom(s) selected independently from oxygen, sulfur, and nitrogen atoms. It may be fused with "cycloalkyl" as described herein, "aryl" as described herein, "non-aromatic heterocyclic group" as described herein, or other heteroaryl at any possible position. The heteroaryl group may be substituted at any position whenever it is a monocyclic ring or a fused ring. For example, pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1H-tetrazolyl), oxadiazolyl (e.g., 1,3,4-oxadiazolyl), thiadiazolyl (e.g., 1,3,4-thiadiazolyl), indolidinyl (e.g., 2-indolidinyl, 6-indolidinyl), isoindolynyl (e.g., 2-isoindolynyl), indolyl (e.g., 1-indolyl, 2-indolyl, 3-indolyl), indazolyl (e.g., 3-indazolyl), purinyl (e.g., 8-purinyl), quinolidinyl (e.g., 2-quinolidinyl), isoquinolyl (e.g., 3-isoquinolyl), quinolyl (e.g., 2-quinolyl, 5-quinolyl), phtharazinyl (e.g., 1-phtharazinyl), naphthylidinyl (e.g., 2-naphthylidinyl), quinolanyl (e.g., 2-quinolanyl), quinazolinyl (e.g., 2-quinazolinyl), cinnolinyl (e.g., 3-cinnolinyl), pteridinyl (e.g., 2-pteridinyl), carbazolyl (e.g., 2-carbazolyl, 4-carbazolyl), phenanthridinyl (e.g., 2-phenanthridinyl, 3-phenanthridinyl), acridinyl (e.g., 1-acridinyl, 2-acridinyl), dibenzofuranyl (e.g., 1-dibenzofuranyl, 2-dibenzofuranyl), benzoimidazolyl (e.g., 2-benzoimidazolyl), benzoisoxazolyl (e.g., 3-benzoisoxazolyl), benzooxazolyl (e.g., 2-benzooxazolyl), benzooxadiazolyl (e.g., 4-b enzooxadiazolyl), benzoisothiazolyl (e.g., 3-benzoisothiazolyl), benzothiazolyl (e.g., 2-benzothiazolyl), benzofuryl (e.g., 3-benzofuryl), benzothienyl (e.g., 2-benzothienyl), dibenzothienyl (e.g., 2-dibenzothienyl), and benzodioxolyl (e.g., 1,3-benzodioxolyl) etc. are exemplified.

The term "aryloxy" includes a group in which an oxygen atom is substituted with one "aryl" as described herein. Phenyloxy and naphthyloxy etc. are exemplified.

The term "arylthio" includes a group in which a sulfur atom is substituted with one "aryl" as described herein. Phenylthio and naphthylthio etc. are exemplified.

The term "arylsulfinyl" includes a group in which sulfinyl is substituted with one "aryl" as described herein. Phenylsulfinyl and naphthylsulfinyl etc. are exemplified.

The term "arylsulfonyl" includes a group in whichsulfonyl is substituted with one "aryl" as described herein. Phenylsulfonyl and naphthylsulfoinyl etc. are exemplified.

Examples of "arylsulfonyloxy include phenylsulfonyloxy and naphthylsulfonyloxy etc.

The term "aryloxycarbonyl" includes a group in which carbonyl is substituted with one "aryloxy" as described herein. Phenyloxycarbonyl, 1-naphthyloxycarbonyl and 2-naphthyloxycarbonyl etc. are exemplified.

The term "heteroaryloxy" includes a group in which an oxygen atom is substituted with one "heteroaryl" as described herein. Pyrrolyloxy, furyloxy, thienyloxy, imidazolyloxy, pyrazolyloxy, isothiazolyloxy, isoxazolyloxy, oxazolyloxy, thiazolyloxy, pyridyloxy, pyrazinyloxy, pyrimidinyloxy, pyridazinyloxy, tetrazolyloxy, oxadiazolyloxy, thiadiazolyloxy, indolidinyloxy, isoindolynyloxy, indolyloxy, indazolyloxy, purinyloxy, quinolidinyloxy, isoquinolyloxy, quinolyloxy, phtharazinyloxy, naphthylidinyloxy, quinolanyloxy, quinazolinyloxy, cinnolinyloxy, pteridinyloxy, carbazolyloxy, phenanthridinyloxy, acridinyloxy, dibenzofuranyloxy, benzoimidazolyloxy, benzoisoxazolyloxy, benzooxazolyloxy, benzooxadiazolyloxy, benzoisothiazolyloxy, benzothiazolyloxy, benzofuryloxy, benzothienyloxy, dibenzothienyloxy, and benzodioxolyloxy are exemplified. Preferably furyloxy, thienyloxy, imidazolyloxy, pyrazolyloxy, isothiazolyloxy, isoxazolyloxy, oxazolyloxy, thiazolyloxy, pyridyloxy, pyrazinyloxy, pyrimidinyloxy, and pyridazinyloxy are exemplified.

The term "heteroarylthio" includes a group in which a sulfur atom is substituted with one "heteroaryl" as described herein. Pyrrolylthio, furylthio, thienylthio, imidazolylthio, pyrazolylthio, isothiazolylthio, isoxazolylthio, oxazolylthio, thiazolylthio, pyridylthio, pyrazinylthio, pyrimidinylthio, pyridazinylthio, tetrazolylthio, oxadiazolylthio, thiadiazolylthio, indolidinylthio, isoindolynylthio, indolylthio, indazolylthio, purinylthio, quinolidinylthio, isoquinolylthio, quinolylthio, phtharazinylthio, naphthylidinylthio, quinolanylthio, quinazolinylthio, cinnolinylthio, pteridinylthio, carbazolylthio, phenanthridinylthio, acridinylthio, dibenzofuranylthio, benzoimi dazolylthio, benzoisoxazolylthio, benzooxazolylthio, benzooxadiazolylthio, benzoisothiazolylthio, benzothiazolylthio, benzofurylthio, benzothienylthio, dibenzothienylthio, and benzodioxolylthio etc. are exemplified. Preferably furylthio, thienylthio, imidazolylthio, pyrazolylthio, isothiazolylthio, isoxazolylthio, oxazolylthio, thiazolylthio, pyridylthio, pyrazinylthio, pyrimidinylthio, and pyridazinylthio etc. are exemplified.

The term "heteroarylsulfinyl" includes a group in which sulfinyl is substituted with one "heteroaryl" as described herein. Pyrrolylsulfinyl, furylsulfinyl, thienylsulfinyl, imidazolylsulfinyl, pyrazolylsulfinyl, isothiazolylsulfinyl, isoxazolylsulfinyl, oxazolylsulfinyl, thiazolylsulfinyl, pyridylsulfinyl, pyrazinylsulfinyl, pyrimidinylsulfinyl, pyridazinylsulfinyl, tetrazolylsulfinyl, oxadiazolylsulfinyl, thiadiazolylsulfinyl, indolidinylsulfinyl, isoindolylsulfinyl, indolylsulfinyl, indazolylsulfinyl, purinylsulfinyl, quinolidinylsulfinyl, isoquinolylsulfinyl, quinolylsulfinyl, phtharazinylsulfinyl, naphthylidinylsulfinyl, quinolanylsulfinyl, quinazolinylsulfinyl, cinnolinylsulfinyl, pteridinylsulfinyl, carbazolylsulfinyl, phenanthridinylsulfinyl, acridinylsulfinyl, dibenzofuranylsulfinyl, benzoimidazolylsulfinyl, benzoisoxazolylsulfinyl, benzooxazolylsulfinyl, benzooxadiazolylsulfinyl, benzoisothiazolylsulfinyl, benzothiazolylsulfinyl, benzofurylsulfinyl, benzothienylsulfinyl, dibenzothienylsulfinyl, and benzodioxolylsulfinyl etc. are exemplified. Preferably furylsulfinyl, thienylsulfinyl, imidazolylsulfinyl, pyrazolylsulfinyl, isothiazolylsulfinyl, isoxazolylsulfinyl, oxazolylsulfinyl, thiazolylsulfinyl, pyridylsulfinyl, pyrazinylsulfinyl, pyrimidinylsulfinyl, and pyridazinylsulfinyl etc. are exemplified.

The term "heteroarylsulfonyl" includes a group in whichsulfonyl is substituted with one "heteroaryl" as described herein. For example, pyrrolylsulfonyl, furylsulfonyl, thienylsulfonyl, imidazolylsulfonyl, pyrazolylsulfonyl, isothiazolylsulfonyl, isoxazolylsulfonyl, oxazolylsulfonyl, thiazolylsulfonyl, pyridylsulfonyl, pyrazinylsulfonyl, pyrimidinylsulfonyl, pyridazinylsulfonyl, tetrazolylsulfonyl, oxadiazolylsulfonyl, thiadiazolylsulfonyl, indolizinylsulfonyl, isoindolylsulfonyl, indolylsulfonyl, indazolylsulfonyl, purinylsulfonyl, quinolidinylsulfonyl, isoquinolylsulfonyl, quinolylsulfonyl, phtharazinylsulfonyl, naphthilidinylsulfonyl, quinolanylsulfonyl, quinazolinylsulfonyl, cinnolinylsulfonyl, pteridinylsulfonyl, carbazolylsulfonyl, phenanthridinylsulfonyl, acridinylsulfonyl, dibenzofuranylsulfonyl, benzoimidazolylsulfonyl, benzoisoxazolylsulfonyl, benzooxazolylsulfonyl, benzooxadiazolylsulfonyl, benzoisothiazolylsulfonyl, benzothiazolylsulfonyl, benzofurylsulfonyl, benzothienylsulfonyl, dibenzothienylsulfonyl, and benzodioxolylsulfonyl are exemplified. Preferably furylsulfonyl, thienylsulfonyl, imidazolylsulfonyl, pyrazolylsulfonyl, isothiazolylsulfonyl, isoxazolylsulfonyl, oxazolylsulfonyl, thiazolylsulfonyl, pyridylsulfonyl, pyrazinylsulfonyl, pyrimidinylsulfonyl, and pyridazinylsulfonyl are exemplified.

The term "heteroarylsulfonyloxy" includes a group in which an oxygen atom is substituted with one "heteroarylsulfonyl" as described herein. For example, pyrrolylsulfonyloxy, furylsulfonyloxy, thienylsulfonyloxy, imidazolylsulfonyloxy, pyrazolylsulfonyloxy, isothiazolylsulfonyloxy, isoxazolylsulfonyloxy, oxazolylsulfonyloxy, thiazolylsulfonyloxy, pyridylsulfonyloxy, pyrazinylsulfonyloxy, pyrimidinylsulfonyloxy, pyridazinylsulfonyloxy, tetrazolylsulfonyloxy, oxadiazolylsulfonyloxy, thiadiazolylsulfonyloxy, indolizinylsulfonyloxy, isoindolylsulfonyloxy, indolylsulfonyloxy, indazolylsulfonyloxy, purinylsulfonyloxy, quinolidinylsulfonyloxy, isoquinolylsulfonyloxy, quinolylsulfonyloxy, phtharazinylsulfonyloxy, naphthilidinylsulfonyloxy, quinolanyl sulfonyloxy, quinazolinylsulfonyloxy, cinnolinylsulfonyloxy, pteridinylsulfonyloxy, carbazolylsulfonyloxy, phenanthridinylsulfonyloxy, acridinylsulfonyloxy, dibenzofuranylsulfonyloxy, benzoimidazolylsulfonyloxy, benzoisoxazolylsulfonyloxy, benzooxazolylsulfonyloxy, benzooxadiazolylsulfonyloxy, benzoisothiazolylsulfonyloxy, benzothiazolylsulfonyloxy, benzofurylsulfonyloxy, benzothienylsulfonyloxy, dibenzothienylsulfonyloxy, and benzodioxolylsulfonyloxy etc. are exemplified. Preferably, furylsulfonyloxy, thienylsulfonyloxy, imidazolylsulfonyloxy, pyrazolylsulfonyloxy, isothiazolylsulfonyloxy, isoxazolylsulfonyloxy, oxazol ylsulfonyloxy, thiazolylsulfonyloxy, pyridylsulfonyloxy, pyrazinylsulfonyl oxy, pyrimidinylsulfonyloxy, and pyridazinylsulfonyloxy etc. are exemplified.

The term "aromatic carbocyclic ring" includes an aromatic monocyclic or aromatic fused carbocyclic ring. A benzene ring, a naphthalene ring, and an anthracene ring are exemplified. A benzene ring is preferred.

The term "aromatic heterocyclic ring" includes an aromatic monocyclic or aromatic fused heterocyclic ring. A pyrrole ring, a furan ring, a thiophen ring, a pyrazole ring, an imidazole ring, an isothiazole ring, an isoxazole ring, an oxazole ring, a thiazole ring, a pyrazine ring, a pyrimidine ring, a pyridazine ring, a tetrazole ring, an oxadiazole ring, a thiadiazole ring, an indolizine ring, an isoindole ring, an indole ring, an indazole ring, a purine ring, a quinolidine ring, an isoquinoline ring, a quinoline ring, a phtharazine ring, a naphthyridine ring, a quinolane ring, a quinazoline ring, a cinnoline ring, a pteridine ring, a carbazole ring, a phenanthridine ring, an acridine ring, a dibenzofuran ring, a benzimidazole ring, a benzisoxazole ring, a benzoxazole ring, a benzoxadiazole ring, a benzisothiazole ring, a benzothiazole ring, a benzofuran ring, a benzothiophene ring, a dibenzothiophene ring, and a benzodixolane ring are exemplified. Preferably a pyridine ring, a furan ring, and a thiophen ring are exemplified.

The term "C1-C6 alkylene" includes a straight or branched alkylene group having one to six carbon atom(s). Examples include —$CH_2$—, —$CH(CH_3)$—, —$C(CH_3)_2$—, —$CH_2CH_2$—, —$CH(CH_3)CH_2$—, —$C(CH_3)_2CH_2$—, —$CH_2CH_2CH_2$—, —$CH_2CH_2CH_2CH_2$—, —$CH_2CH_2CH_2CH_2CH_2$—, and —$CH_2CH_2CH_2CH_2CH_2CH_2$—. Preferably, —$CH_2$—, —$CH_2CH_2$—, —$CH_2CH_2CH_2$—, and —$CH_2CH_2CH_2CH_2$— are exemplified.

The term "alkylene optionally containing one or two heteroatom(s)" of "optionally substituted alkylene optionally containing one or two heteroatom(s)" includes a straight or branched alkylene group having one to six carbon atoms, optionally containing one or two heteroatom(s) which may be substituted with "alkyl" as described herein. Examples include —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH_2O$—, —$OCH_2$—, —$CH_2CH_2O$—, —$OCH_2CH_2$—, —$CH_2S$—, —$SCH_2$—, —$CH_2CH_2S$—, —$SCH_2CH_2$—, —$CH_2CH_2OCH_2CH_2$—, —$OCH_2CH_2O$—, —$OCH_2O$—, —$NHCH_2$—, —$N(CH_3)CH_2$—, —$N^+(CH_3)_2CH_2$—, —$NHCH_2CH_2CH_2$—, and —$N(CH_3)CH_2CH_2CH_2$—, etc. Preferably, —$CH_2$—, —$CH_2CH_2$—, —$CH_2CH_2CH_2$—, —$CH_2CH_2CH_2CH_2$—, —$OCH_2CH_2O$—, —$OCH_2O$—, and —$N(CH_3)CH_2CH_2CH_2$— are exemplified.

The term "alkenylene optionally containing one or two heteroatom(s)" of "optionally substituted alkylene optionally containing one or two heteroatom(s)" includes a straight or branched alkenylene group having two to six carbon atoms, optionally containing one or two heteroatom(s) which may be substituted with "alkyl" as described herein. Examples include —CH=CHCH=CH—, —CH=CHO—, —OCH=CH—, —CH=CHS—, —SCH=CH—, —CH=CHNH—, —NHCH=CH—, —CH=CH—CH=N—, and —N=CH—CH=CH—. Preferably, —CH=CHCH=CH—, —CH=CHCH=N—, and —N=CHCH=CH— are exemplified.

The term "alkynylene optionally containing one or two heteroatom(s)" includes a straight or branched alkynylene group having two to six carbon atoms, optionally containing one or two heteroatom(s) which may be substituted with "alkyl" as described herein. Examples include —C≡CCH$_2$—, —CH$_2$C≡CCH$_2$—, —CH$_2$C≡CCH$_2$O—, —OCH$_2$C≡CH—, —CH$_2$C≡CCH$_2$S—, —SCH$_2$C≡CH—, —CH$_2$C≡CCH$_2$NH—, —NHCH$_2$C≡CH—, —CH$_2$C≡CCH$_2$N(CH$_3$)—, and —N(CH$_3$)CH$_2$C≡CH—. Especially, —CH$_2$C≡CCH$_2$—, and —OCH$_2$C≡CH— are preferred.

The term "3- to 8-membered nitrogen-containing non-aromatic heterocyclic ring" includes a ring of any of the formulas described as such in U.S. Pat. No. 8,143,285, which is incorporated herein by reference in its entirety.

The term "3- to 8-nitrogen-containing aromatic heterocyclic ring" includes a 3- to 8-membered aromatic heterocyclic ring containing one or more of nitrogen atom(s), and further optionally an oxygen atom and/or sulfur atom in the ring. Pyrrolyl (e.g., 1-pyrrolyl, 2-pyrrolyl, 3-pyrrolyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1H-tetrazolyl), oxadiazolyl (e.g., 1,3,4-oxadiazolyl), and thiadiazolyl (e.g., 1,3,4-thiadiazolyl) are exemplified.

The term "4- to 8-membered nitrogen-containing heterocyclic ring containing one or two nitrogen atom(s)" means a ring of any of the formulas described as such in U.S. Pat. No. 8,143,285, which is incorporated herein by reference in its entirety. The term "oxo" refers to an =O group.

"Optionally substituted" is used interchangeably herein with "substituted or unsubstituted."

In the present specification, examples of substituents in "optionally substituted alkyl," "optionally substituted alkyloxy," "optionally substituted alkylthio," "optionally substituted alkylsulfinyl," "optionally substituted alkylsulfonyl," "optionally substituted alkylsulfonyloxy," and "the optionally substituted alkyloxycarbonyl" include cycloalkyl, alkylene optionally containing one or two heteroatom(s), hydroxyl, oxo, alkyloxy optionally substituted with a substituent group A at one to three position(s), mercapto, alkylthio, a halogen atom, nitro, cyano, carboxy, alkyloxycarbonyl, optionally substituted amino, optionally substituted carbamoyl, acyl, aryl optionally substituted with a substituent group B at one to three position(s) (e.g., phenyl), heteroaryl optionally substituted with a substituent group C at one to three position(s) (e.g., pyridyl, furyl, thienyl, imidazolyl, oxazolyl, thiazolyl, pyrazolyl), an optionally substituted non-aromatic heterocyclic ring group which may be substituted with a substituent group C at one to three position(s) (e.g., morpholinyl, pyrrolidinyl, piperazinyl), aryloxy optionally substituted with a substituent group B at one to three position(s) (e.g., phenyloxy), alkylsulfonyl, and the like. These can be substituted with one to three substituent(s) at any possible position.

In the present specification, examples of substituents in "optionally substituted alkenyl," "optionally substituted alkynyl," "optionally substituted alkenyloxy," "optionally substituted alkynyloxy," "optionally substituted alkenylthio," "optionally substituted alkynylthio," "optionally substituted alkenyloxycarbonyl," "optionally substituted alkynyloxycarbonyl," "optionally substituted cycloalkyl," "optionally substituted cycloalkenyl," "optionally substituted cycloalkyloxy, "optionally substituted cycloalkenyloxy," "optionally substituted cycloalkylthio," "optionally substituted cycloalkenylthio," "optionally substituted cycloalkylsulfinyl," "optionally substituted cycloalkenylsulfinyl," "optionally substituted cycloalkylsulfonyl," "optionally substituted cycloalkenylsulfonyl," "optionally substituted cycloalkylssulfonyloxy," "optionally substituted cycloalkenylsulfonyloxy," "optionally substituted alkenyloxycarbonyl," "optionally substituted C1-C6 alkylene," "optionally substituted alkylene," "optionally substituted alkenylene," and "the optionally substituted alkynylene" include alkyl optionally substituted with a substituent group D at one to three position(s), cycloalkyl, alkylene optionally containing one or two heteroatom(s), hydroxyl, oxo, alkyloxy optionally substituted with a substituent group A at one to three position(s), mercapto, alkylthio, a halogen atom, nitro, cyano, carboxy, alkyloxycarbonyl, optionally substituted amino, optionally substituted carbamoyl, acyl, acyloxy, aryl optionally substituted with a substituent group B at one to three position(s) (e.g., phenyl), heteroaryl optionally substituted with a substituent group C at one to three position(s) (e.g., pyridyl, furyl, thienyl, imidazolyl, oxazolyl, thiazolyl, pyrazolyl), non-aromatic heterocyclic group optionally substituted with a substituent group C at one to three position(s) (e.g., morpholinyl, pyrrolidinyl, piperazinyl), aryloxy optionally substituted with a substituent group C at one to three position(s) (e.g., phenyloxy), alkylsulfonyl, and the like. These can be substituted with one or more substituent(s) at any possible position.

In the present specification, examples of substituents in "optionally substituted aryl," "optionally substituted phenoxy," "optionally substituted aryloxy," "optionally substituted phenylthio," "optionally substituted arylthio," "optionally substituted arylsulfinyl," "optionally substituted arylsulfonyl," "optionally substituted arylsulfonyloxy," "optionally substituted heteroaryl," "optionally substituted heteroaryloxy," "optionally substituted heteroarylthio," "optionally substituted heteroarylsulfinyl," "optionally substituted heteroarylsulfonyl," "optionally substituted heteroarylsulfonyloxy," "optionally substituted non-aromatic heterocyclic group," "optionally substituted piperazine-1,4-diyl," "substituted three position(s) (e.g., phenyloxy), alkylsulfonyl, and the like. These can be substituted with one to three substituent(s) at any possible position.

In the present specification, examples of substituents in "optionally substituted alkenyl," "optionally substituted alkynyl," "optionally substituted alkenyloxy," "optionally substituted alkynyloxy," "optionally substituted alkenylthio," "optionally substituted alkynylthio," "optionally substituted alkenyloxycarbonyl," "optionally substituted alkynyloxycarbonyl," "optionally substituted cycloalkyl," "optionally substituted cycloalkenyl," "optionally substituted cycloalkyloxy, "optionally substituted cycloalkenyloxy," "optionally substituted cycloalkylthio," "optionally substituted cycloalkenylthio," "optionally substituted cycloalkylsulfinyl," "optionally substituted cycloalkenylsulfinyl," "optionally substituted cycloalkylsulfonyl," "optionally substituted cycloalkenylsulfonyl," "optionally substituted cycloalkylsulfonyloxy," "optionally substituted cycloalkenylsulfonyloxy," "optionally substituted alkenyloxycarbonyl," "optionally substituted C1-C6 alkylene," "optionally substituted alkylene," "optionally substituted alkenylene," and "the optionally substituted alkynylene" include alkyl optionally substituted with a substituent group D at one to three position(s), cycloalkyl, alkylene optionally containing one or two heteroatom(s), hydroxyl, oxo, alkyloxy optionally substituted with a substituent group A at one to three position(s), mercapto, alkylthio, a halogen atom, nitro, cyano, carboxy, alkyloxycarbonyl, optionally substituted amino, optionally substituted carbamoyl, acyl acyloxy, aryl optionally substituted with a substituent group B at one to three position(s) (e.g., phenyl), heteroaryl optionally substituted with a substituent group C at one to three position(s) (e.g., pyridyl, furyl, thienyl, imidazolyl, oxazolyl, thiazolyl, pyrazolyl), non-aromatic heterocyclic group optionally substituted with a substituent group C at one to three position(s) (e.g., morpholinyl, pyrrolidinyl, piperazinyl), aryloxy optionally substituted with a substituent group C at one to three position(s) (e.g., phenyloxy), alkylsulfonyl, and the like. These can be substituted with one or more substituent(s) at any possible position.

In the present specification, examples of substituents in "optionally substituted aryl," "optionally substituted phenoxy," "optionally substituted aryloxy," "optionally substituted phenylthio," "optionally substituted arylthio," "optionally substituted arylsulfinyl," "optionally substituted arylsulfonyl," "optionally substituted arylsulfonyloxy," "optionally substituted heteroaryl," "optionally substituted heteroaryloxy," "optionally substituted heteroarylthio," "optionally substituted heteroarylsulfinyl," "optionally substituted heteroarylsulfonyl," "optionally substituted heteroarylsulfonyloxy," "optionally substituted non-aromatic heterocyclic group," "optionally substituted piperazine-1,4-diyl," "substituted piperazine-1,4-diyl," "optionally substituted C6 arene-1,4-diamine-$N^1,N^4$-diyl," and substituted C6 arene-1,4-diamine-$N^1,N^4$-diyl," include alkyl optionally substituted with a substituent group D at one to three position(s), cycloalkyl, alkenyl, alkynyl, hydroxyl, alkyloxy optionally substituted with a substituent group A at one to three position(s), aryloxy optionally substituted with a substituent group B at one to three position(s) (e.g., phenoxy), mercapto, alkylthio, a halogen atom, nitro, cyano, carboxy, alkyloxycarbonyl, acyl, alkylsulfonyl, optionally substituted amino, optionally substituted carbamoyl, aryl optionally substituted with a substituent group B at one to three position(s) (e.g., phenyl), heteroaryl optionally substituted with a substituent group C at one to three position(s) (e.g., pyridyl, furyl, thienyl, imidazolyl, oxazolyl, thiazolyl, pyrazolyl), non-aromatic heterocyclic group optionally substituted with a substituent group C at one to three position(s)

(e.g., morpholinyl, pyrrolidinyl, piperazinyl), and the like. These can be substituted with one or more substituent(s) at any possible position.

Substituent group A is comprised of a halogen atom and phenyl optionally substituted with one to three substituent(s) selected from the Substituent group B.

Substituent group B is comprised of a halogen atom, alkyl, alkyloxy, cyano, and nitro.

Substituent group C is comprised of a halogen atom and alkyl.

Substituent group D is comprised of a halogen atom and alkyloxy.

"---" between adjacent atoms indicates a bond that is present or absent depending on the valency of the adjacent atoms in a given specified structural context. The bond may comprise localized electrons between the adjacent atoms or delocalized electrons depending on the given specified structural context.

The carbon between $R^1$ and $L^2$ in Y will have no hydrogens bound thereto when $R^1$ is a divalent moiety (e.g., oxo) and will have one hydrogen bound thereto when $R^1$ is a monovalent moiety (e.g., $N(R^2)_2$, methyl, ethyl, hydroxyl, or halogen).

The available moieties for $A^{10}$, $A^{11}$, $A^{12}$, $A^{13}$, $A^{14}$, $A^{15}$, $A^{16}$, $A^{17}$, $A^{18}$, $A^{20}$, $A^{21}$, $A^{22}$, $A^{23}$, $A^{24}$, $A^{25}$, and $A^{26}$ are understood to be consistent with available valencies depending on a given specified structural context.

It is understood that a specified structural context of the adjacent atom to which $R^2$ is bound may dictate whether only monovalent moieties (e.g., optionally substituted alkyl), only divalent moieties (e.g., oxo), or both divalent and monovalent moieties are available as options for $R^2$. It is also understood that a particular specified monovalent moiety (e.g., optionally substituted alkyl) or divalent moiety (e.g., oxo) for $R^2$ may dictate the remaining valency and bonding pattern of the adjacent atom to which $R^2$ is bound.

In some versions, at least one $R^2$ in each pair of vicinal $R^2$ groups of $A^1$, $A^2$, $A^3$, $A^4$, $A^5$, $A^6$, $A^7$, $A^8$, $A^9$, $A^{10}$, $A^{11}$, $A^{12}$, $A^{13}$, $A^{14}$, $A^{15}$, $A^{16}$, $A^{17}$, $A^{18}$, $A^{19}$, $A^{20}$, $A^{21}$, $A^{22}$, $A^{23}$, $A^{24}$, $A^{25}$, and $A^{26}$, unless explicitly specified otherwise, is a non-cyclic moiety. In some versions, at least one $R^2$ in each pair of vicinal $R^2$ groups of $A^1$, $A^2$, $A^3$, $A^4$, $A^5$, $A^6$, $A^7$, $A^8$, $A^9$, $A^{10}$, $A^{11}$, $A^{12}$, $A^{13}$, $A^{14}$, $A^{15}$, $A^{16}$, $A^{17}$, $A^{18}$, $A^{19}$, $A^{20}$, $A^{21}$, $A^{22}$, $A^{23}$, $A^{24}$, $A^{25}$, and $A^{26}$, unless explicitly specified otherwise, is independently hydrogen, halogen, or optionally substituted C1-C6 alkyl. In some versions, at least one $R^2$ in each pair of vicinal $R^2$ groups of $A^1$, $A^2$, $A^3$, $A^4$, $A^5$, $A^6$, $A^7$, $A^8$, $A^9$, $A^{10}$, $A^{11}$, $A^{12}$, $A^{13}$, $A^{14}$, $A^{15}$, $A^{16}$, $A^{17}$, $A^{18}$, $A^{19}$, $A^{20}$, $A^{21}$, $A^{22}$, $A^{23}$, $A^{24}$, $A^{25}$, and $A^{26}$, unless explicitly specified otherwise, is independently hydrogen or halogen. In some versions, at least one $R^2$ in each pair of vicinal $R^2$ groups of $A^1$, $A^2$, $A^3$, $A^4$, $A^5$, $A^6$, $A^7$, $A^8$, $A^9$, $A^{10}$, $A^{11}$, $A^{12}$, $A^{13}$, $A^{14}$, $A^{15}$, $A^{16}$, $A^{17}$, $A^{18}$, $A^{19}$, $A^{20}$, $A^{21}$, $A^{22}$, $A^{23}$, $A^{24}$, $A^{25}$, and $A^{26}$, unless explicitly specified otherwise, is independently hydrogen. "Vicinal" in this context refers to any two $R^2$ groups bonded to adjacent atoms.

In the course of the methods of the present invention, an effective amount of a compound of the invention can be administered to an animal, including mammals and humans, in many ways. While in the preferred embodiment, the compounds of the invention are administered orally, parenterally, or topically, other forms of administration such as through medical compounds or aerosols are also contemplated. "Effective amount" is used herein to refer to an amount effective to treat a given condition or disease or a given type of condition or disease.

For oral administration, the effective amount of compounds may be administered in, for example, a solid, semi-solid, liquid, or gas state. Specific examples include tablet, capsule, powder, granule, solution, suspension, syrup, and elixir agents. However, the compounds are not limited to these forms.

To formulate the compounds of the invention into tablets, capsules, powders, granules, solutions, or suspensions, the compound is preferably mixed with a binder, a disintegrating agent and/or a lubricant. If necessary, the resultant composition may be mixed with a diluent, a buffer, an infiltrating agent, a preservative and/or a flavor, using known methods. Examples of the binder include crystalline cellulose, cellulose derivatives, cornstarch, cyclodextrins, and gelatin. Examples of the disintegrating agent include cornstarch, potato starch, and sodium carboxymethylcellulose. Examples of the lubricant include talc and magnesium stearate. Further, additives, which have been conventionally used, such as lactose and mannitol, may also be used.

For parenteral administration, the compounds of the present invention may be administered rectally or by injection. For rectal administration, a suppository may be used.

The suppository may be prepared by mixing the compounds of the present invention with a pharmaceutically suitable excipient that melts at body temperature but remains solid at room temperature. Examples include but are not limited to cacao butter, carbon wax, and polyethylene glycol. The resulting composition may be molded into any desired form using methods known to the field.

For administration by injection, the compounds of the present invention may be injected hypodermically, intracutaneously, intravenously, or intramuscularly. Medicinal drugs for such injection may be prepared by dissolving, suspending or emulsifying the compounds of the invention into an aqueous or non-aqueous solvent such as vegetable oil, glyceride of synthetic resin acid, ester of higher fatty acid, or propylene glycol by a known method. If desired, additives such as a solubilizing agent, an osmoregulating agent, an emulsifier, a stabilizer, or a preservative, which has been conventionally used may also be added. While not required, it is preferred that the composition be sterile or sterilized.

To formulate the compounds of the invention into suspensions, syrups, or elixirs, a pharmaceutically suitable solvent may be used. Included among these is the non-limiting example of water.

For topical administration, topical formulations can be in a form of gel, cream, lotion, liquid, emulsion, ointment, spray, solution, suspension, and patches. Inactive ingredients in the topical formulations for example include, but not limited to, lauryl lactate (emollient/permeation enhancer), diethylene glycol monoethylether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent).

The compounds of the invention may also be used together with an additional compound having other pharmaceutically suitable activity to prepare a medicinal drug. A drug, either containing a compound of the invention as a stand-alone compound or as part of a composition, may be used in the treatment of subjects in need thereof.

The compounds of the invention may also be administered in the form of an aerosol or inhalant prepared by charging the compounds in the form of a liquid or fine powder, together with a gaseous or liquid spraying agent and, if necessary, a known auxiliary agent such as an inflating agent, into a non-pressurized container such as an aerosol container or a nebulizer. A pressurized gas of, for example, dichlorofluoromethane, propane or nitrogen may be used as the spraying agent.

The compounds of the invention may be administered to an animal, including mammals and humans, in need thereof as a pharmaceutical composition, such as tablets, capsules, solutions, or emulsions. Administration of other forms of the compounds described in this invention, including but not limited to esters thereof, pharmaceutically suitable salts thereof, metabolites thereof, structurally related compounds thereof, analogs thereof, and combinations thereof, in a single dose or a multiple dose, are also contemplated by the present invention.

The compounds of the invention may also be administered to an animal in need thereof as a nutritional additive, either as a food or nutraceutical supplement. The term "treating" refers to the full or partial reduction of a condition or any aspect, complication, or symptom thereof. Examples include eliminating the condition, reducing the severity of the condition, reducing the number of symptoms or complications of the condition, eliminating a particular symptom or complication of the condition, reducing the severity of one or more symptoms or complications of the condition, or eliciting any other change in the condition of the patient that improves the therapeutic outcome.

The term "preventing" refers to the full or partial prophylaxis of a condition or any aspect, complication or symptom thereof. Examples include prophylactically eliminating the condition, prophylactically reducing the severity of the condition, prophylactically reducing the number of symptoms or complications of the condition, prophylactically eliminating a particular symptom or complication of the condition, prophylactically reducing the severity of one or more symptoms or complications of the condition, or prophylactically eliciting any other change in the condition of the patient that improves the therapeutic outcome.

The compounds described in this invention are preferably used and/or administered in the form of a composition. Suitable compositions are, preferably, a pharmaceutical composition, a foodstuff, or a food supplement. These compositions provide a convenient form in which to deliver the compounds. Compositions of the invention may comprise an antioxidant in an amount effective to increase the stability of the compounds with respect to oxidation or solubility.

The amount of compound that is administered in the method of the invention or that is for administration in the use of the invention is any suitable amount. Examples include from 1 ng/kg body weight to 20 g/kg body weight, such as from 1 µg/kg body weight to 1 g/kg body weight or from 1 mg/kg body weight to 100 mg/kg body weight of compound per day. Suitable compositions can be formulated accordingly. Those of skill in the art of dosing of biologically active agents will be able to develop particular dosing regimens for various subjects based on known and well understood parameters.

A preferred composition according to the invention is a pharmaceutical composition, such as in the form of tablets, pills, capsules, caplets, multiparticulates (including granules, beads, pellets and micro-encapsulated particles), powders, elixirs, syrups, suspensions, and solutions. Pharmaceutical compositions will typically comprise a pharmaceutically acceptable diluent or carrier. Pharmaceutical compositions are preferably adapted for administration parenterally or orally. Orally administrable compositions may be in solid or liquid form and may take the form of tablets, powders, suspensions, and syrups, among other things. Optionally, the compositions comprise one or more flavoring and/or coloring agents. In general, therapeutic and nutritional compositions may comprise any substance that does not significantly interfere with the action of the compounds on the subject.

Pharmaceutically acceptable carriers suitable for use in such compositions are well known in the art of pharmacy. The compositions of the invention may contain 0.01-99% by weight of the compounds of the invention. The compositions of the invention are generally prepared in unit dosage form. Examples of unit dosages of the compounds of the invention include from 0.1 mg to 2000 mg, such as 50 mg to 1000 mg. The excipients used in the preparation of these compositions can include any excipients known in the art.

Further examples of product forms for the composition are food supplements, such as in the form of a soft gel or a hard capsule comprising an encapsulating material selected from the group consisting of gelatin, starch, modified starch, starch derivatives such as glucose, sucrose, lactose, and fructose. The encapsulating material may optionally contain cross-linking or polymerizing agents, stabilizers, antioxidants, light absorbing agents for protecting light-sensitive fills, preservatives, and the like.

In general, the term "carrier" represents a composition with which the compounds described may be mixed, be it a pharmaceutical carrier, foodstuff, nutritional supplement, or dietary aid. The materials described above may be considered carriers for the purposes of the invention. In certain embodiments of the invention, the carrier has little to no biological activity on the compounds of the invention.

Dose: The methods of the present invention can comprise administering a therapeutically effective amount of compound to an animal in need thereof. The effective amount of compound depends on the form of the compound administered, the duration of the administration, the route of administration (e.g., oral or parenteral), the age of the animal, and the condition of the animal, including mammals and humans. Exemplary amounts range from 1 ng/kg/day to 20 g/kg/day, such as 50 µg/kg/day to 5 g/kg/day or 1 to 100 mg/kg/day. The effective amount of compound is most effective in treating or preventing the condition when administered for periods ranging from about 1 to 1000 days or more, such as from 7 to 300 days or from 30 to 90 days. The effective amount of compound may be continued beyond these periods for maintenance of beneficial responses in chronic diseases.

When the effective amount of the compound of the present invention is administered in a nutritional, therapeutic, medical, or veterinary composition, an exemplary dose ranges from about 0.01 to 2.0% wt/wt to the food or nutraceutical product.

In general, the present invention relates to inhibition of inflammation systemically, wherein relevant components include the pancreas, spleen, lung, heart, cardiovascular system, central nervous system, joints, liver, kidneys, immune system, or GI tract. Relevant components in the GI tract include the esophagus, stomach, small intestine, cecum, large intestine, and rectum. The effects result from the exposure of various cells types in the body that induce a biological effect to a compound of the invention. The cells may include those from GI tract tissues, immune cells (i.e., macrophages, monocytes, dendritic cells, neutrophils, lymphocytes), pancreatic islet cells, endothelial cells, neurons, or epithelial cells, among others.

When practiced, the methods of the invention can be by way of administering the compounds to a subject via any acceptable administration route using any acceptable form, as is described above, and allowing the body of the subject to distribute the compounds to the target tissues and cells through natural processes. As is described above, administering can likewise be by direct injection to a site (e.g., organ, tissue) containing a target cell (i.e., a cell to be treated).

The amount to be administered will vary depending on the subject, stage of disease or disorder, age of the subject, general health of the subject, and various other parameters known and routinely taken into consideration by those of skill in the medical arts. As a general matter, a sufficient amount of compound will be administered in order to make a detectable change in the amount of inflammation systemically or in any particular tissue or site in the body. Reduction of inflammation may be related to amount of pain experienced by the subject, insulin, anti-nuclear antigen antibodies, TNFα, or C-reactive protein levels in the blood, the percent of regulatory T-cells in the blood, or concentration of calprotectin in feces.

The methods of the present invention can provide treatments for reducing inflammation by affecting the metabolism of immune cells. The methods can reduce inflammation systemically (i.e., throughout the subject's body) or locally (e.g., at the site of administration or the site of inflammatory cells, including but not limited to T cells and macrophages). In treating or preventing inflammation through immunometabolism, one effect that may be observed is a shift in the metabolism of glucose. In particular, the shift may be from the production of lactate from pyruvate towards the entrance into the tricarboxylic acid cycle that is tied with immunoinflammatory actions. More specifically, this shift in metabolism can be associated with an increase in the proportion of CD4+CD25+FOXP3+ or other regulatory CD4+ T-cells relative to effector CD4+ T-cells such as IL17+ Th17 or IFNγ+ Th1 effector cells. Another observed effect may be decreased cellular proliferation resulting from the combination of decreased anaerobic metabolism and increased immune checkpoint pathways. Another effect of shifts in metabolism triggered therapeutically may be decreased expression of inflammatory chemokines such as MCP-1, IL-8, or CXCL9 resulting from altered processing and storage of fatty acids. The methods can thus also be considered methods of affecting or altering the immune response of a subject to whom the therapy is administered, thereby intercepting inflammation, disease and pathology.

The methods of the present invention can provide methods of reducing inflammation by producing other effects. The methods can reduce inflammation systemically (i.e., throughout the subject's body) or locally (e.g., at the site of administration or the site of inflammatory cells, including but not limited to T cells and macrophages). In treating or preventing inflammation according to the methods of the present invention, one effect that may be seen is the decrease in the number of blood monocytes or macrophages and lymphocytes infiltrating a given tissue. Another may be the increase in regulatory immune cell populations, such as CD4$^+$CD25$^+$FoxP3$^+$ regulatory T-cells, or an increase in regulatory properties of lymphocytes or macrophages (e.g., increased interleukin 4 (IL-4) or IL-10 or decreased TNF-α and IL-6). Another may be the decreased presence of inflammatory genes and/or adhesion molecules. The methods can thus also be considered methods of affecting or altering the immune response of a subject to whom the therapy is administered. The subject may have any condition in which the immunomodulation of T cells or downregulation of cellular adhesion molecules is a desired outcome.

The invention provides methods of treating inflammatory or immune-mediated disease. The inflammatory or immune-mediated disease can include any disease described in Dattatreya et al. 2011 and Shurin et al. 2007, among others.

The invention provides methods of treating autoimmune diseases, such as inflammatory autoimmune diseases, with the compounds described herein. Non-limiting examples of autoimmune diseases include inflammatory bowel disease (IBD) (e.g., Crohn's disease and ulcerative colitis), irritable bowel syndrome (IBS), lupus, systemic lupus erythematosus, rheumatoid arthritis, Sjogren's syndrome, systemic scleroderma, type 1 diabetes, psoriasis (including psoriatic arthritis), autoimmune encephalitis, multiple sclerosis, sarcoidosis, Guillain-Barre syndrome, Grave's disease, antiphospholipid syndrome and cancer-immunotherapy-induced autoimmune diseases, among others. Non-limiting examples of cancer-immunotherapy-induced autoimmune diseases include cancer immunotherapy-induced rheumatic diseases. The invention also provides methods of treating inflammation associated with autoimmune diseases.

The compounds of the invention can be used to treat the symptoms in a subject diagnosed with systemic lupus erythematosus or to prevent the development of disease in a subject genetically predisposed to systemic lupus erythematosus. Symptoms and indications of lupus that may be treated with the invention include but are not limited to lupus nephritis, central nervous system inflammation, headaches, scleritis, optic neuritis, fevers, hardening of the arteries, coronary artery disease, joint pain and malar rash. The invention also provides a method of treating additional forms of lupus including cutaneous lupus (discoid), drug-induced lupus and neonatal lupus.

The compounds of the invention can be used to treat diabetes or conditions resulting therefrom. Exemplary types of diabetes include type 1 diabetes and type 2 diabetes. Exemplary diabetes conditions include diabetic nephropathy, diabetic retinopathy, chronic pain, neuropathy, deep vein thrombosis, or atherosclerosis.

The invention provides methods of treating chronic inflammatory diseases with the compounds described herein. Non-limiting examples of chronic inflammatory diseases includes metabolic syndrome, obesity, prediabetes, cardiovascular disease, type 2 diabetes, non-alcoholic fatty liver disease, non-alcoholic steatohepatitis, cirrhosis, asthma, allergies, chronic granulomatous disease, graft versus host disease, and tumor necrosis factor receptor associated periodic syndrome; muscle wasting, such as amyotrophic lateral sclerosis, Duchenne muscular dystrophy, scoliosis, and progressive muscular atrophy; and others.

The invention provides methods of treating other inflammatory diseases such as acute colonic diverticulitis and radiation-induced inflammation of the gastrointestinal tract with the compounds described herein. Non-limiting examples of radiation-induced inflammation of the gastrointestinal tract include radiation proctitis, radiation enteritis, and radiation proctosigmoiditis.

The invention provides methods of inhibiting inflammation in the GI tract, wherein relevant components of the GI tract can include the stomach, small intestine, large intestine, and rectum.

The invention provides methods of treating an infectious disease with the compounds described herein. Non-limiting examples of such infectious diseases include viral infections, bacterial infections, and fungal infections.

Non-limiting examples of viral infections include infections from viruses in the family adenoviridae, such as adenovirus; viruses in the family herpesviridae such as herpes simplex, type 1, herpes simplex, type 2, varicella-zoster virus, epstein-barr virus, human cytomegalovirus, human herpesvirus, and type 8; viruses in the family papillomaviridae such as human papillomavirus; viruses in the family polyomaviridae such as BK virus and JC virus; viruses in the family poxviridae such as smallpox; viruses in the familyhepadnaviridae such as hepatitis B virus; viruses in the family parvoviridae such as human bocavirus and parvovirus B19; viruses in the family astroviridae such as human astrovirus; viruses in the family caliciviridae such as norwalk virus; viruses in the family picornaviridae such as coxsackievirus, hepatitis A virus, poliovirus, and rhinovirus; viruses in the family coronaviridae such as acute respiratory syndrome virus; viruses in the family flaviviridae such as hepatitis C virus, yellow fever virus, dengue virus, and West Nile virus, viruses in the family togaviridae such as rubella virus; viruses in the family hepeviridae such as hepatitis E virus; viruses in the family retroviridae such as human immunodeficiency virus (HIV); viruses in the family orthomyxoviridae such as influenza virus; viruses in the family arenaviridae such as guanarito virus, junin virus, lassa virus, machupo virus, and sabia virus; viruses in the family bunyaviridae such as Crimean-Congo hemorrhagic fever virus; viruses in the family filoviridae such as ebola virus and marburg virus; COVID-19; viruses in the family paramyxoviridae such as measles virus, mumps virus, parainfluenza virus, respiratory syncytial virus, human metapneumovirus, hendra virus, and nipah virus; viruses in the family rhabdoviridae such as rabies virus; unassigned viruses such as hepatitis D virus; and viruses in the family reoviridae such as rotavirus, orbivirus, coltivirus, and banna virus, among others.

Non-limiting examples of bacterial infections include infections with the bacteria described above, in addition to *Bacillus anthracis, Bacillus cereus, Bordetella pertussis, Borrelia burgdorferi, Brucella abortus, Brucella canis, Brucella melitensis, Brucella suis Campylobacter jejuni Chlamydia pneumoniae, Chlamydia trachomatis, Chlamydophila psittaci, Clostridium botulinum, Clostridium difficile, Clostridium perfringens, Clostridium tetani, Corynebacterium diphtherias, Enterococcus faecalis, Enterococcus faecium, Escherichia coli, Francisella tularensis, Haemophilus influenzae, Helicobacter pylori, Legionella pneumophila, Leptospira interrogans, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae, Yersinia pestis, Yersinia enterocolitica, Yersinia pseudotuberculosis*, and other species from the genera of the above-mentioned organisms.

Non-limiting examples of fungal infections include infection with fungi of the genus *Aspergillus*, such as *Aspergillus fumigatus*, which cause aspergillosis; fungi of the genus *Blastomyces*, such as *Blastomyces dermatitidis*, which cause blastomycosis; fungi of the genus *Candida*, such as *Candida albicans*, which cause candidiasis; fungi of the genus *Coccidioides*, which cause coccidioidomycosis (valley fever); fungi of the genus *Cryptococcus*, such as *Cryptococcus neoformans* and *Cryptococcus gattii*, which cause cryptococcosis; dermatophytes fungi, which cause ringworm; fungi that cause fungal keratitis, such as *Fusarium* species, *Aspergillus* species, and *Candida* species; fungi of the genus *Histoplasma*, such as *Histoplasma capsulatum*, which cause histoplasmosis; fungi of the order *Mucorales*, which cause mucormycosis; fungi of the genus *Saccharomyces*, such as *Saccharomyces cerevisiae*; fungi of the genus *Pneumocystis*, such as *Pneumocystis jirovecii*, which cause *Pneumocystis* pneumonia; and fungi of the genus *Sporothrix*, such as *Sporothrix schenckii*, which cause sporotrichosis.

The invention also provides methods of treating hyperproliferative disorders with the compounds described herein. Hyperproliferative disorders include conditions involving uncontrolled growth of cells, such as cancers or conditions involving the growth of tumors, adenomas, or polyps. Non-limiting examples of hyperproliferative disorders include colorectal cancer, familial adenomatous polyposis (PAP), throat cancer, thyroid cancer, gastric cancer, cancers of the gastrointestinal tract, pancreatic cancer, Hodgkin lymphoma, non-Hodgkin lymphoma, acute myeloid leukemia, hepatocellular cancer, gastrointestinal stromal tumors, acute lymphoblastic leukemia, chronic myeloproliferative disorders, hypereosinophilic syndrome, mastocytosis, among others.

The depiction or definition of any moiety or compound provided herein encompasses any tautomer of the moiety or compound, unless the context clearly dictates otherwise.

The depiction or definition of any moiety or compound provided herein encompasses any salt of the moiety or compound, unless the context clearly dictates otherwise.

The elements, embodiments, versions, and method steps described herein can be used in any compatible combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Molecular Modeling

Example 1

Molecular Modeling of PLXDC2 Ligands

Using previously described ligands of PLXDC2, including PEDF, we determined the existence of high-potential binding sites on the PLXDC2 protein. These ligands were docked onto a homology model of the PLXDC2 receptor to establish important binding residues.

Methods

Virtual Screening. To provide additional insights into preliminary scaffolds, ligand databases were docked onto the PLXDC2 receptor using AutoDock Vina at each of two conformations using cuboid search grid of size (26×28×36 angstrom) to provide predicted binding affinities and conformations of ligands. Binding affinity was normalized to molecular weight of the ligand. Top ligands were selected for further examination of binding pose.

Compound generation. From the identified residues and predicted biochemical interactions, structures were generated for high affinity PLXDC2 ligands. Structures were generated and chemically optimized using WebMo. Structure files were generated in .pdb format and converted to .pdbqt format through calculation of charges by Gasteiger method. Structures were docked using AutoDock Vina to confirm binding affinity.

Analysis. Compounds were preliminarily ranked by lowest predicted binding affinity normalized to molecular weight representing the most favorable binding pose through a minimization of total intermolecular energy, total internal energy and torsional free energy. Compounds were then prioritized based on favorable distances to critical binding residues on PLXDC2.

Results

From the virtual screening of new chemical entities (NCEs), the highest affinity PLXDC2-binding NCEs were largely comprised of compounds with a central 1H-imidazole-2-carboxamide moiety or terminated with a m-phenoxyphenyl group. In general, binding affinities were observed to be increased in compounds that contained a hydrogen bond acceptor group in the Z-group ring structure. The binding affinities of selected family members are provided in FIGS. 1A, 1B, 1C, 1D, and 1E. The predicted binding affinities in the respective lowest energy binding configuration ranged from −10.4 kcal/mol to −12.6 kcal/mol. The highest binding compound in this class of NCEs was observed to be N-(3,5-Dioxo-1,2,4,6,7,7a-hexahydro-1,3a,6-triaza-2-indenyl)-4-(m-phenoxyphenyl)-1H-imidazole-2-carboxamide, termed PX-11. Other compounds with high affinity used a similar backbone but altered Z-groups including PX-04 (N-(1,3-Dihydro-5-isobenzofuranyl)-5-(m-phenoxyphenyl)-1H-imidazole-2-carboxamide), PX-07 (N-(1-Methyl-2-oxo-1H-pyrid-3-yl)-5-(m-phenoxyphenyl)-1H-imidazole-2-carboxamide), and PX-09 (m-[5-(m-Phenoxyphenyl)-1H-imidazol-2-ylcarbonylamino]benzoic acid). Based on binding results and predicted physicochemical properties compounds were selected from this class for synthesis.

Medicinal Chemistry

Example 2

PX-02

Figure 2A:
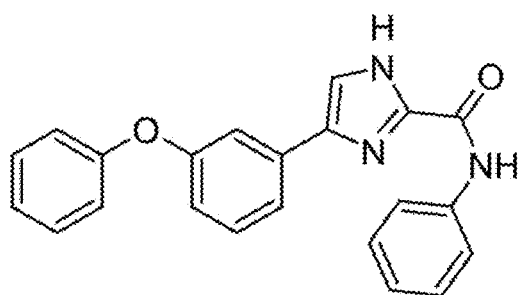
FIGS. 2A-2E. Exemplary compounds of the invention: PX-02 (FIG. 2A); PX-04 (FIG. 2B); PX-07 (FIG. 2C); PX-08 (FIG. 2D); PX-09 (FIG. 2E).

The synthesis of N-Phenyl-4-(m-phenoxyphenyl)-1H-imidazole-2-carboxamide (PX-02, FIG. 2A) was a five-step process as detailed below. To a stirred suspension of sodium hydride in DMF (30 mL), Ethyl 1H-imidazole-2-carboxylate in DMF was added dropwise at 0-5° C. to a stirred suspension of sodium hydride in DMF (30 mL), and stirred at same temperature for 20 min. Then SEM-Cl was added dropwise over a period of 5 min, and was stirred for 24 h at room temperature. The reaction mass was diluted with ice cold water. Product was extracted with ethyl acetate twice. The combined organic layers were washed twice with cold water and brine, dried over $Na_2SO_4$, filtered and concentrated under reduced pressure to get ethyl 1-{[2-(trimethyl silyl) ethoxy]methyl}-1H-imidazole-2-carboxylate.

N-Bromosuccinimide in DMF was added to a stirred solution of ethyl 1-{[2-(trimethylsilyl)ethoxy]methyl}-1H-imidazole-2-carboxylate in DMF at 0-5° C. The resulting reaction mixture was stirred at room temperature for 16 h. The reaction mixture was poured in ice cold water and product was extracted thrice with ethyl acetate. The combined organic layer was washed with saturated $NaHCO_3$ solution, brine, and water. Product was dried over $Na_2SO_4$, filtered and concentrated under reduced pressure to get crude. The obtained crude was purified by chromatography. The column fractions were combined and concentrated under reduced pressure to afford ethyl 4-bromo-3-{[2-(trimethylsilyl)ethoxy]methyl}-3H-imidazole-2-carboxylate.

3-Phenoxyphenylboronic acid was added to a stirred solution of ethyl 4-bromo-3-{[2-(trimethylsilyl)ethoxy]methyl}-3H-imidazole-2-carboxylate in toluene:water [9:1], with $K_3PO_4$. The reaction mixture was degassed for 10 min. $P(Cy)_3$ and $Pd(OAc)_2$ were added and again degassed for 10 min. The reaction mixture was stirred at 120° C. for 16 h. The reaction mixture was cooled to room temperature and directly concentrated under reduced pressure to get crude. The crude was purified by chromatography. Pure fractions were combined and concentrated under reduced pressure to afford ethyl 5-(m-phenoxyphenyl)-1-{[2-(trimethylsilypethoxy]methyl}-1H-imidazole-2-carboxylate.

Phenylamine, triethylamine, and $Me_3Al$ (in toluene) were charged to a stirred solution of 5-(m-Phenoxyphenyl)-1-{[2-(trimethylsilyl)ethoxy]methyl}-1H-imidazole-2-carboxylate in toluene at 0° C. Temperature was raised to 120° C. over 8 h. The organic layer was twice washed with water and brine. The resulting mixture was dried over $Na_2SO_4$, filtered, and concentrated under reduced pressure to obtain crude material. The obtained crude material was purified by chromatography. Combined column fractions were concentrated under reduced pressure to afford N-Phenyl-4-(m-phenoxyphenyl)-1-{[2-(trimethylsilyl)ethoxy]methyl}-1H-imidazole-2-carboxamide.

HCl [4.0 N] was added to a stirred solution of N-Phenyl-4-(m-phenoxyphenyl)-1-{[2-(trimethylsilypethoxy]methyl}-1H-imidazole-2-carboxamide in 1,4 dioxane at 0° C. under nitrogen atmosphere. The resulting reaction mixture was stirred at 90° C. for 4 h. The reaction mixture was concentrated under reduced pressure to get crude. The crude was purified by chromatography. Pure fractions were collected and concentrated under reduced pressure to afford PX-02 (N-Phenyl-4-(m-phenoxyphenyl)-1H-imidazole-2-carboxamide) as off-white solid (HCl salt).

Example 3

PX-04

Figure 2B:
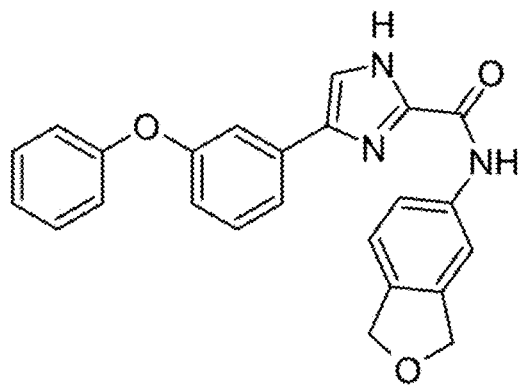

The synthesis of N-(1,3-Dihydro-5-isobenzofuranyl)-5-(m-phenoxyphenyl)-1H-imidazole-2-carboxamide (PX-04, FIG. 2B) was a six-step process as detailed below.

To a stirred suspension of sodium hydride in DMF (30 mL), Ethyl 1H-imidazole-2-carboxylate in DMF was added dropwise at 0-5° C. to a stirred suspension of sodium hydride in DMF (30 mL), and stirred at same temperature for 20 min. Then SEM-Cl was added dropwise over a period of 5 min, and was stirred for 24 h at room temperature. The reaction mass was diluted with ice cold water. Product was extracted with ethyl acetate twice. The combined organic layers were washed twice with cold water and brine, dried over Na$_2$SO$_4$, filtered and concentrated under reduced pressure to get ethyl 1-{[2-(trimethyl silyl)ethoxy]methyl}-1H-imidazole-2-carboxylate.

N-Bromosuccinimide in DMF was added to a stirred solution of ethyl 1-{[2-(trimethylsilyl)ethoxy]methyl}-1H-imidazole-2-carboxylate in DMF at 0-5° C. The resulting reaction mixture was stirred at room temperature for 16 h. The reaction mixture was poured in ice cold water and product was extracted thrice with ethyl acetate. The combined organic layer was washed with saturated NaHCO$_3$ solution, brine, and water. Product was dried over Na$_2$SO$_4$, filtered and concentrated under reduced pressure to get crude. The obtained crude was purified by chromatography. The column fractions were combined and concentrated under reduced pressure to afford ethyl 4-bromo-3-{[2-(trimethylsilyl)ethoxy]methyl}-3H-imidazole-2-carboxylate.

3-Phenoxyphenylboronic acid was added to a stirred solution of ethyl 4-bromo-3-{[2-(trimethylsilyl)ethoxy]methyl}-3H-imidazole-2-carboxylate in toluene:water [9:1], with K$_3$PO$_4$. The reaction mixture was degassed for 10 min. P(Cy)$_3$ and Pd(OAc)$_2$ were added and again degassed for 10 min. The reaction mixture was stirred at 120° C. for 16 h. The reaction mixture was cooled to room temperature and directly concentrated under reduced pressure to get crude. The crude was purified by chromatography. Pure fractions were combined and concentrated under reduced pressure to afford ethyl 5-(m-phenoxyphenyl)-1-{[2-(trimethylsilypethoxy]methyl}-1H-imidazole-2-carboxylate.

LiOH.H$_2$O was added to a stirred solution of ethyl 5-(m-phenoxyphenyl)-1-{[2-(trimethylsilyl)ethoxy]methyl}-1H-imidazole-2-carboxylate in THF:H2O [1:1] at room temperature. The resulting reaction mixture was stirred at room temperature for 24 h. The reaction mixture was directly concentrated under reduced pressure to obtain crude material. The obtained crude material was diluted with water, and twice extracted with MTBE, dried over Na$_2$SO$_4$, filtered and concentrated under reduced pressure to afford 5-(m-Phenoxyphenyl)-1-{[2-(trimethylsilyl)ethoxy]methyl}-1H-imidazole-2-carboxylic acid as a lithium salt.

1,3-Dihydroisobenzofuran-5-amine, triethylamine, and T3P (50% in EtOAc) were charged to a stirred solution of 5-(m-Phenoxyphenyl)-1-{[2-(trimethylsilyl)ethoxy]methyl}-1H-imidazole-2-carboxylic acid (lithium salt) in CH$_2$Cl$_2$ at room temperature under argon atmosphere. The reaction mixture was stirred for 16 h and diluted with CH$_2$Cl$_2$. The organic layer was twice washed with water and brine. The resulting mixture was dried over Na$_2$SO$_4$, filtered, and concentrated under reduced pressure to obtain crude material. The obtained crude material was purified by chromatography. Combined column fractions were concentrated under reduced pressure to afford N-(1,3-Dihydro-5-isobenzofuranyl)-5-(m-phenoxyphenyl)-1-{[2-(trimethyl silyl)ethoxy]methyl}-1H-imidazole-2-carboxamide.

HCl [4.0 M in dioxane] was added to a stirred solution of N-(1,3-Dihydro-5-isobenzofuranyl)-5-(m-phenoxyphenyl)-1-{[2-(trimethyl silyl)ethoxy]methyl}-1H-imidazole-2-carboxamide in 1,4 dioxane at 0° C. under nitrogen atmosphere. The resulting reaction mixture was stirred at 50° C. for 24 h. The reaction mixture was concentrated under reduced pressure to get crude. The crude was purified by chromatography. The desired product was eluted with 70% acetonitrile in water, pure fractions were collected and concentrated under reduced pressure to afford PX-04 (N-(1,3-Dihydro-5-isobenzofuranyl)-5-(m-phenoxyphenyl)-1H-imidazole-2-carboxamide) as off-white solid (HCl salt). $^1$H NMR (400 MHz, DMSO-d$_6$): δ 13.06 (s, 1H), 9.89 (s, 1H), 7.77 (s, 2H), 7.68-7.63 (m, 3H), 7.39-7.35 (m, 3H), 7.25 (d, J=8.0 Hz, 1H), 7.13-7.09 (m, 1H), 7.03-7.01 (m, 2H), 6.92-6.86 (m, 1H), 4.98 (d, J=9.6 Hz, 4H).

Example 4

PX-07

Figure 2C:
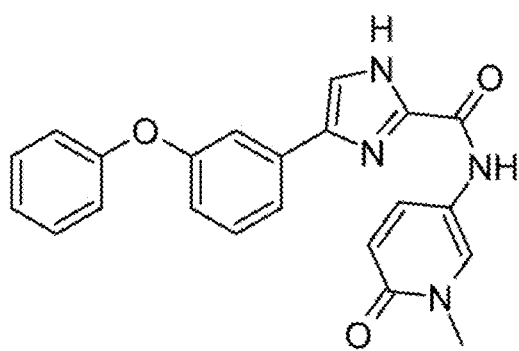

The synthesis of N-(1-Methyl-2-oxo-1H-pyrid-3-yl)-5-(m-phenoxyphenyl)-1H-imidazole-2-carboxamide (PX-07, FIG. 2C) was a five-step process as detailed below.

To a stirred suspension of sodium hydride in DMF (30 mL), Ethyl 1H-imidazole-2-carboxylate in DMF was added dropwise at 0-5° C. to a stirred suspension of sodium hydride in DMF (30 mL), and stirred at same temperature for 20 min. Then SEM-Cl was added dropwise over a period of 5 min, and was stirred for 24 h at room temperature. The reaction mass was diluted with ice cold water. Product was extracted with ethyl acetate twice. The combined organic layers were washed twice with cold water and brine, dried over Na$_2$SO$_4$, filtered and concentrated under reduced pressure to get ethyl 1-{[2-(trimethylsilyl)ethoxy]methyl}-1H-imidazole-2-carboxylate.

N-Bromosuccinimide in DMF was added to a stirred solution of ethyl 1-{[2-(trimethylsilyl)ethoxy]methyl}-1H-imidazole-2-carboxylate in DMF at 0-5° C. The resulting reaction mixture was stirred at room temperature for 16 h. The reaction mixture was poured in ice cold water and product was extracted thrice with ethyl acetate. The combined organic layer was washed with saturated NaHCO$_3$ solution, brine, and water. Product was dried over Na$_2$SO$_4$, filtered and concentrated under reduced pressure to get crude. The obtained crude was purified by chromatography. The column fractions were combined and concentrated under reduced pressure to afford ethyl 4-bromo-3-{[2-(trimethylsilyl)ethoxy]methyl}-3H-imidazole-2-carboxylate.

3-Phenoxyphenylboronic acid was added to a stirred solution of ethyl 4-bromo-3-{[2-(trimethylsilyl)ethoxy]methyl}-3H-imidazole-2-carboxylate in toluene:water [9:1], with K$_3$PO$_4$. The reaction mixture was degassed for 10 min. P(Cy)$_3$ and Pd(OAc)$_2$ were added and again degassed for 10 min. The reaction mixture was stirred at 120° C. for 16 h. The reaction mixture was cooled to room temperature and directly concentrated under reduced pressure to get crude. The crude was purified by chromatography. Pure fractions were combined and concentrated under reduced pressure to afford ethyl 5-(m-phenoxyphenyl)-1-{[2-(trimethylsilypethoxy]methyl}-1H-imidazole-2-carboxylate.

3-Amino-1-methylpyridin-2(1H)-one, triethylamine, and Me$_3$Al (in toluene) were charged to a stirred solution of 5-(m-Phenoxyphenyl)-1-{[2-(trimethylsilyl)ethoxy]methyl}-1H-imidazole-2-carboxylate in toluene at 0° C. Temperature was raised to 120° C. over 8 h.

The organic layer was twice washed with water and brine. The resulting mixture was dried over Na$_2$SO$_4$, filtered, and concentrated under reduced pressure to obtain crude material. The obtained crude material was purified by chromatography. Combined column fractions were concentrated under reduced pressure to afford N-(1-Methyl-2-oxo-1H-pyrid-3-yl)-5-(m-phenoxyphenyl)-1-{[2-(trimethyl silyl)ethoxy]methyl}-1H-imidazole-2-carboxamide.

HCl [4.0 N] was added to a stirred solution of N-(1-Methyl-2-oxo-1H-pyrid-3-yl)-5-(m-phenoxyphenyl)-1-{[2-(trimethylsilyl)ethoxy]methyl}-1H-imidazole-2-carboxamide in 1,4 dioxane at 0° C. under nitrogen atmosphere. The resulting reaction mixture was stirred at 90° C. for 4 h. The reaction mixture was concentrated under reduced pressure to get crude. The crude was purified by chromatography. Pure fractions were collected and concentrated under reduced pressure to afford PX-07 (N-(1-Methyl-2-oxo-1H-pyrid-3-yl)-5-(m-phenoxyphenyl)-1H-imidazole-2-carboxamide) as off-white solid (HCl salt). $^1$H NMR (400 MHz, DMSO-d$_6$): δ 13.59 (s, 1H), 9.89 (s, 1H), 8.31 (m, 1H), 7.98 (s, 1H), 7.70-7.66 (d, J=8.0 Hz, 1H), 7.56 (s, 1H), 7.49-7.33 (m, 4H), 7.13-7.09 (m, 1H), 7.03-7.01 (m, 2H), 6.92-6.86 (m, 1H), 3.56 (s, 3H).

Example 5

PX-08

Figure 2D:
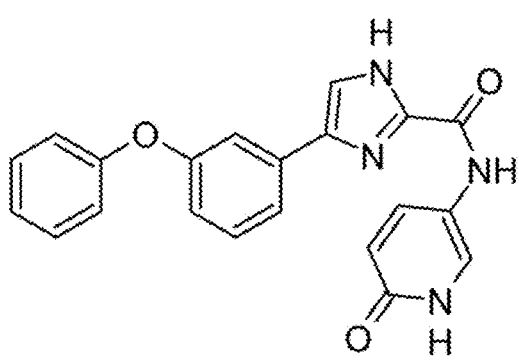

The synthesis of N-(2-Oxo-1H-pyrid-3-yl)-5-(m-phenoxyphenyl)-1H-imidazole-2-carboxamide (PX-08, FIG. 2D) was a five-step process as detailed below. To a stirred suspension of sodium hydride in DMF (30 mL), Ethyl 1H-imidazole-2-carboxylate in DMF was added dropwise at 0-5° C. to a stirred suspension of sodium hydride in DMF (30 mL), and stirred at same temperature for 20 min. Then SEM-Cl was added dropwise over a period of 5 min, and was stirred for 24 h at room temperature. The reaction mass was diluted with ice cold water. Product was extracted with ethyl acetate twice. The combined organic layers were washed twice with cold water and brine, dried over Na$_2$SO$_4$, filtered and concentrated under reduced pressure to get ethyl 1-{[2-(trimethyl silyl)ethoxy]methyl}-1H-imidazole-2-carboxylate.

N-Bromosuccinimide in DMF was added to a stirred solution of ethyl 1-{[2-(trimethylsilyl)ethoxy]methyl}-1H-imidazole-2-carboxylate in DMF at 0-5° C. The resulting reaction mixture was stirred at room temperature for 16 h. The reaction mixture was poured in ice cold water and product was extracted thrice with ethyl acetate. The combined organic layer was washed with saturated NaHCO$_3$ solution, brine, and water. Product was dried over Na$_2$SO$_4$, filtered and concentrated under reduced pressure to get crude. The obtained crude was purified by chromatography. The column fractions were combined and concentrated under reduced pressure to afford ethyl 4-bromo-3-{[2-(trimethylsilyl)ethoxy]methyl}-3H-imidazole-2-carboxylate.

3-Phenoxyphenylboronic acid was added to a stirred solution of ethyl 4-bromo-3-{[2-(trimethylsilyl)ethoxy]methyl}-3H-imidazole-2-carboxylate in toluene:water [9:1], with K$_3$PO$_4$. The reaction mixture was degassed for 10 min. P(Cy)$_3$ and Pd(OAc)$_2$ were added and again degassed for 10 min. The reaction mixture was stirred at 120° C. for 16 h. The reaction mixture was cooled to room temperature and directly concentrated under reduced pressure to get crude. The crude was purified by chromatography. Pure fractions were combined and concentrated under reduced pressure to afford ethyl 5-(m-phenoxyphenyl)-1-{[2-(trimethylsilypethoxy]methyl}-1H-imidazole-2-carboxylate.

3-Amino-2-hydroxypyridine, triethylamine, and Me$_3$Al (in toluene) were charged to a stirred solution of 5-(m-Phenoxyphenyl)-1-{[2-(trimethylsilyl)ethoxy]methyl}-1H-imidazole-2-carboxylate in toluene at 0° C. Temperature was raised to 120° C. over 8 h. The organic layer was twice washed with water and brine. The resulting mixture was dried over Na$_2$SO$_4$, filtered, and concentrated under reduced pressure to obtain crude material. The obtained crude material was purified by chromatography. Combined column fractions were concentrated under reduced pressure to afford N-(2-Oxo-1H-pyrid-3-yl)-5-(m-phenoxyphenyl)-1-{[2-(trimethyl silyl)ethoxy]methyl}-1H-imidazole-2-carboxamide.

HCl [4.0 N] was added to a stirred solution of N-(2-Oxo-1H-pyrid-3-yl)-5-(m-phenoxyphenyl)-1-{[2-(trimethyl silyl)ethoxy]methyl}-1H-imidazole-2-carboxamide in 1,4 dioxane at 0° C. under nitrogen atmosphere. The resulting reaction mixture was stirred at 100° C. for 3 h. The reaction mixture was concentrated under reduced pressure to get crude. The crude was purified by chromatography. Pure fractions were collected and concentrated under reduced pressure to afford PX-07 (N-(2-Oxo-1H-pyrid-3-yl)-5-(m-phenoxyphenyl)-1H-imidazole-2-carboxamide) as off-white solid (HCl salt). $^1$H NMR (400 MHz, DMSO-d$_6$): δ 13.72-13.41 (m, 1H), 12.28-12.04 (m, 1H), 9.82 (s, 1H), 8.33 (m, 1H), 7.98 (s, 1H), 7.69-7.64 (m, 1H), 7.55 (s, 1H), 7.44-7.36 (m, 3H), 7.17-7.09 (m, 2H), 7.06-7.02 (m, 2H), 6.91-6.85 (m, 1H), 6.34-6.27 (m, 1H).

Example 6

PX-09

Figure 2E:
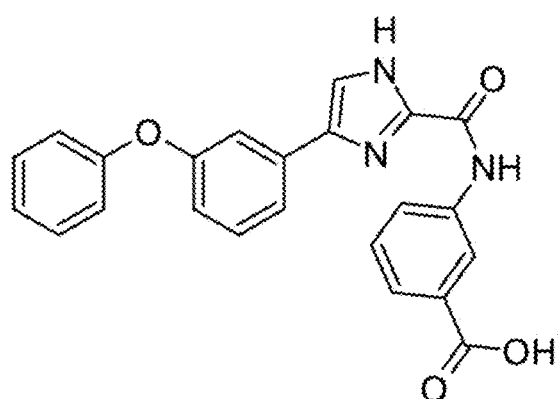

The synthesis of m-[5-(m-Phenoxyphenyl)-1H-imidazol-2-ylcarbonylamino]benzoic acid (PX-09, FIG. 2E) was a six-step process as detailed below.

To a stirred suspension of sodium hydride in DMF (30 mL), Ethyl 1H-imidazole-2-carboxylate in DMF was added dropwise at 0-5° C. to a stirred suspension of sodium hydride in DMF (30 mL), and stirred at same temperature for 20 min. Then SEM-Cl was added dropwise over a period of 5 min, and was stirred for 24 h at room temperature. The reaction mass was diluted with ice cold water. Product was extracted with ethyl acetate twice. The combined organic layers were washed twice with cold water and brine, dried over Na$_2$SO$_4$, filtered and concentrated under reduced pressure to get ethyl 1-{[2-(trimethyl silyl)ethoxy]methyl}-1H-imidazole-2-carboxylate.

N-Bromosuccinimide in DMF was added to a stirred solution of ethyl 1-{[2-(trimethylsilyl)ethoxy]methyl}-1H-imidazole-2-carboxylate in DMF at 0-5° C. The resulting reaction mixture was stirred at room temperature for 16 h. The reaction mixture was poured in ice cold water and product was extracted thrice with ethyl acetate. The combined organic layer was washed with saturated NaHCO$_3$ solution, brine, and water. Product was dried over Na$_2$SO$_4$, filtered and concentrated under reduced pressure to get crude. The obtained crude was purified by chromatography. The column fractions were combined and concentrated under reduced pressure to afford ethyl 4-bromo-3-{[2-(trimethylsilyl)ethoxy]methyl}-3H-imidazole-2-carboxylate.

3-Phenoxyphenylboronic acid was added to a stirred solution of ethyl 4-bromo-3-{[2-(trimethylsilyl)ethoxy]methyl}-3H-imidazole-2-carboxylate in toluene:water [9:1], with K$_3$PO$_4$. The reaction mixture was degassed for 10 min. P(Cy)$_3$ and Pd(OAc)$_2$ were added and again degassed for 10 min. The reaction mixture was stirred at 120° C. for 16 h. The reaction mixture was cooled to room temperature and directly concentrated under reduced pressure to get crude. The crude was purified by chromatography. Pure fractions were combined and concentrated under reduced pressure to afford ethyl 5-(m-phenoxyphenyl)-1-{[2-(trimethylsilypethoxy]methyl}-1H-imidazole-2-carboxylate.

LiOH.H$_2$O was added to a stirred solution of ethyl 5-(m-phenoxyphenyl)-1-{[2-trimethylsilyl)ethoxy]methyl}-1H-imidazole-2-carboxylate in THF:H$_2$O [1:1] at room temperature. The resulting reaction mixture was stirred at room temperature for 24 h. The reaction mixture was directly concentrated under reduced pressure to obtain crude material. The obtained crude material was diluted with water, and twice extracted with MTBE, dried over $Na_2SO_4$, filtered and concentrated under reduced pressure to afford 5-(m-Phenoxyphenyl)-1-{[2-(trimethylsilyl)ethoxy]methyl}-1H-imidazole-2-carboxylic acid as a lithium salt.

1,3-Dihydroisobenzofuran-5-amine, triethylamine, and T3P (50% in EtOAc) were charged to a stirred solution of 5-(m-Phenoxyphenyl)-1-{[2-(trimethylsilyl)ethoxy]methyl}-1H-imidazole-2-carboxylic acid (lithium salt) in $CH_2Cl_2$ at room temperature under argon atmosphere. The reaction mixture was stirred for 16 h and diluted with $CH_2Cl_2$. The organic layer was washed with $NaHCO_3$ twice washed with water and brine. The resulting mixture was dried over $Na_2SO_4$, filtered, and concentrated under reduced pressure to obtain crude material. The obtained crude material was purified by chromatography. Combined column fractions were concentrated under reduced pressure to afford Methyl m-[5-(m-phenoxyphenyl)-1-{[2-(trimethyl silyl)ethoxy]methyl}-1H-imidazol-2-ylcarbonylamino]benzoate.

Methyl m-[5-(m-phenoxyphenyl)-1-{[2-(trimethyl silyl)ethoxy]methyl}-1H-imidazol-2-ylcarbonylamino]benzoate in 1,4 dioxane was charged with Con.HCl at room temperature. The resultant reaction mixture was stirred at 110° C. under nitrogen atmosphere. The reaction mixture was concentrated under reduced pressure to get crude. The crude was purified by chromatography. Pure fractions were collected and concentrated under reduced pressure to afford PX-09 (m-[5-(m-Phenoxyphenyl)-1H-imidazol-2-ylcarbonylamino]benzoic acid) as off-white solid (HCl salt). $^1H$ NMR (400 MHz, DMSO-$d_6$): δ 8.74 (s, 1H), 8.68 (s, 2H), 8.26 (s, 1H), 8.21 (dd, J=8.8, 1.6 Hz, 1H), 7.93 (d, J=8.8 Hz, 1H), 7.63 (d, J=1.6 Hz, 1H), 7.35 (d, J=8.4 Hz, 1H), 7.05 (dd, J=8.0, 1.6 Hz, 1H), 6.91 (brs, 2H), 4.63 (t, J=8 Hz, 2H), 3.19 (t, J=8 Hz, 2H).

Experimental Studies

Example 7

Immunological Screening In Vitro in CD4+ T Cells
Introduction

CD4+ T cells are central to the pathogenesis of many autoimmune diseases and the amplification of inflammatory responses that can contribute to organ damage. As such, the trafficking and differentiation of these cells is an effective option for the treatment of symptoms and prevention of flares in autoimmune disease. With the loss of PLXDC2, CD4+ T cells produced greater amounts of IFNγ and TNFα and have a higher likelihood of differentiating into inflammatory/effector subsets, such as Th17 and Th1.
Methods Cell culture. Spleens were excised from C57BL/6 mice. Spleens were crushed between the frosted ends of microscope slides and filtered to provide a cellular suspension. Red blood cells were lysed through hypotonic lysis. Remaining cells were washed and filtered. CD4+ T cells were enriched within the suspension using magnetic sorting based negative selection. Cells were collected and plated within 96 well plates coated with anti-CD3/CD28 and cultured in the presence of PX-02, PX-04, PX-07, PX-08 and PX-09 at 0, 0.1 or 1 micromolar for 24 h. During the last 6 h of culture, cells were stimulated with phorbol 12-myristate-13-acetate (PMA) and ionomycin.

Figure 3A:
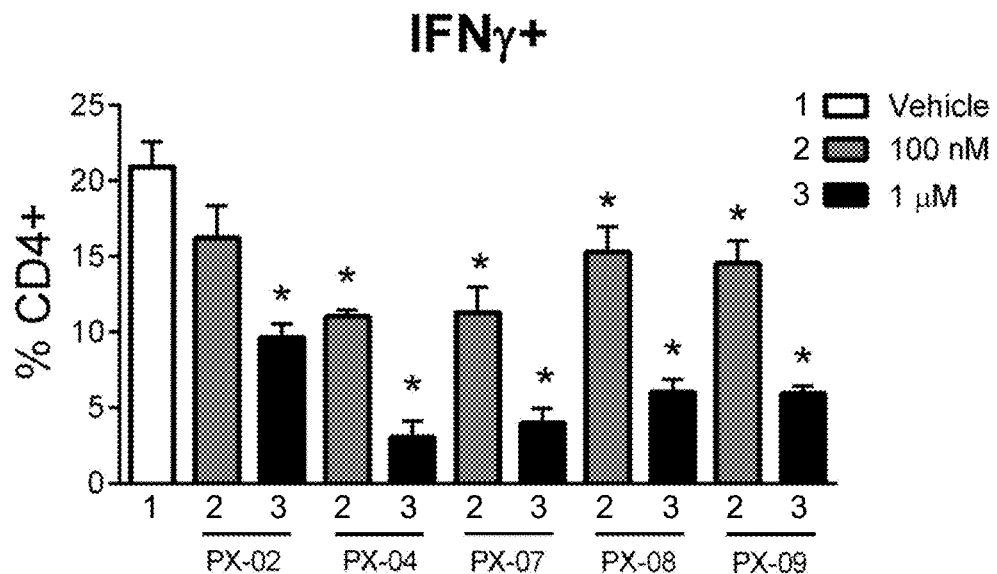
FIGS. 3A and 3B. Immunological validation of PX-02, PX-04, PX-07, PX-08, and PX-09 activity in CD4+ T cells. Percentages of IFNγ+ (FIG. 3A) and TNFα+ (FIG. 3B) CD4+ T cells were measured by flow cytometry after in vitro treatment of cells with PX compounds at concentrations of 0.1 and 1 micromolar. Statistical significance (P<0.05) is marked by asterisks.
Figure 3B:
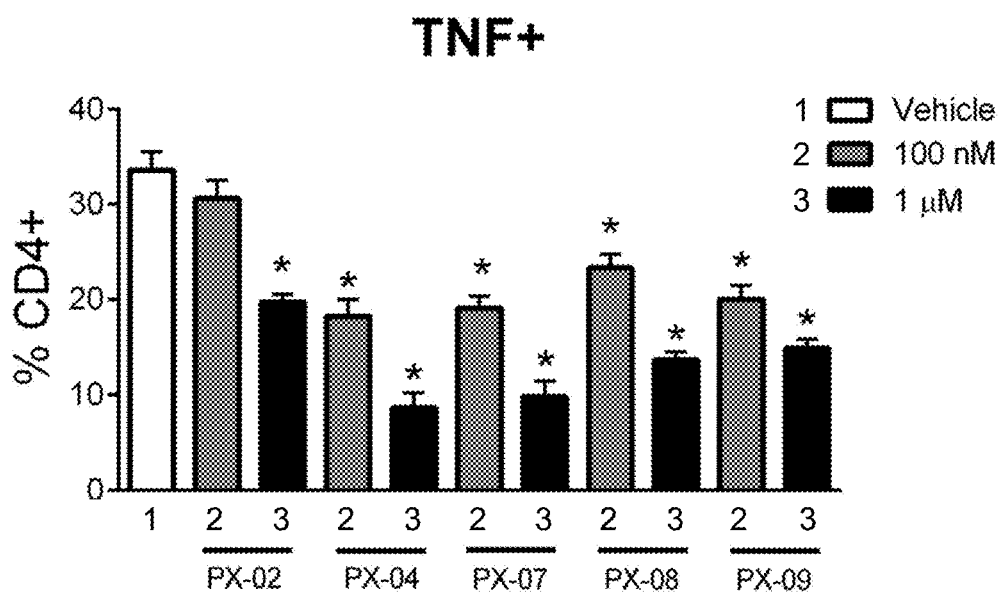

Immunological analysis. Cells were collected from 96 well plates and stained with a cocktail of antibodies for immunophenotyping by flow cytometry. Culture supernatant was collected and assayed for cytokine concentrations by cytometric bead array. Data was captured on a BD FACS Celesta and analyzed using FACSDiva.
Results The five tested PLXDC2 ligands all decreased production of IFNγ (FIG. 3A) and TNFα (FIG. 3B) in CD4+ T cell culture. PX-04 and PX-07 were observed to have the largest magnitude of response, providing an approximate 55% reduction at 100 nM and 80% reduction at 1 μM in IFNγ production. With the exception of PX-02, which only induced significant changes at 1 μM, the remaining compounds (PX-04, PX-07, PX-08, and PX-09) tested provided a significant decrease at both tested concentrations relative to vehicle treated control.

Figure 4A:
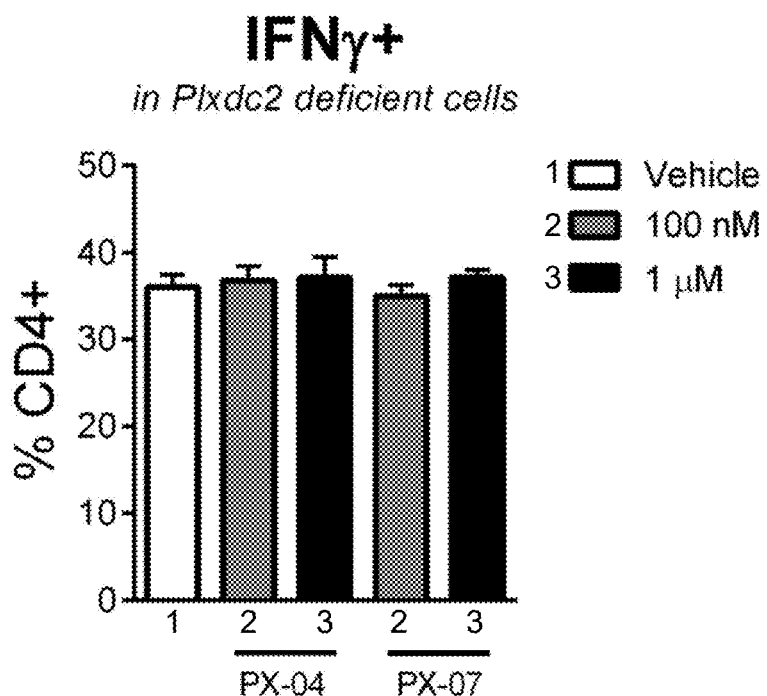
FIGS. 4A and 4B. Immunological validation of PX-04 and PX-07 specificity in CD4+ T cells. Percentages of IFNγ+(FIG. 4A) and TNFα+ (FIG. 4B) CD4+ T cells deficient in PLXDC2 were measured by flow cytometry after in vitro treatment of cells with PX compounds at concentrations of 0.1 and 1 micromolar. Statistical significance (P<0.05) is marked by asterisks.
Figure 4B:
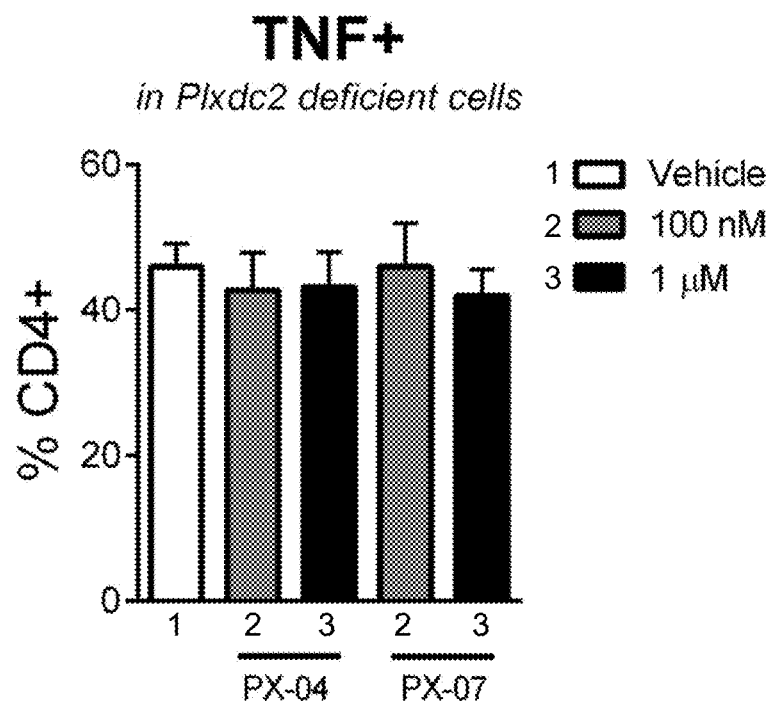

To determine the specificity of response to the PLXDC2 receptor, PX-04 and PX-07 were tested further in PLXDC2 deficient cells. In the absence of PLXDC2, no difference from vehicle was noted in IFNγ (FIG. 4A) and TNFα (FIG. 4B) at either 100 nM or 1 μM.

Example 8

Immunological Screening In Vitro in Bone Marrow-Derived Macrophages (BMDM)

Introduction

Figure 5A:
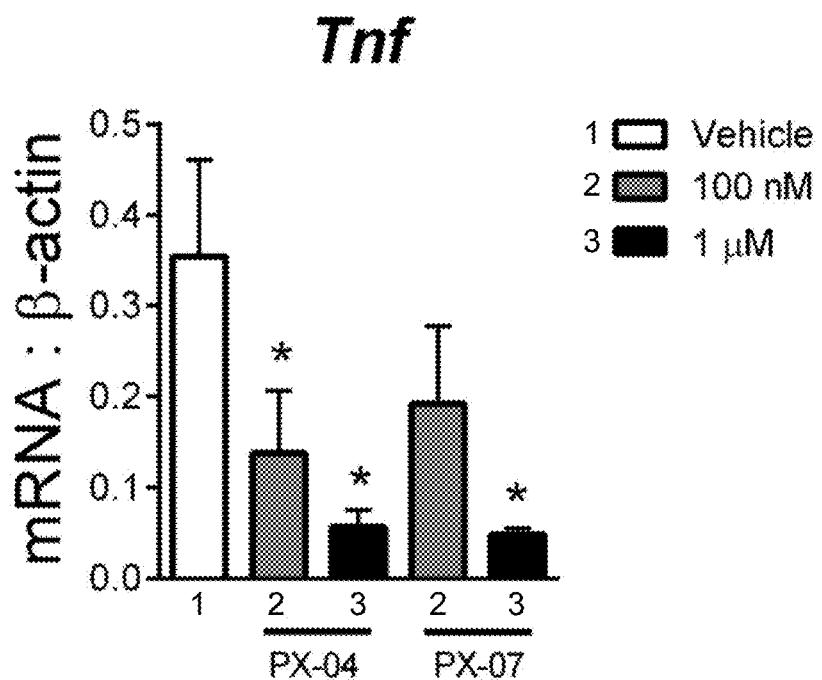
FIGS. 5A and 5B. Gene expression following PX-04 and PX-07 treatment of bone marrow-derived macrophages (BMDMs). Measurement of Tnf (FIG. 5A) and Il10 (FIG. 5B) by quantitative real-time PCR from BMDMs challenged with lipopolysaccharide for 2 hours and treated with vehicle, PX-04, or PX-07 at 0.1 and 1 micromolar. Data is normalized to beta-actin. Statistical significance (P<0.05) is marked by asterisks.
Figure 5B:
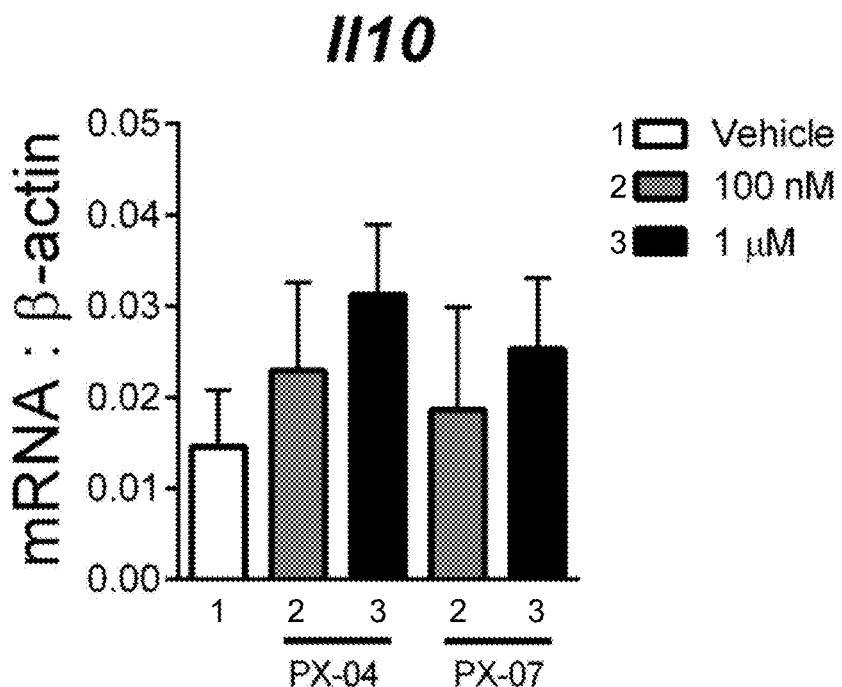
Figure 6A:
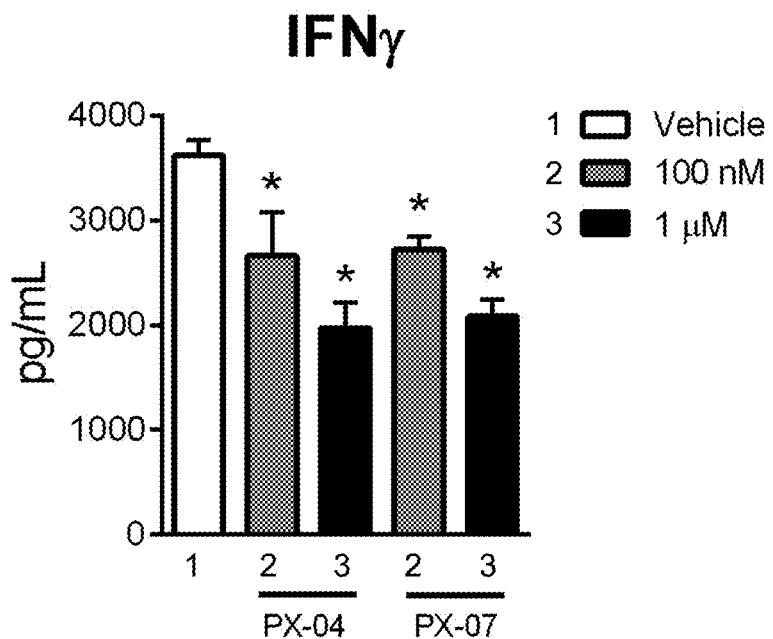
FIGS. 6A-6D. Cytokine production following PX-04 and PX-07 treatment of bone marrow-derived macrophages (BMDMs). Measurement of IFNγ (FIG. 6A), IL-6 (FIG. 6B), TNF (FIG. 6C) and IL-10 (FIG. 6D) by Luminex assay from supernatant of BMDMs challenged with lipopolysaccharide for 6 hours and treated with vehicle, PX-04, or PX-07 at 0.1 and 1 micromolar. Statistical significance (P<0.05) is marked by asterisks.
Figure 6B:
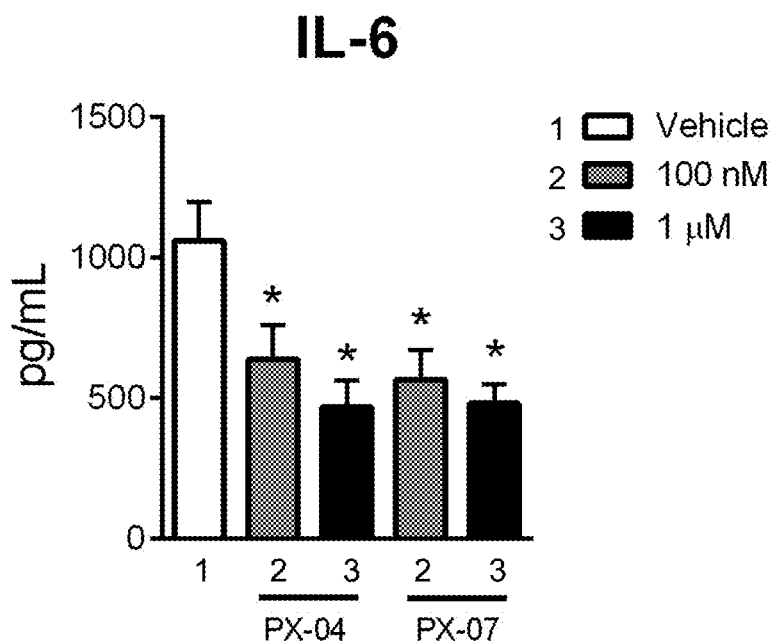
Figure 6D:
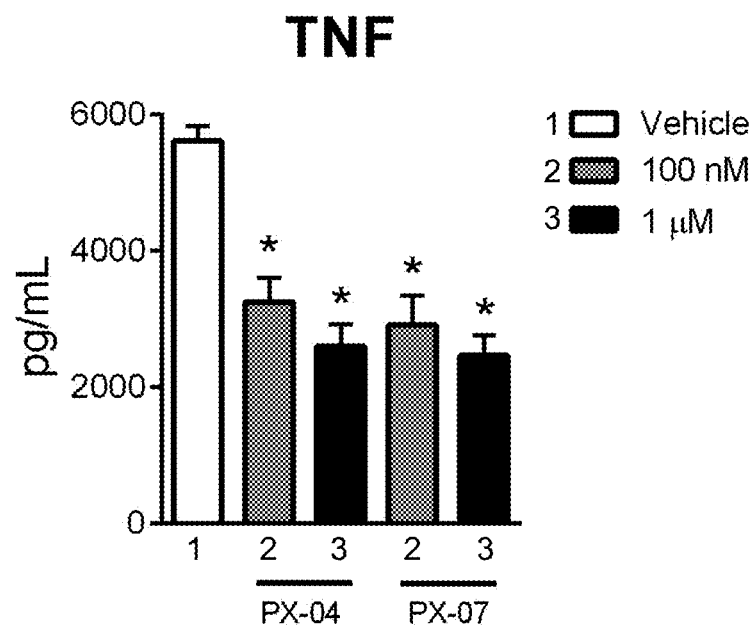
Figure 6C:
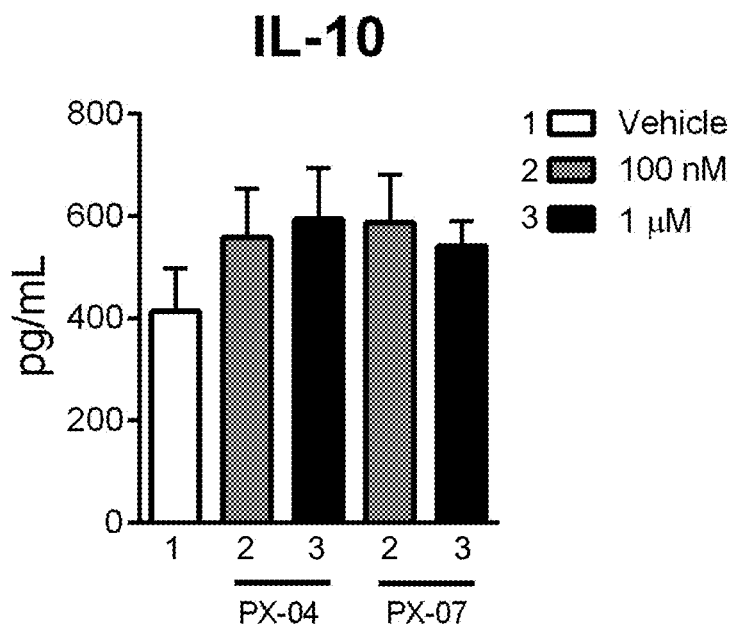

As a critical cell type in the innate immune response, macrophages have a diverse spectrum of functions as both tissue resident cells and cells recruited to sites of inflammation from the blood. Based on their polarization, macrophages can serve as phagocytes, activators of other immune cells, and resolvers of inflammation, among other functions. The immune functions of PLXDC2 were first identified in macrophages, with the stimulation of PLXDC2 resulting in an increased production of IL-10 and the loss of PLXDC2 resulting in an increased production of TNF and nitric oxide.
Methods Cell culture. Bone marrow was flushed from the femur and tibia of C57BL/6 mice. Bone marrow was then resuspended and filtered to provide a cellular suspension. Red blood cells were lysed through hypotonic lysis. Remaining cells were washed and filtered. Isolated cells were incubated in the presence of M-CSF for 7 days to differentiate cells into macrophages. Cells were harvested, plated within 24 well plates and cultured in the presence of PX-04 or PX-07 at 0, 0.1 or 1 micromolar for 12 h. During the last 2-6 h of culture, cells were stimulated with lipopolysaccharide. After stimulation for 2 h, cells were collected for the isolation of RNA. Gene expression was quantified by qRT-PCR. After stimulation for 6 h, supernatant was collected for detection of cytokines by Luminex.
Results By RNA, PX-04 and PX-07 inhibited the expression of TNF (FIG. 5A) while providing a slight increase to IL-10 (FIG. 5B) expression. In the supernatant, IFNγ (FIG. 6A), IL-6 (FIG. 6B) and TNF (FIG. 6C) were greatly suppressed by PX-04 and PX-07. The concentration of IL-10 (FIG. 6D) was observed to be higher with PX-04 and PX-07. In all cases, a dose dependent response was observed with greater effects observed at the higher dose.

Example 9

Use of PX-04 in an Acute Model of Inflammatory Bowel Disease (IBD) Introduction

Inflammatory bowel disease is a multifactorial disease with many disease processes initiated by actions or dysfunction of the epithelial barrier (Abreu et al. 2010). A prominent and accepted animal model of the disease is induced by the administration of dextran sulfate sodium (DSS) in the drinking water of mice. Intake of DSS acts to disrupt and destroy the epithelial barrier in the distal gastrointestinal tract, in particular the colon. The disruption of the epithelial barrier allows for infiltration of the microbiome in the colonic mucosa and the ensuing recruitment and activation of immune cells. While CD4+ T cells are a major focus of development of therapeutics for IBD, macrophage phenotype and distribution in the intestinal lamina propria of IBD patients is altered as well, favoring pro-inflammatory states. Loss of PLXDC2 results in worsened histopathology scores and increased infiltration of neutrophils and lamina propria Th17 cells.

Methods

DSS model. Mice were given DSS in drinking water for seven days to induce disruption of the epithelial layer. At project initiation, mice were 8 weeks of age and began dosing 24 hours after being placed on DSS. Mice were weighed and scored daily for symptoms of disease (diarrhea, rectal bleeding, rectal inflammation, overall behavior). PX-04 was prepared within a 0.5% methylcellulose (12-15 cP) solution. Dosage used was 20 mg/kg delivered once daily. Dosage was calculated based off mean body weights for each gender. Oral dosage was delivered by orogastric gavage of dosage in 0.2 mL volume.

Flow Cytometry. Colons were collected into RPMI/FBS buffer containing collagenase (300 U/mL) and DNase (50 U/mL) for digestion. Tissues were digested for 60 minutes under stirring at 37° C. Resultant cellular suspensions were filtered through 100 µm strainers, centrifuged (300×g, 8 min), and washed in fresh RPMI. Following filtration of the resulting single cell suspensions, immune cells were purified by Percoll gradient of cell-containing 40% Percoll overlayed onto 70% Percoll solution. After centrifugation, interphase was collected and washed to obtain enriched colonic lamina propria cell fractions.

Cells were labeled with mixtures of extracellular (CD45, CD3, CD4, CD8, CD19, NK1.1, CD25, F4/80, CD11b, Gr1, CX3CR1, CD64) and intracellular (Tbet, RORγT, FOXP3, IFNγ, IL17, IL10) antibodies in a sequential live staining in 96-well plates. Data was acquired using a FACS Celesta flow cytometer with FACSDiva software.

Results

Figure 7A:
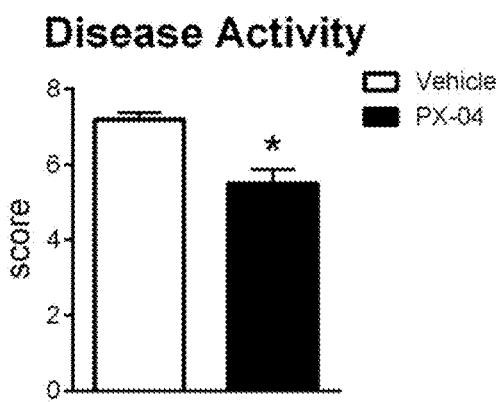
FIGS. 7A-7F. In vivo validation of PX-04 efficacy in a DSS model of colitis. Cumulative disease activity scores through 7 days of DSS challenge (FIG. 7A) and flow cytometry measures of Th17 (FIG. 7B), Treg (FIG. 7C), Th1 (FIG. 7D), IFNγ+ NK (FIG. 7E), and TNF+ dendritic cell (FIG. 7F) populations within the colonic lamina propria on day 7 of mice treated with vehicle or PX-04 daily by oral gavage. Statistical significance (P<0.05) is marked by asterisks.
Figure 7B:
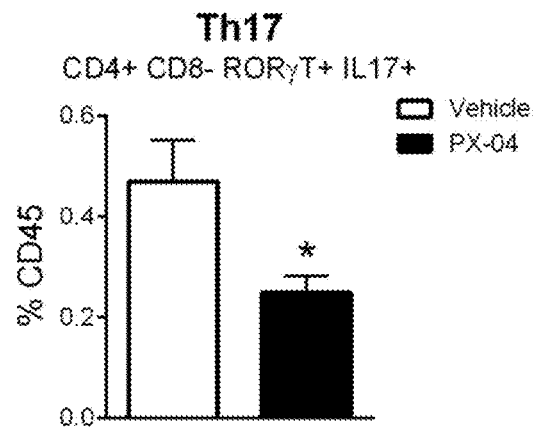
Figure 7C:
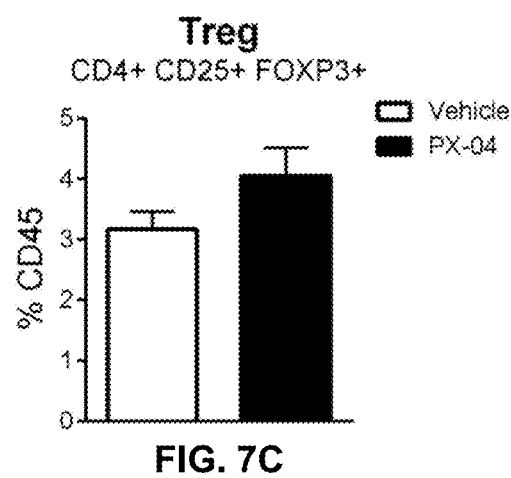
Figure 7D:
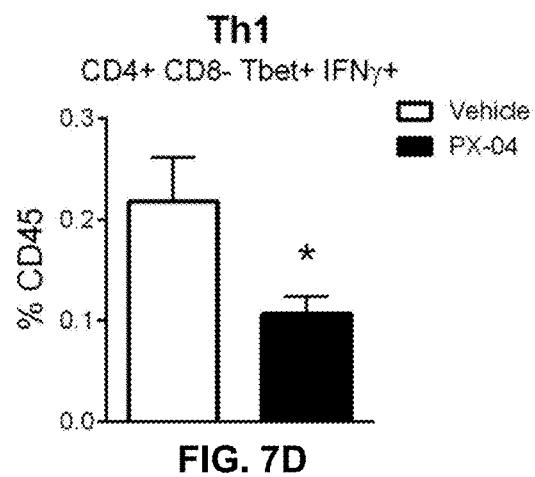
Figure 7E:
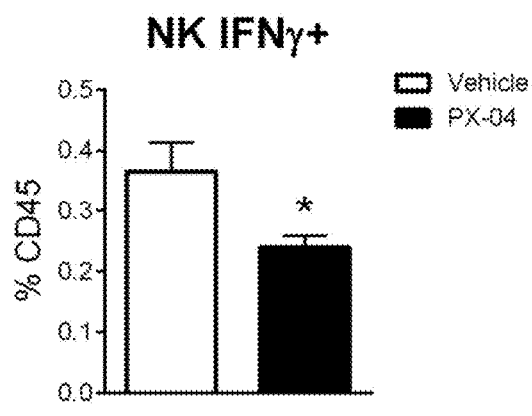
Figure 7F:
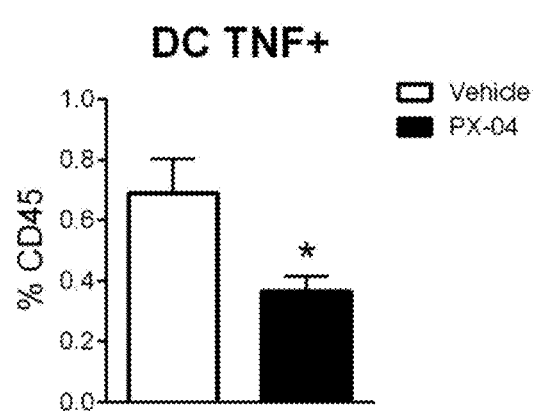

Oral PX-04 treatment decreased the cumulative disease activity of mice challenged with DSS (FIG. 7A). Disease activity in this model of colitis is a summarized score of the weight loss, presence and severity of rectal bleeding, fecal consistency, symptoms of pain and overall behavior of a mouse. Immunologically, PX-04 greatly decreased Th17 cells (FIG. 7B) in the colon while providing a slight increase to regulatory CD4+ T cells (FIG. 7C). Both CD4+ T cells (FIG. 7D) and NK cells (FIG. 7E) exhibited a lower proportion with IFNγ production. Meanwhile, the proportion of TNF producing dendritic cells (FIG. 7F) was decreased by PX-04 treatment.

Example 10

Efficacy of PLXDC2 Ligands in Prevention of Diabetic Complications

Diabetes is a group of diseases which result in impaired glucose metabolism either through a lack of insulin production or increased resistance to available insulin. The high glucose concentrations and resultant oxidative stress can lead to further complications to health and well-being. Among these complications are diabetic retinopathy and diabetic nephropathy, which can lead to blindness and end-stage renal disease, respectively. PEDF is locally expressed in both the retina and kidney and is notably suppressed when damage to either organ occurs. Enhanced activation of PLXDC2 may therefore help return the tissue to homeostasis in the deficiency of the native ligand.

Methods

STZ models. Streptozotocin (STZ) can be used to induce diabetes in both rats and mice. Mice were used for the assessment of nephropathy. DBA/2 mice were injected with 40 mg/kg STZ by intraperitoneal injection for 5 consecutive days. Mice were randomized to vehicle- or PX-04-treated arms after confirmation of diabetes on day 10 (n=12). PX-04 was administered daily for 12 weeks by oral gavage after a damage accrual stage. Separately, mice were randomized to vehicle- or PX-07-treated arms after confirmation of diabetes on day 10 (n=8). PX-07 was administered daily for 12 weeks by oral gavage after a damage accrual stage.

Kidney function. Kidney function was assessed by collection of urine and histological assessment of kidneys. Urine was assayed for albumin/creatinine ratio. Kidneys were scored using a composite scoring method (0-9) encompassing glomerular area, mesangial expansion, and renal fibrosis.

Results

Figure 8:
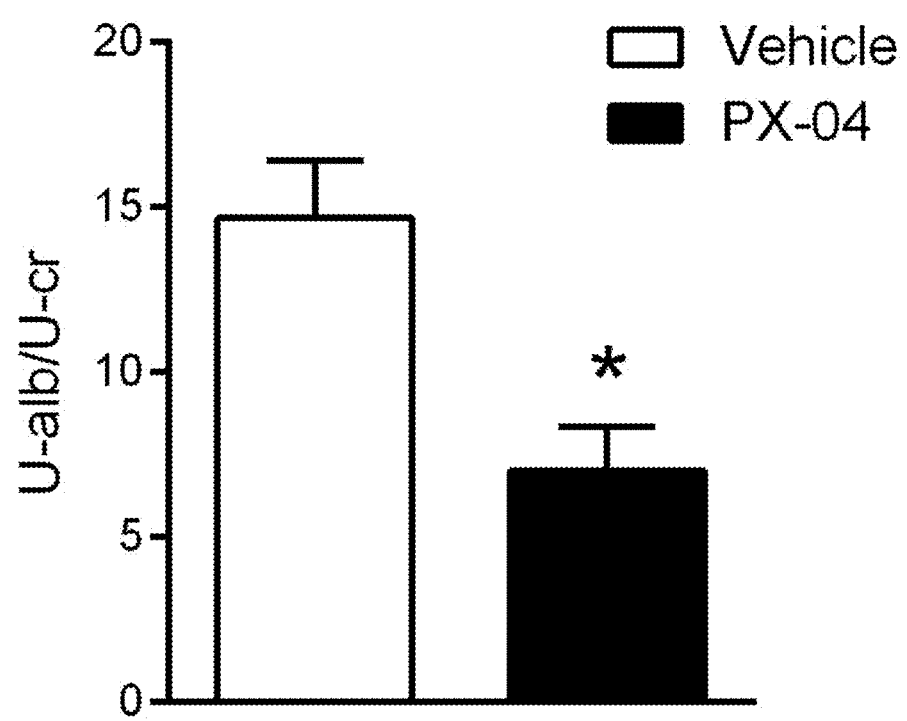
FIG. 8. In vivo validation of PX-04 efficacy in a STZ model of diabetic nephropathy. Urine albumin/creatinine ratio at 12 weeks of treatment in mice treated with vehicle or PX-04 daily by oral gavage. Statistical significance (P<0.05) is marked by asterisks.
Figure 9A:
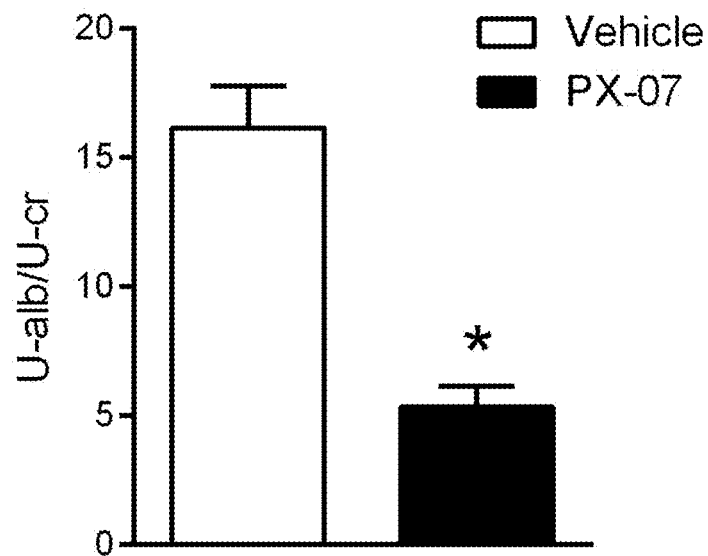
FIGS. 9A-9B. In vivo validation of PX-07 efficacy in a STZ model of diabetic nephropathy. Urine albumin/creatinine ratio at 12 weeks of treatment in mice treated with vehicle or PX-07 daily by oral gavage (FIG. 9A). Histological scoring of kidney damage after 12 weeks of treatment in mice treated with vehicle or PX-07 daily by oral gavage (FIG. 9B). Statistical significance (P<0.05) is marked by asterisks.
Figure 9B:
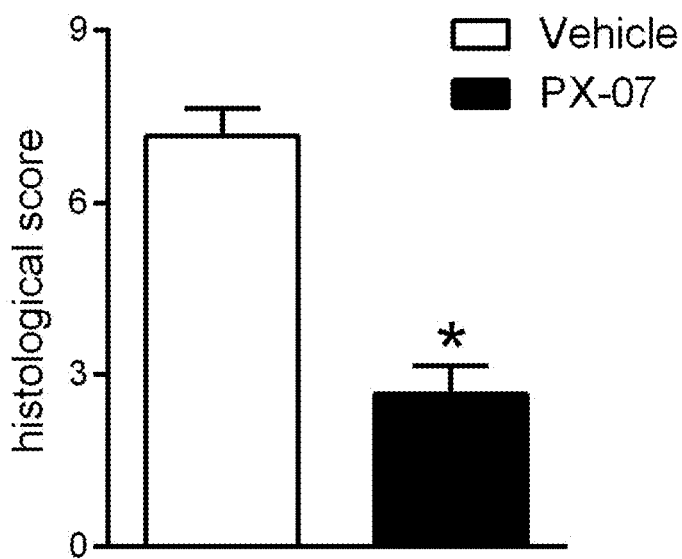

Oral PX-04 significantly reduced the albumin/creatinine ratio in urine (FIG. 8), suggesting a preservation of kidney function, as higher albumin/creatinine ratio is a marker for kidney disease. Oral PX-07 significantly reduced albumin/creatinine ratio in urine (FIG. 9A) and histological score (FIG. 9B) after 12 weeks of treatment.

Example 11

Efficacy of PLXDC2 Ligands in a Genetic Mouse Model of SLE

Systemic lupus erythematosus (SLE) is a systemic autoimmune disease that can cause damage to kidneys, cardiovasculature, and joints. SLE is a result of a complex interaction of genetic factors that results in immunological disease manifested primarily through a generation of autoantibodies. The native ligand of PLXDC2 has been shown to prevent kidney damage. Decreased neutrophil recruitment and inflammatory immune cell polarization would also help to treat symptoms and complications of disease. One preclinical model aimed at captured these complex factors is the NZB/W F1 model. The F1 cross of NZB and NZW mice results in mice with autoimmunity of progressive severity. This autoimmunity shares many common features with human SLE including the generation of anti-nuclear antibodies, kidney damage and elevated type I interferon responses.

Methods

NZB/W F1 model. Twenty-four-week-old, female NZB/W F1 mice were randomized into vehicle or PX-04 treated arms based on baseline urine protein levels (n=10). PX-04 was administered daily at 10 mg/kg for 12 weeks. Mice will be weighed on a weekly basis to update dosage formulation. Dosage will be calculated based off mean body weights.

Immunological analysis. Urine was collected for assay for protein content to test for kidney function at baseline, 6, and 12 weeks of treatment. Spleens were excised, crushed and filtered to provide a cellular suspension. Red blood cells were lysed. Cells were labeled with mixtures of extracellular (CD45, CD3, CD4) and intracellular (IL10) antibodies in a sequential live staining in 96-well plates in preparation for flow cytometry. Data was captured on a BD FACS Celesta and analyzed using FACSDiva.

Results

Figure 10A:
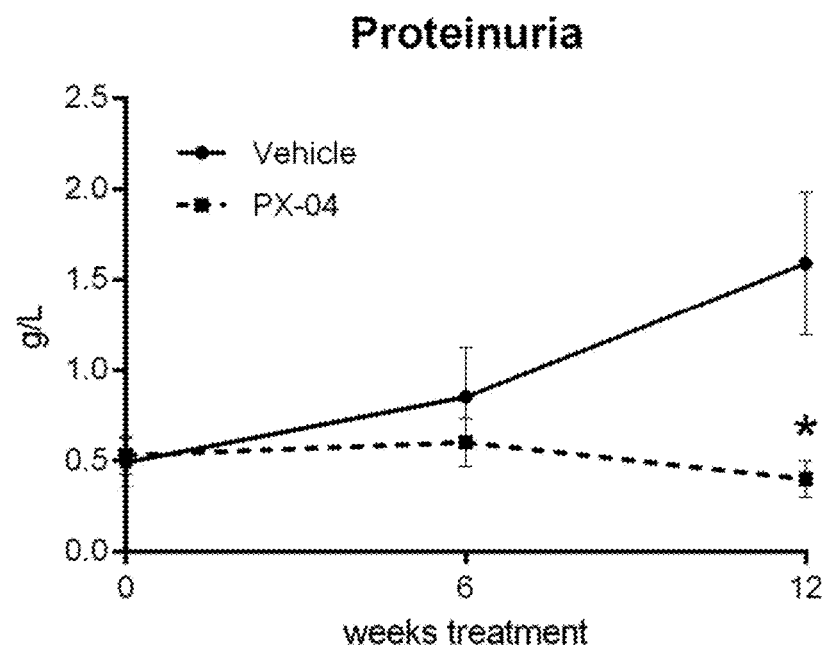
FIGS. 10A-10B. In vivo validation of PX-04 efficacy in an NZB/W F1 model of SLE. Proteinuria over 12 weeks of treatment with vehicle or PX-04 daily by oral gavage (FIG. 10A). Splenic CD4+ IL10+ cells as proportion of CD45+ cells after 12 weeks of treatment (FIG. 10B). Statistical significance (P<0.05) is marked by asterisks.
Figure 10B:
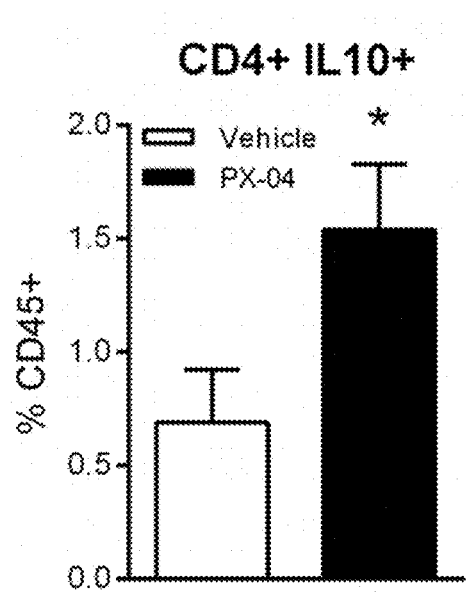

Oral PX-04 protected mice from the worsening of proteinuria grade (FIG. 10A). At 12 weeks of treatment, PX-04-treated mice had a slight improvement of proteinuria relative to baseline on average. In comparison, vehicle-treated mice experienced an approximate tripling of baseline levels. In the spleen, PX-04-treated mice presented with an increased proportion of CD4+IL10+ T cells relative to vehicle-treated mice (FIG. 10B).

Example 12

Efficacy of PLXDC2 Ligands in a Mouse Model of Experimental Autoimmune Encephalomyelitis MS afflicts over 700,000 people in the United States and 2.2 million worldwide. This widespread and debilitating illness results in decreased quality of life, with over 1.1 million DALYs, and significant healthcare related costs, over $28 billion yearly in the US (National Multiple Sclerosis Society). The global therapeutic market for MS is currently $20.5 billion per year and growing at 2.5% per year. MS patients have a higher rate of nonparticipation in the labor force with nearly 60% of patients unemployed, with 25% of patients progressing to the point of requiring home care due to disability. Despite advances and new therapies, no evidence of disease activity (NEDA) rates are 30-40%, yearly relapse rates for MS are still 30%, with only minimal effects on the progression of disease and time to disability. The pathogenesis of MS is thought to involve pathogenic Th17 cells, which are reduced with PX-04 treatment.

Methods

Mouse model. We will challenge 6- to 8-week-old C57BL6 mice with MOG immunization. Complete Freund's adjuvant (CFA) will be prepared by suspension of heat-killed *Mycobacterium tuberculosis* (H37RA) at 10 mg/mL in incomplete Freund's adjuvant. MOG35-55 will be resuspended in sterile nanopure water to a concentration of 2 mg/mL. CFA and MOG35-55 solution will be emulsified in a 1:1 ratio using glass syringes and a near-closed three-way valve for 10 minutes. Emulsion will be left to sit for 30 prior to immunization to ensure it is stable. Pertussis toxin will be resuspended to a concentration of 2 µg/mL in PBS. MOG emulsion will be administered to the left and right flank at 100 per site to each mouse. Pertussis toxin will be administered by intraperitoneal injection (200 µL) on days 0 and 2 of the study to each mouse. Mice will be treated daily with PX-04 or other PLXDC2 ligand at 0, 10, 20, or 40 mg/kg. Treatments will be delivered by oral gavage. Mice will be weighed and scored (0-10) daily for disease activity (coordination, gait, paralysis). Necropsies for tissue collection will occur on d 14.

Gene expression. Total RNA from spinal cord and brain will be generated using the Qiagen RNeasy mini kit. cDNA will be generated using the BioRad iScript cDNA synthesis kit. Standard curves will be generated by serial dilution of purified product from a standard PCR reaction with Taq DNA polymerase followed by purification using the Qiagen MinElute PCR purification kit. Expression levels will be obtained from quantitative real-time PCR with SybrGreen supermix on a BioRad CFX96 Thermal cycler followed by normalization to expression of β-actin. Gene expression will be measured for inflammatory cytokines or surface receptors, such as IL-6, TNF, and MCP-1.

Histopathology. H&E stained spinal cord from the lumbar region will be prepared from tissue collected into 10% buffered formalin and embedded in paraffin. Slides will be examined by a board-certified veterinary pathologist via an Olympus microscope and images will be collected with Image-Pro software. Samples will be scored and evaluated for number of focal lesions, percentage of demyelination and overall leukocyte infiltration.

Flow Cytometry. Spinal cords will be collected into RPMI/FBS buffer containing papain (5 U/mL) and DNase (25 U/mL) for digestion. Tissues will be digested for 30 minutes under stirring at 37° C. then quenched with ovomucoid. Resultant cellular suspensions will be filtered through 100 µm strainers, centrifuged (300×g, 8 min), and washed in fresh RPMI. Following filtration of the resulting single cell suspensions, immune cells will be purified by Percoll gradient of cell-containing 40% Percoll overlayed onto 70% Percoll solution. After centrifugation, interphase will be collected and washed to obtain enriched immune cell fractions. Spleens will be excised and crushed to obtain a single-cell suspension following lysis of red blood cells. Cells from spinal cord and spleen will be labeled with mixtures of extracellular (CD45, CD3, CD4, CD8, CD19, NK1.1, CD25, F4/80, CD11b, Gr1, CX3CR1, CD64, CD40, CTLA4) and intracellular (Tbet, RORγT, FOXP3, IFNγ, IL17, IL10, granzyme B, iNOS) antibodies in a sequential live staining in 96-well plates. Data will be acquired using a FACS Celesta flow cytometer with FACSDiva software.

Results

Mice treated with PX-04 are expected to have lower disease activity during challenge with experimental autoimmune encephalomyelitis. The lowered disease activity is expected to correspond with decreased TNF in the spinal cord, reduced focal lesions, and lower presence of Th17 cells in the spinal cord and spleen. Decreased inflammation is expected to lower the risk for relapse and progression of disease.

Example 13

Efficacy of PLXDC2 Ligands in a Solid Tumor Mouse Model

Angiogenesis is a process that exists in a homeostatic balance, with a bias toward anti-angiogenic factors in normal tissue. Neoplastic lesions shift this balance towards pro-angiogenesis, resulting in increased vascularization that provides the tumor with ample metabolites and an avenue for metastasis. The degree of vascularization varies between different types of cancers. Particular cancers that may benefit from anti-angiogenic therapy may include pancreatic neuroendocrine carcinoma, non-small cell lung cancer, renal cell cancer, colorectal cancer, medullary thyroid cancer, hepatocellular carcinoma, thyroid carcinoma, cervical cancer, and cancers exhibiting metastasis in general. Clear evidence has mounted that enabling factors beyond genetic instability, unlimited proliferation and apoptotic resistance are needed in the development of cancer. These factors, such as local angiogenesis, altered metabolism and immune evasion, have led to a new generation of cancer therapeutics with the ability to improve the prognosis in intermediate and advanced stages. As a novel immune regulator with potential important function in angiogenic balance and immune cell recruitment, PLXDC2 may serve as a potent target for the treatment of solid tumors.

Methods

Mouse model. Adult BALB/c mice will be injected with $5\times10^6$ CT26 carcinoma cells subcutaneously in the hind flank. Mice will be treated daily with PX-04 or other PLXDC2 ligand at doses of 10, 20 and 40 mg/kg either orally via gavage or intravenously by tail vein injection. Mice will be weighed daily, and tumor diameter will be measured every 3 days. Weights, tumor size and survival will be measured up to 40 days after CT26 introduction and will be primary measures of efficacy. Tumors and draining lymph nodes will be collected during necropsy at project termination for analysis of gene expression, histopathology and flow cytometry.

Gene expression. Total RNA from tumors and lymph nodes will be generated using the Qiagen RNeasy mini kit. cDNA will be generated using the BioRad iScript cDNA synthesis kit. Standard curves will be generated by serial dilution of purified product from a standard PCR reaction with Taq DNA polymerase followed by purification using the Qiagen MinElute PCR purification kit. Expression levels will be obtained from quantitative real-time PCR with SybrGreen supermix on a BioRad CFX96 Thermal cycler followed by normalization to expression of β-actin. Gene expression will be measured for inflammatory cytokines or surface receptors, angiogenesis, such as VEGFR, PDGF, MMP9, and tumor growth and metastasis.

Histopathology. H&E stained tumor and lymph node sections will be prepared from tissue collected into 10% buffered formalin and embedded in paraffin. Slides will be examined by a board-certified veterinary pathologist via an Olympus microscope and images will be collected with Image-Pro software. Samples will be scored and evaluated for presence of tumor infiltrating leukocytes, areas of necrosis, angiogenesis and proportion of proliferating tumor cells.

Flow Cytometry. Tumors and lymph nodes will be collected into RPMI/FBS buffer containing collagenase (300 U/mL) and DNase (50 U/mL) for digestion. Tissues will be digested for 60 minutes under stirring at 37° C. Resultant cellular suspensions will be filtered through 100 μm strainers, centrifuged (300×g, 8 min), and washed in fresh RPMI. Following filtration of the resulting single cell suspensions, immune cells will be purified by Percoll gradient of cell-containing 40% Percoll overlayed onto 70% Percoll solution. After centrifugation, interphase will be collected and washed to obtain enriched immune cell fractions. Cells will be labeled with mixtures of extracellular (CD45, CD3, CD4, CD8, CD19, NK1.1, CD25, F4/80, CD11b, Gr1, CX3CR1, CD64, CD40, CTLA4) and intracellular (Tbet, RORγT, FOXP3, IFNγ, IL17, IL10, granzyme B, iNOS) antibodies in a sequential live staining in 96-well plates. Data will be acquired using a FACS Celesta flow cytometer with FACSDiva software.

Results

The CT26 solid tumor model is a highly immunogenic model of carcinoma, making it a valuable model in the evaluation of novel therapeutics that may have an immune component. PLXDC2 ligands may exhibit effects on angiogenesis in solid tumors. As such these ligands are predicted to reduce tumor size and improve survival relative to untreated controls. Histologically and transcriptionally, this is predicted to correlate with decreased markers of angiogenesis.

Example 14

Efficacy of PLXDC2 Ligands in Rodent Models of Rheumatoid Arthritis

Rheumatoid arthritis (RA) causes severe inflammation of joints leading to loss of mobility and intense pain. The underlying immunology of the synovial inflammation is complex involving the interplay of myeloid cells, T cells, fibroblasts and other structural cells of the synovium. High expression of TNF and IL-6 are central to the pathogenesis of RA, with additional contributions by IL-1β, IL-12, IL-17, IL-21, IL-23, MCP1, and TGF-β. Together these cytokines can lead to leukocytic recruitment, bone remodeling, pannus formation, oxidative stress and hyperplasia of the joint lining. As a strong regulator of myeloid responses, including the production of TNF and IL-6 as well as overall infiltration and angiogenesis, PLXDC2 can serve as a novel target in RA.

Methods

Models. Six-week-old C57Bl/6 mice were immunized with 200 μg of chicken collagen emulsified in complete Freund's adjuvant by intradermal injections at the base of the tail (n=8). Mice were treated with 5 mg/kg of PX-07 or vehicle daily for four weeks. Five- to six-week-old Lewis rats (n=8) were immunized with 200 μg of bovine collagen emulsified in incomplete Freund's adjuvant by intradermal injection into the base of the tail. A second boosting immunization was given after one week. PX-04 was administered daily at 2 or 20 mg/kg for 3 weeks.

Immunological analysis. Spleens were excised from mice and inguinal lymph nodes were excised from rats. Tissues were crushed and filtered to provide a cellular suspension. Red blood cells were lysed. Cells were labeled with mixtures of extracellular (CD45, CD3, CD4, CD8, B220, CD19, CD138, CD21, CD24, CD1d, CD11b, CD86, CD80) and intracellular (BCL6, IL21, IL10, TNF) antibodies in a sequential live staining in 96-well plates in preparation for flow cytometry. Data was captured on a BD FACS Celesta and analyzed using FACSDiva.

Results

Figure 11A:
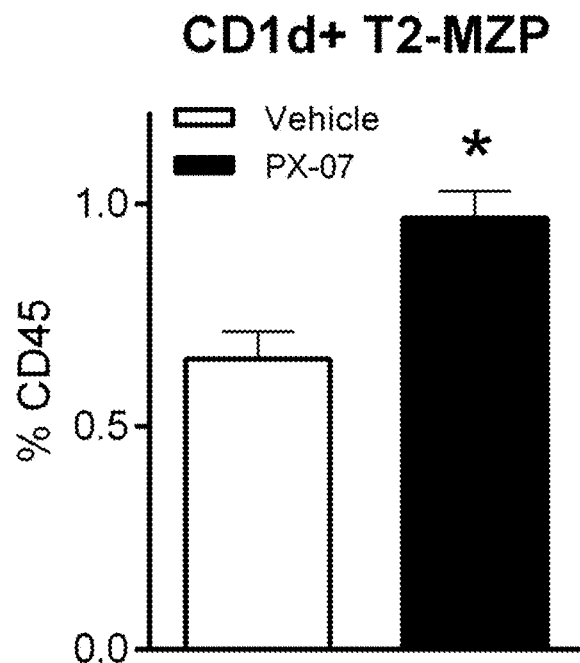
FIGS. 11A-11B. In vivo validation of PX-07 efficacy in a mouse model of arthritis. Splenic CD1d+ T2-MZP B cells (FIG. 11A) and CD4+ IL21+ BCL6+ (FIG. 11B) after four weeks of treatment with vehicle or PX-07 daily by oral gavage in mice with collagen-induced arthritis. Statistical significance (P<0.05) is marked by asterisks.
Figure 11B:
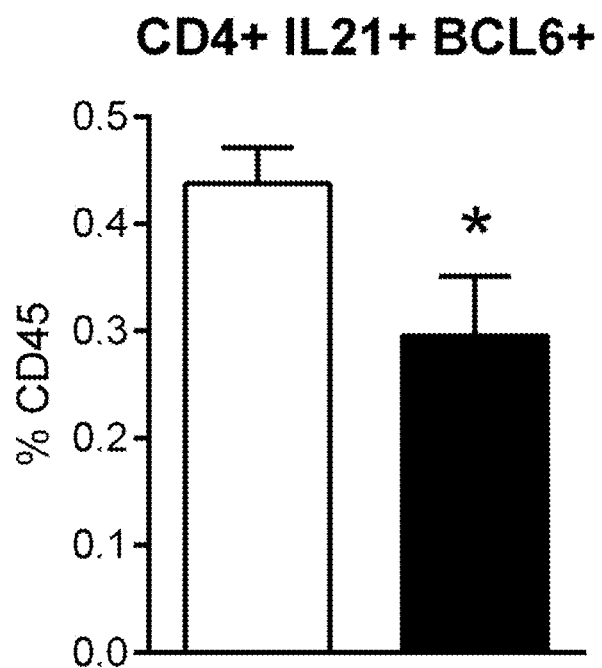
Figure 12A:
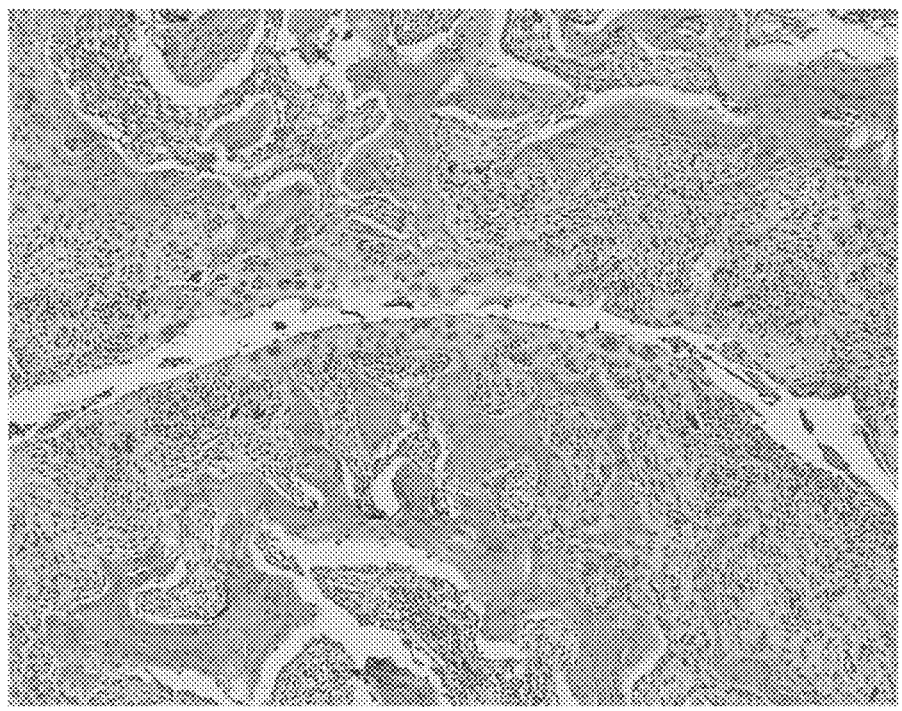
FIGS. 12A-12B. Histological validation of PX-04 efficacy in a rat model of arthritis. Representative photomicrographs of hind ankles from vehicle (FIG. 12A) and PX-04 (2 mg/kg) (FIG. 12B) treated rats with collagen-induced arthritis.
Figure 12B:
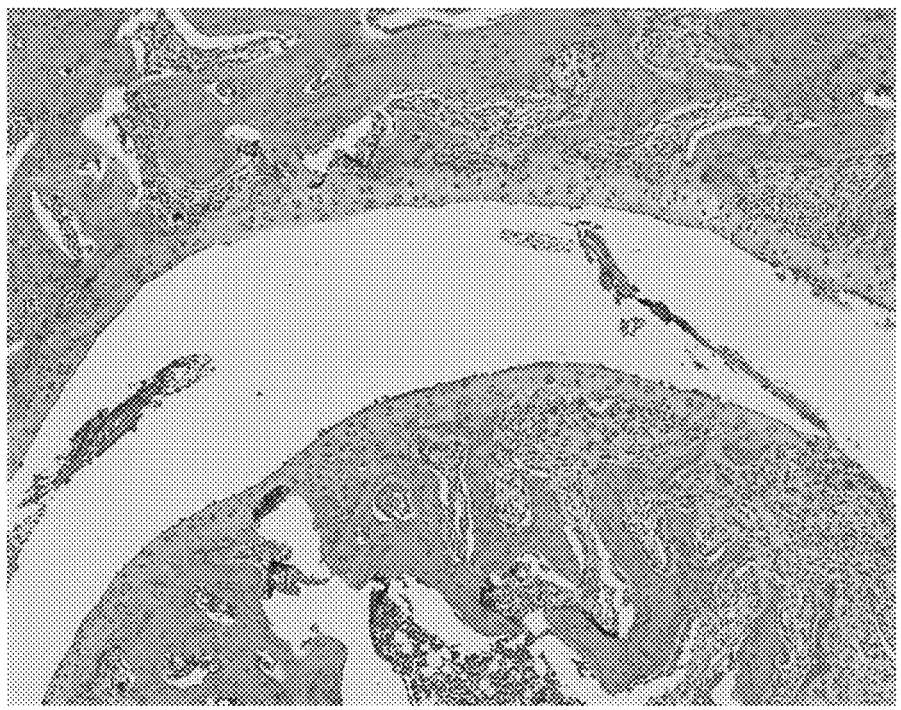
Figure 13A:
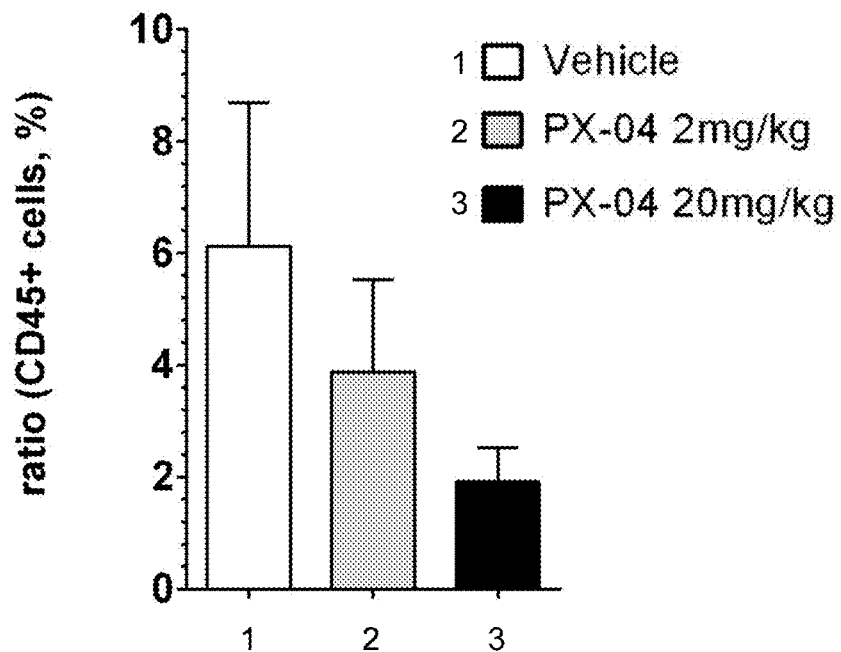
FIGS. 13A-13B. In vivo validation of PX-04 efficacy in a rat model of arthritis. Ratios of TNF+ to IL10+ cells within myeloid (FIG. 13A) and CD4+ T (FIG. 13B) cell fractions from the inguinal lymph nodes after 3 weeks of treatment with vehicle or PX-04 daily by oral gavage in rats with collagen-induced arthritis.
Figure 13B:
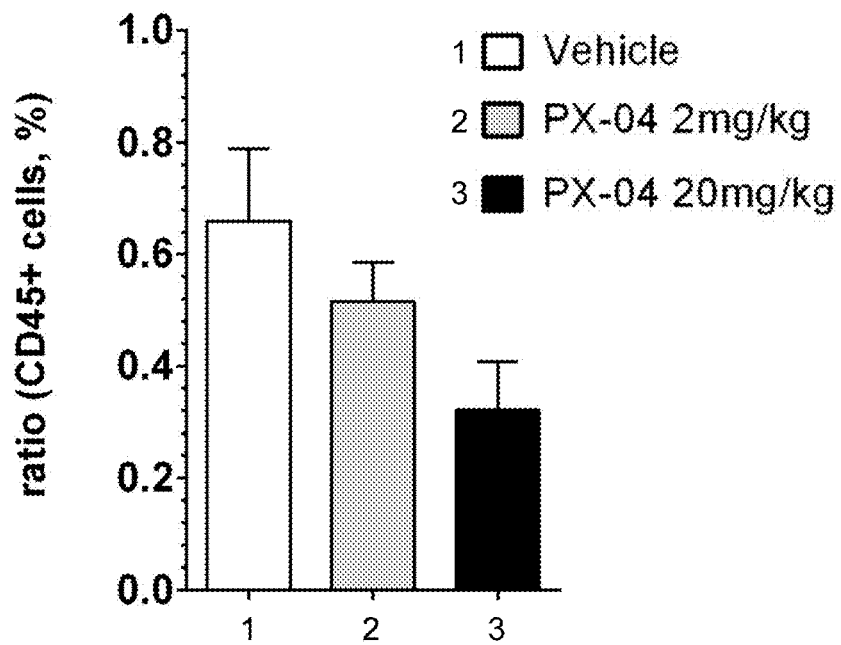
Figure 14A:
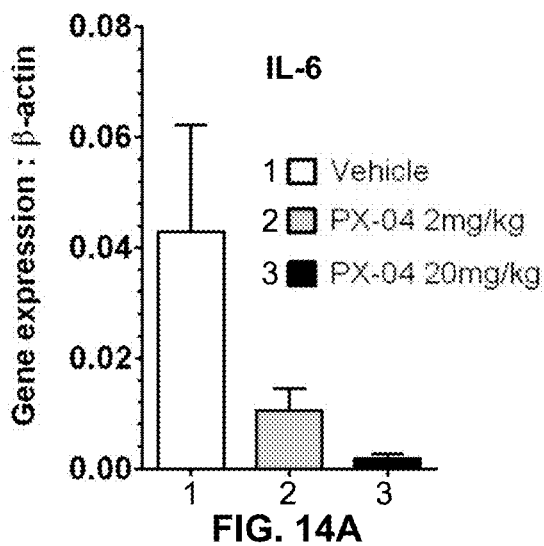
FIGS. 14A-14C. Gene expression validation of PX-04 efficacy in a rat model of arthritis. Normalized gene expression of IL-6 (FIG. 14A), IL-1β (FIG. 14B) and CXCL1 (FIG. 14C) within the hind ankle synovium after 3 weeks of treatment with vehicle or PX-04 (2 and 20 mg/kg) daily by oral gavage in rats with collagen-induced arthritis.
Figure 14B:
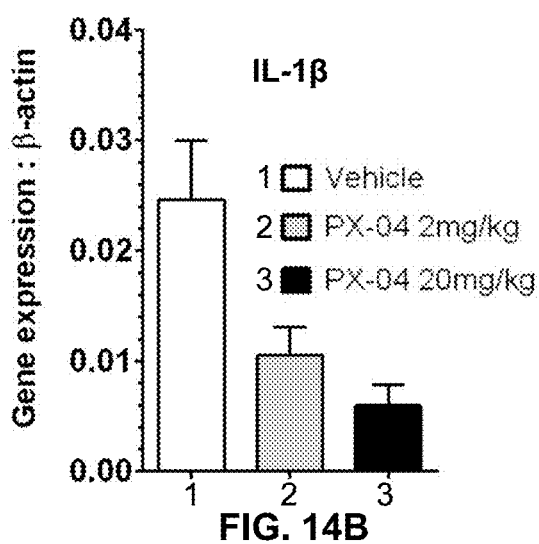
Figure 14C:
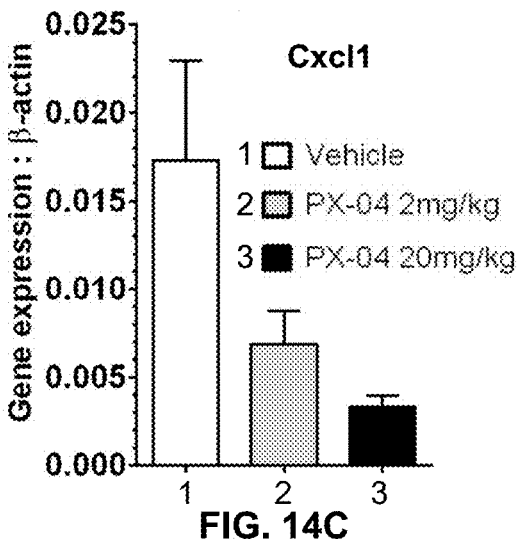

Oral PX-07 increased the proportion of CD1d+T2-MZP B cells in the spleen of collagen-induced arthritis mice (FIG. 11A). CD1d+T-MZP B cells are believed to be a main regulatory cell type associated with lower disease activity in arthritis. PX-07 also decreased the proportion of T follicular helper cells (CD4+IL21+BCL6+) in the spleen (FIG. 11B). Histologically, oral PX-04 reduced severity of disease (FIG. 12B) relative to vehicle treatment (FIG. 12A) in terms of maintenance of joint space, prevention of cartilage erosion, leukocytic infiltration and angiogenesis. Oral PX-04 decreased the ratio of TNF+ to IL10+ cells in the inguinal lymph node of rats with collagen induced arthritis, both within myeloid (FIG. 13A) and CD4+ T (FIG. 13B) cell fractions. By gene expression, PX-04 reduced expression of inflammatory cytokines and chemokines, including IL-6 (FIG. 14A), IL-1β (FIG. 14B), and CXCL1 (FIG. 14C), within the synovium relative to vehicle.

REFERENCES

Abreu, M. T., Toll-like receptor signalling in the intestinal epithelium: how bacterial recognition shapes intestinal function. *Nat Rev Immunol*, 2010. 10(2): p. 131-44.
Belkacemi, L. and S. X. Zhang, Anti-tumor effects of pigment epithelium-derived factor (PEDF): implication for cancer therapy. A mini-review. *J Exp Clin Cancer Res*, 2016. 35: p. 4.
Cheng, G., et al., Identification of PLXDC1 and PLXDC2 as the transmembrane receptors for the multifunctional factor PEDF. *Elife*, 2014. 3: p. e05401.
Dattatreya et al., A Brief Review on Immune Mediated Diseases. *J Clin Cell Immunol* 2011, S11. DOI: 10.4172/2155-9899.S11-001 ISSN:2155-9899 JCCI Dawson, D. W., et al., Pigment epithelium-derived factor: a potent inhibitor of angiogenesis. *Science*, 1999. 285(5425): p. 245-8.
Doll, J. A., et al., Pigment epithelium-derived factor regulates the vasculature and mass of the prostate and pancreas. *Nat Med*, 2003. 9(6): p. 774-80.
O'Connell, G. C., et al., Shifts in Leukocyte Counts Drive the Differential Expression of Transcriptional Stroke Biomarkers in Whole Blood. *Transl Stroke Res*, 2019. 10(1): p. 26-35.
Sanchez, A., et al., Pigment epithelium-derived factor (PEDF) protects cortical neurons in vitro from oxidant injury by activation of extracellular signal-regulated kinase (ERK) 1/2 and induction of Bcl-2. *Neurosci Res*, 2012. 72(1): p. 1-8.
Shurin M R, Smolkin Y S. Immune-mediated diseases: where do we stand? *Adv Exp Med Biol.* 2007; 601:3-12.
Wang, J. J., et al., Decreased expression of pigment epithelium-derived factor is involved in the pathogenesis of diabetic nephropathy. *Diabetes*, 2005. 54(1): p. 243-50.
Wang, J. J., et al., Anti-inflammatory effects of pigment epithelium-derived factor in diabetic nephropathy. *Am J Physiol Renal Physiol*, 2008. 294(5): p. F1166-73.
Yoshida, Y., et al., Protective role of pigment epithelium-derived factor (PEDF) in early phase of experimental diabetic retinopathy. Diabetes *Metab Res Rev*, 2009. 25(7): p. 678-86.
Zamiri, P., et al., Pigment epithelial growth factor suppresses inflammation by modulating macrophage activation. *Invest Ophthalmol Vis Sci*, 2006. 47(9): p. 3912-8.
Zhang, S. X., et al., Pigment epithelium-derived factor (PEDF) is an endogenous antiinflammatory factor. *FASEB J*, 2006. 20(2): p. 323-5.

EMBODIMENTS OF THE INVENTION

1. A compound of Formula Y-Z, or a salt thereof, wherein: Y is:

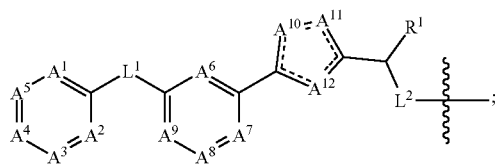

Z is $Z^1$ or $Z^2$;
$Z^1$ is:

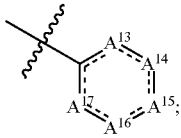

$Z^2$ is:

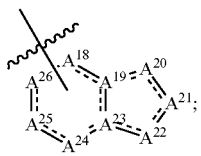

$A^1$, $A^2$, $A^3$, $A^4$, $A^5$, $A^6$, $A^7$, $A^8$, and $A^9$, are each independently $C(R^2)$ or N;
$A^{10}$, $A^{11}$, $A^{12}$, $A^{11}$, $A^{14}$, $A^{15}$, $A^{16}$, $A^{18}$, $A^{20}$, $A^{21}$, $A^{22}$, $A^{24}$, A 25, and $A^{26}$ are each independently O, $N(R^2)$, $C(R^2)_2$, $C(R^2)$, or N, with the proviso that at least one of $A^{18}$, $A^{20}$, $A^{21}$, $A^{22}$, $A^{24}$, $A^{25}$, and $A^{26}$ is $N(R^2)$, $C(R^2)$; or $C(R^2)$;
$A^{19}$ and $A^{23}$ are each independently $C(R^2)$, N, or C;
each --- between adjacent atoms represents a bond that is present or absent;
$L^1$ and $L^2$ are each independently O, $N(R^2)$, or $C(R^2)_2$;
$R^1$ is oxo, $N(R^2)_2$, methyl, ethyl, hydroxyl, unsubstituted C1-C2 alkyloxy, or halogen; and
$R^2$ in each instance is independently hydrogen, halogen, oxo, optionally substituted alkyl, optionally substituted alkenyl, optionally substituted alkynyl, optionally substituted cycloalkyl, optionally substituted cycloalkenyl, hydroxyl, carboxyl, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group, with the proviso that an $R^2$ of one of $A^{18}$, $A^{20}$, $A^{21}$, $A^{22}$, $A^{24}$, $A^{25}$ and $A^{26}$ is Y.

2. The compound of embodiment 1, wherein $R^2$ in each instance is independently, as valency permits, hydrogen, halogen, oxo, optionally substituted C1-C6 alkyl, hydroxyl, carboxyl, optionally substituted cycloalkyl, optionally substituted C1-C6 alkyloxy, optionally substituted amino, acyl, optionally substituted alkyloxycarbonyl, optionally substituted aryl, optionally substituted heteroaryl, or optionally substituted non-aromatic heterocyclic group.

3. The compound of embodiment 1, wherein $R^2$ in each instance is independently, as valency permits, hydrogen, halogen, oxo, unsubstituted C1-C6 alkyl, hydroxyl, carboxyl, unsubstituted cycloalkyl, unsubstituted C1-C6 alkyloxy, unsubstituted amino, acyl, unsubstituted alkyloxycarbonyl, unsubstituted aryl, unsubstituted heteroaryl, or unsubstituted non-aromatic heterocyclic group.

4. The compound of any one of embodiments 1-3, wherein $A^1$ is $C(R^2)$.

5. The compound of any one of embodiments 1-3, wherein $A^1$ is N.

6. The compound of any prior embodiment, wherein $A^2$ is $C(R^2)$.

7. The compound of any prior embodiment, wherein $A^3$ is $C(R^2)$.

8. The compound of embodiment 7, wherein the $R^2$ of $A^3$ is optionally substituted C1-C6 alkyl.

9. The compound of any prior embodiment, wherein $A^4$ is $C(R^2)$.

10. The compound of any prior embodiment, wherein $A^5$ is $C(R^2)$.

11. The compound of any prior embodiment, wherein each $R^2$ of $A^1$, $A^2$, $A^3$, $A^4$, and $A^5$, when present and except where defined otherwise, is independently hydrogen or halogen.

12. The compound of any one of embodiments 1-3, wherein the ring in Y containing $A^1$, $A^2$, $A^3$, $A^4$, and $A^5$ is:

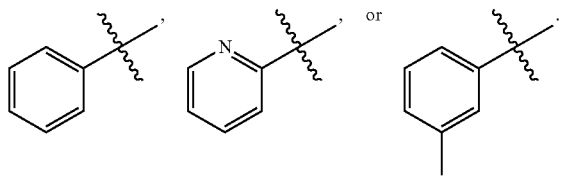

13. The compound of any prior embodiment, wherein $L^1$ is O.

14. The compound of any one of embodiments 1-12, wherein $L^1$ is $N(R^2)$.

15. The compound of any one of embodiments 1-12, wherein $L^1$ is $C(R^2)_2$.

16. The compound of any prior embodiment, wherein $A^6$ is $C(R^2)$.

17. The compound of any one of embodiments 1-15, wherein $A^6$ is N.

18. The compound of any prior embodiment, wherein $A^7$ is $C(R^2)$.

19. The compound of any prior embodiment, wherein $A^8$ is $C(R^2)$.

20. The compound of any prior embodiment, wherein $A^9$ is $C(R^2)$.

21. The compound of any one of embodiments 1-15, wherein the ring in Y containing $A^6$, $A^7$, $A^8$, and $A^9$ is:

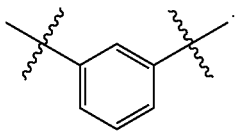 [SMILES: *c1cccc(*)c1]

22. The compound of any prior embodiment, wherein $A^{12}$ is N.

23. The compound of embodiment 22, wherein one of $A^{10}$ and $A^{11}$ is $C(R^2)$ and one of $A^{10}$ and $A^{11}$ is $N(R^2)$.

24. The compound of embodiment 23, wherein the $R^2$ of each of $A^{10}$ and $A^{11}$ is independently hydrogen or halogen.

25. The compound of embodiment 22, wherein one of $A^{10}$ and $A^{11}$ is $C(R^2)$ and one of $A^{10}$ and $A^{11}$ is O.

26. The compound of embodiment 25, wherein the $R^2$ of the one of $A^{10}$ and $A^{11}$ that is $C(R^2)$ is hydrogen or halogen.

27. The compound of embodiment 22, wherein one of $A^{10}$ and $A^{11}$ is N and one of $A^{10}$ and $A^{11}$ is O.

28. The compound of any one of embodiments 1-21, wherein one of $A^{10}$, $A^{11}$ and $A^{12}$ is $C(R^2)_2$ and two of $A^{10}$, $A^{11}$, and $A^{12}$ is $C(R^2)$.

29. The compound of embodiment 28, wherein the $R^2$ of each of $A^{10}$, $A^{11}$ and $A^{12}$ is independently hydrogen or halogen.

30. The compound of any one of embodiments 1-21, wherein the ring in Y containing $A^{10}$, $A^{11}$, and $A^{12}$ is:

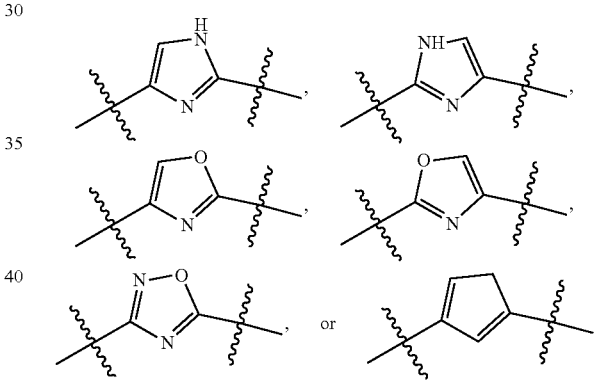

31. The compound of any prior embodiment, wherein $R^1$ is oxo.

32. The compound of any prior embodiment, wherein $L^2$ is $N(R^2)$.

33. The compound of any one of embodiments 1-31, wherein $L^2$ is $C(R^2)_2$.

34. The compound of any one of embodiments 1-31, wherein $L^2$ is O.

35. The compound of any prior embodiment, wherein Z is $Z^1$.

36. The compound of embodiment 35, wherein $A^{11}$ is $C(R^2)$.

37. The compound of any one of embodiments 35-36, wherein $A^{14}$ is $N(R^2)$.

38. The compound of embodiment 37, wherein the $R^2$ of $A^{14}$ is optionally substituted C1-C6 alkyl.

39. The compound of embodiment 37, wherein the $R^2$ of $A^{14}$ is independently hydrogen or halogen.

40. The compound of embodiment 35-36, wherein $A^{14}$ is N.

41. The compound of embodiment 35-36, wherein $A^{14}$ is $C(R^2)$.

42. The compound of embodiment 41, wherein the $R^2$ of $A^{14}$ is carboxyl, acyl, optionally substituted alkyloxycarbonyl, optionally substituted alkenyloxycarbonyl, optionally substituted alkynyloxycarbonyl, or optionally substituted aryloxycarbonyl.

43. The compound of embodiment 41, wherein the $R^2$ of $A^{14}$ is carboxyl.

44. The compound of any one of embodiments 35-43, wherein $A^{15}$ is $C(R^2)$ or $C(R^2)_2$.

45. The compound of embodiment 44, wherein $A^{15}$ is $C(R^2)_2$ and one $R^2$ of the $C(R^2)_2$ of $A^{15}$ is hydroxyl or optionally substituted alkyloxy.

46. The compound of embodiment 44, wherein $A^{15}$ is $C(R^2)$ and the $R^2$ of $A^{15}$ is oxo.

47. The compound of any one of embodiments 35-46, wherein $A^{16}$ is $C(R^2)$.

48. The compound of any one of embodiments 35-47, wherein $A^{17}$ is $C(R^2)$.

49. The compound of any prior embodiment, wherein each $R^2$ of $A^{13}$, $A^{14}$, $A^{15}$, $A^{16}$, and $A^{17}$, when present and except where defined otherwise, is independently hydrogen or halogen.

50. The compound of any one of embodiments 1-35, wherein $Z^1$ is:

[chemical structures]

51. The compound of any one of embodiments 1-34, wherein Z is $Z^2$.

52. The compound of embodiment 51, wherein $A^{18}$ is $C(R^2)$.

53. The compound of any one of embodiments 51-52, wherein $A^{19}$ is C.

54. The compound of any one of embodiments 51-53, wherein $A^{23}$ is C.

55. The compound of any one of embodiments 51-54, wherein $A^{24}$ is $C(R^2)$.

56. The compound of any one of embodiments 51-55, wherein $A^{25}$ is $C(R^2)$.

57. The compound of any one of embodiments 51-56, wherein $A^{26}$ is $C(R^2)$.

58. The compound of any one of embodiments 51-57, wherein $A^{21}$ is O.

59. The compound of any one of embodiments 51-58, wherein $A^{20}$ and $A^{22}$ are each $C(R^2)_2$.

60. The compound of any one of embodiments 51-59, wherein $A^{26}$ is $C(R^2)$ and the $R^2$ of $A^{26}$ is Y.

61. The compound of any one of embodiments 51-57, wherein $A^{20}$ is N.

62. The compound of embodiment 61, wherein $A^{22}$ is $N(R^2)$.

63. The compound of embodiment 61, wherein $A^{22}$ is O.

64. The compound of any one of embodiments 61-63, wherein $A^{24}$ is $C(R^2)$ and the $R^2$ of $A^{24}$ is hydrogen, halogen, or optionally substituted C1-C6 alkyl.

65. The compound of any one of embodiments 61-64, wherein $A^{21}$ is $C(R^2)$.

66. The compound of any one of embodiments 61-65, wherein $A^{21}$ is $C(R^2)$ and the $R^2$ of $A^{21}$ is Y.

67. The compound of any one of embodiments 61-65, wherein $A^{26}$ is $C(R^2)$ and the $R^2$ of $A^{26}$ is Y.

68. The compound of embodiment 51, wherein $A^{18}$ is $C(R^2)_2$.

69. The compound of any one of embodiments 51 and 68, wherein $A^{19}$ is $C(R^2)$.

70. The compound of any one of embodiments 51 and 68-69, wherein $A^{20}$ is $N(R^2)$.

71. The compound of any one of embodiments 51 and 68-70, wherein $A^{21}$ is $C(R^2)_2$.

72. The compound of embodiment 71, wherein one $R^2$ of $A^{21}$ is Y and the other $R^2$ of $A^{21}$ is hydrogen.

73. The compound of any one of embodiments 51 and 68-72, wherein $A^{22}$ is $C(R^2)_2$.

74. The compound of embodiment 51 and 68-72, wherein $A^{22}$ is $C(R^2)$.

75. The compound of embodiment 74, wherein the $R^2$ of $A^{22}$ is oxo.

76. The compound of any one of embodiments 51 and 68-75, wherein $A^{23}$ is N.

77. The compound of any one of embodiments 51 and 68-76, wherein $A^{24}$ is $C(R^2)_2$.

78. The compound of any one of embodiments 51 and 68-77, wherein $A^{25}$ is $C(R^2)_2$.

79. The compound of embodiment 51 and 68-77, wherein $A^{25}$ is $C(R^2)$.

80. The compound of embodiment 79, wherein the $R^2$ of $A^{25}$ is oxo.

81. The compound of any one of embodiments 51 and 68-80, wherein $A^{26}$ is $N(R^2)$.

82. The compound of any one of embodiments 51-81, wherein each $R^2$ of $A^{18}$, $A^{19}$, $A^{20}$, $A^{21}$, $A^{22}$, $A^{23}$, $A^{24}$, $A^{25}$, and $A^{26}$, when present and except where defined otherwise, is independently hydrogen or halogen.

83. The compound of any one of embodiments 1-51, wherein $Z^2$ is:

[chemical structures]

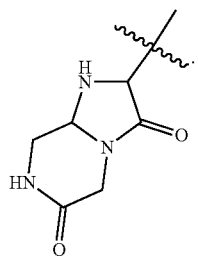

84. The compound of any prior embodiment, wherein each $R^2$, when present and except where defined otherwise, is independently hydrogen or halogen.

85. The compound of any prior embodiment, wherein each $R^2$, when present and except where defined otherwise, is hydrogen.

86. The compound of embodiment 1, wherein the compound has a structure of PX-02, PX-03, PX-04, PX-05, PX-06, PX-07, PX-08, PX-09, PX-10, PX-11, PX-12, PX-13, PX-14, PX-15, PX-16, PX-17, PX-18, PX-19, PX-20, PX-21, PX-22, PX-23, PX-24, PX-25, PX-26, PX-27, PX-28, PX-29, PX-30, PX-31, PX-32, PX-33, PX-34, PX-35, PX-36, or PX-37, or a salt of any of the foregoing.

87. A method of treating a condition in an animal with a compound as recited in any prior embodiment, comprising administering an effective amount of the compound to the animal, wherein the condition is selected from the group consisting of an inflammatory or immune-mediated disease, an infectious disease, and a cancer.

88. The method of embodiment 87, wherein the condition is an inflammatory or immune-mediated disease.

89. The method of embodiment 88, wherein the inflammatory or immune-mediated disease is an autoimmune disease.

90. The method of embodiment 89, wherein the autoimmune disease is selected from the group consisting of systemic lupus erythematosus, rheumatoid arthritis, multiple sclerosis, autoimmune encephalitis, type 1 diabetes or associated complications, psoriasis, and inflammatory bowel disease (Crohn's disease and ulcerative colitis).

91. The method of embodiment 87, wherein the condition is an infectious disease of bacterial, fungal, or viral origin.

92. The method of embodiment 87, wherein the condition is a cancer.

What is claimed is:

1. A compound of Formula Y-Z:

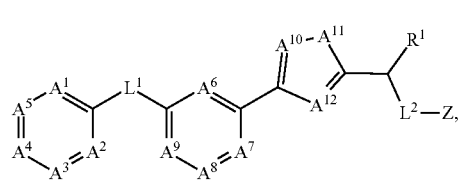

or a pharmaceutically acceptable salt thereof, wherein:
Z is $Z^1$ or $Z^2$;
$Z^1$ is:

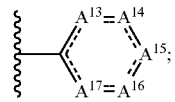

$Z^2$ is:

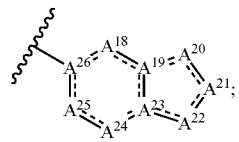

$A^1$ is $CR^2$;
$A^2$ is $CR^2$;
$A^3$ is $CR^2$;
$A^4$ is $CR^2$;
$A^5$ is $CR^2$;
$A^6$ is $CR^2$;
$A^7$ is $CR^2$;
$A^8$ is $CR^2$;
$A^9$ is $CR^2$;
$A^{10}$ is $CR^2$;
$A^{11}$ is $-NR^2-$;
$A^{12}$ is N;
$A^{13}$ is $CR^2$, $-C(R^2)_2-$, N, $-NR^2-$, or $-O-$;
$A^{14}$ is $CR^2$, $-C(R^2)_2-$, N, $-NR^2-$, or $-O-$;
$A^{15}$ is $CR^2$, $-C(R^2)_2-$, N, $-NR^2-$, or $-O-$;
$A^{16}$ is $CR^2$, $-C(R^2)_2-$, N, $-NR^2-$, or $-O-$;
$A^{17}$ is $CR^2$, $-C(R^2)_2-$, N, $-NR^2-$, or $-O-$;
$A^{18}$ is $CR^2$, $-C(R^2)_2-$, N, $-NR^2-$, or $-O-$;
$A^{19}$ is C, $CR^2$, or N;
$A^{20}$ is $CR^2$, $-C(R^2)_2-$, N, $-NR^2-$, or $-O-$;
$A^{21}$ is $CR^2$, $-C(R^2)_2-$, N, $-NR^2-$, or $-O-$;
$A^{22}$ is $CR^2$, $-C(R^2)_2-$, N, $-NR^2-$, or $-O-$;
$A^{23}$ is C, $CR^2$, or N;
$A^{24}$ is $CR^2$, $-C(R^2)_2-$, N, $-NR^2-$, or $-O-$;
$A^{25}$ is $CR^2$, $-C(R^2)_2-$, N, $-NR^2-$, or $-O-$;
$A^{26}$ is C, $CR^2$, or N;
each --- is independently a single or double bond;
$L^1$ is $-O-$;
$L^2$ is $-NR^2-$;
$R^1$ is $=O$;
each $R^2$ is independently H, halogen, CN, $NO_2$, $=O$, alkyl, alkenyl, alkynyl, acyl, C(O)OH, C(O)O(alkyl), C(O)O(alkenyl), C(O)O(alkynyl), C(O)O(aryl), $NH_2$, OH, O(alkyl), O(alkenyl), O(alkynyl), $OS(O)_2$alkyl, $OS(O)_2$cycloalkyl, $OS(O)_2$cycloalkenyl, $OS(O)_2$aryl, $OS(O)_2$heteroaryl, O(cycloalkyl), O(cycloalkenyl), O(aryl), O(heteroaryl), SH, S(alkyl), S(alkenyl), S(alkynyl), S(cycloalkyl), S(cycloalkenyl), S(aryl), S(heteroaryl), S(O)alkyl, S(O)cycloalkyl, S(O)cycloalkenyl, S(O)aryl, S(O)heteroaryl, $S(O)_2$alkyl, $S(O)_2NH_2$, $S(O)_2$cycloalkyl, $S(O)_2$cycloalkenyl, $S(O)_2$aryl, $S(O)_2$heteroaryl, cycloalkyl, cycloalkenyl, non-aromatic heterocyclyl, aryl, or heteroaryl;
wherein each alkyl, C(O)O(alkyl), O(alkyl), $OS(O)_2$alkyl, S(alkyl), S(O)alkyl, and $S(O)_2$alkyl is optionally and independently substituted with 1, 2, or 3 substituents independently selected from the group consisting of halogen, CN, $NO_2$, alkylene, acyl, $C(O)NH_2$, C(O)OH, C(O)O(alkyl), $NH_2$, OH, O(alkyl), O(aryl), =O, SH, S(alkyl), $S(O)_2$alkyl, cycloalkyl, non-aromatic heterocyclyl, aryl, and heteroaryl;

wherein each alkylene substituent optionally and independently contains 1 or 2 heteroatoms;

wherein each O(alkyl) substituent is optionally and independently substituted with 1, 2, or 3 independently selected Group A substituents;

wherein each O(aryl) substituent and aryl substituent is optionally and independently substituted with 1, 2, or 3 independently selected Group B substituents; and wherein each non-aromatic heterocyclyl substituent and heteroaryl substituent is optionally and independently substituted with 1, 2, or 3 independently selected Group C substituents;

wherein each alkenyl, alkynyl, C(O)O(alkenyl), C(O)O(alkynyl), O(alkenyl), O(alkynyl), $OS(O)_2$cycloalkyl, $OS(O)_2$cycloalkenyl, O(cycloalkyl), O(cycloalkenyl), S(alkenyl), S(alkynyl), S(cycloalkyl), S(cycloalkenyl), S(O)cycloalkyl, S(O)cycloalkenyl, $S(O)_2$cycloalkyl, $S(O)_2$cycloalkenyl, cycloalkyl, and cycloalkenyl is optionally and independently substituted with 1 or more substituents independently selected from the group consisting of halogen, CN, $NO_2$, alkyl, acyl, $C(O)NH_2$, C(O)OH, C(O)O(alkyl), $NH_2$, OH, O(alkyl), O(acyl), O(aryl), =O, SH, S(alkyl), $S(O)_2$alkyl, cycloalkyl, non-aromatic heterocyclyl, aryl, and heteroaryl;

wherein each alkyl substituent is optionally and independently substituted with 1, 2, or 3 independently selected Group D substituents;

wherein each O(alkyl) substituent is optionally and independently substituted with 1, 2, or 3 independently selected Group A substituents;

wherein each aryl substituent is optionally and independently substituted with 1, 2, or 3 independently selected Group B substituents; and wherein each O(aryl) substituent, non-aromatic heterocyclyl substituent, and heteroaryl substituent is optionally and independently substituted with 1, 2, or 3 independently selected Group C substituents;

wherein each C(O)O(aryl), $OS(O)_2$aryl, $OS(O)_2$heteroaryl, O(aryl), O(heteroaryl), S(aryl), S(heteroaryl), S(O)aryl, S(O)heteroaryl, $S(O)_2$aryl, $S(O)_2$heteroaryl, non-aromatic heterocyclyl, aryl, and heteroaryl is optionally and independently substituted with 1 or more substituents independently selected from the group consisting of halogen, CN, $NO_2$, alkyl, alkenyl, alkynyl, acyl, $C(O)NH_2$, C(O)OH, C(O)O(alkyl), $NH_2$, OH, O(alkyl), O(aryl), SH, S(alkyl), $S(O)_2$alkyl, cycloalkyl, non-aromatic heterocyclyl, aryl, and heteroaryl;

wherein each alkyl substituent is optionally and independently substituted with 1, 2, or 3 independently selected Group D substituents;

wherein each O(alkyl) substituent is optionally and independently substituted with 1, 2, or 3 independently selected Group A substituents;

wherein each O(aryl) substituent and aryl substituent is optionally and independently substituted with 1, 2, or 3 independently selected Group B substituents; and wherein each non-aromatic heterocyclyl substituent and heteroaryl substituent is optionally and independently substituted with 1, 2, or 3 independently selected Group C substituents; and wherein each $C(O)NH_2$, $NH_2$, and $S(O)_2NH_2$ is optionally and independently substituted with 1 or 2 substituents independently selected from the group consisting of alkyl, alkenyl, alkynyl, acyl, C(O)O(alkyl), C(O)O(alkenyl), C(O)O(alkynyl), $S(O)_2$alkyl, $S(O)_2$alkenyl, $S(O)_2$alkynyl, $S(O)_2$aryl, $S(O)_2$heteroaryl, cycloalkyl, cycloalkenyl, aryl, and heteroaryl;

each Group A substituent is independently halogen or phenyl, wherein each phenyl is optionally and independently substituted with 1, 2, or 3 independently selected Group B substituents;

each Group B substituent is independently halogen, CN, $NO_2$, alkyl, or O(alkyl);

each Group C substituent is independently halogen or alkyl; and each Group D substituent is independently halogen or O(alkyl).

2. The compound of claim 1, or a pharmaceutically acceptable salt thereof, wherein each $R^2$ is independently H, halogen, CN, $NO_2$, =O, alkyl, alkenyl, alkynyl, acyl, C(O)OH, C(O)O(alkyl), C(O)O(alkenyl), C(O)O(alkynyl), C(O)O(aryl), $NH_2$, OH, O(alkyl), O(alkenyl), O(alkynyl), $OS(O)_2$alkyl, $OS(O)_2$cycloalkyl, $OS(O)_2$cycloalkenyl, $OS(O)_2$aryl, $OS(O)_2$heteroaryl, O(cycloalkyl), O(cycloalkenyl), O(aryl), O(heteroaryl), SH, S(alkyl), S(alkenyl), S(alkynyl), S(cycloalkyl), S(cycloalkenyl), S(aryl), S(heteroaryl), S(O)alkyl, S(O)cycloalkyl, S(O)cycloalkenyl, S(O)aryl, S(O)heteroaryl, $S(O)_2$alkyl, $S(O)_2NH_2$, $S(O)_2$cycloalkyl, $S(O)_2$cycloalkenyl, $S(O)_2$aryl, $S(O)_2$heteroaryl, cycloalkyl, cycloalkenyl, non-aromatic heterocyclyl, aryl, or heteroaryl;

wherein each alkyl, alkenyl, alkynyl, C(O)O(alkyl), C(O)O(alkenyl), C(O)O(alkynyl), C(O)O(aryl), $NH_2$, O(alkyl), O(alkenyl), O(alkynyl), $OS(O)_2$alkyl, $OS(O)_2$cycloalkyl, $OS(O)_2$cycloalkenyl, $OS(O)_2$aryl, $OS(O)_2$heteroaryl, O(cycloalkyl), O(cycloalkenyl), O(aryl), O(heteroaryl), S(alkyl), S(alkenyl), S(alkynyl), S(cycloalkyl), S(cycloalkenyl), S(aryl), S(heteroaryl), S(O)alkyl, S(O)cycloalkyl, S(O)cycloalkenyl, S(O)aryl, S(O)heteroaryl, $S(O)_2$alkyl, $S(O)_2NH_2$, $S(O)_2$cycloalkyl, $S(O)_2$cycloalkenyl, $S(O)_2$aryl, $S(O)_2$heteroaryl, cycloalkyl, cycloalkenyl, non-aromatic heterocyclyl, aryl, or heteroaryl is unsubstituted.

3. The compound of claim 1, or a pharmaceutically acceptable salt thereof, wherein each $R^2$ is independently H, halogen, =O, $C_1$-$C_6$ alkyl, acyl, C(O)OH, C(O)O(alkyl), $NH_2$, OH, O($C_1$-$C_6$ alkyl), cycloalkyl, non-aromatic heterocyclyl, aryl, or heteroaryl, wherein each $C_1$-$C_6$ alkyl, C(O)O(alkyl), $NH_2$, O($C_1$-$C_6$ alkyl), cycloalkyl, non-aromatic heterocyclyl, aryl, or heteroaryl is optionally substituted.

4. The compound of claim 1, or a pharmaceutically acceptable salt thereof, wherein each $R^2$ is independently H, halogen, =O, $C_1$-$C_6$ alkyl, acyl, C(O)OH, C(O)O(alkyl), $NH_2$, OH, O($C_1$-$C_6$ alkyl), cycloalkyl, non-aromatic heterocyclyl, aryl, or heteroaryl, wherein each $C_1$-$C_6$ alkyl, C(O)O(alkyl), $NH_2$, O($C_1$-$C_6$ alkyl), cycloalkyl, non-aromatic heterocyclyl, aryl, or heteroaryl is unsubstituted.

5. The compound of claim 1, or a pharmaceutically acceptable salt thereof, wherein Z is $Z^1$.

6. The compound of claim 5, or a pharmaceutically acceptable salt thereof, wherein $A^{14}$ is —$NR^2$—.

7. The compound of claim 6, or a pharmaceutically acceptable salt thereof, wherein $R^2$ in $A^{14}$ is optionally substituted $C_1$-$C_6$ alkyl.

8. The compound of claim 5, or a pharmaceutically acceptable salt thereof, wherein $A^{15}$ is —C(O)—.

9. The compound of claim 5, or a pharmaceutically acceptable salt thereof, wherein:
$A^{14}$ is —$NR^2$—;
$R^2$ in $A^{14}$ is optionally substituted $C_1$-$C_6$ alkyl; and
$A^{15}$ is —C(O)—.

10. The compound of claim 9, or a pharmaceutically acceptable salt thereof, wherein:
$A^{13}$ is $CR^2$;
$A^{16}$ is $CR^2$; and
$A^{17}$ is $CR^2$.

11. The compound of claim 1, or a pharmaceutically acceptable salt thereof, wherein:
Z is $Z^1$;
$A^{14}$ is —$NR^2$—; and
$A^{15}$ is —C(O)—.

12. The compound of claim 11, or a pharmaceutically acceptable salt thereof, wherein:
$A^{13}$ is $CR^2$;
$A^{16}$ is $CR^2$; and
$A^{17}$ is $CR^2$.

13. The compound of claim 1, or a pharmaceutically acceptable salt thereof, wherein Z is $Z^2$.

14. The compound of claim 13, or a pharmaceutically acceptable salt thereof, wherein:
$A^{18}$ is $CR^2$;
$A^{19}$ is C;
$A^{23}$ is C;
$A^{24}$ is $CR^2$;
$A^{25}$ is $CR^2$; and
$A^{26}$ is C.

15. The compound of claim 14, or a pharmaceutically acceptable salt thereof, wherein:
$A^{20}$ is N;
$A^{21}$ is $CR^2$; and
$A^{22}$ is —$NR^2$— or —O—.

16. The compound of claim 14, or a pharmaceutically acceptable salt thereof, wherein:
$A^{20}$ is —$C(R^2)_2$—;
$A^{21}$ is —O—; and
$A^{22}$ is —$C(R^2)_2$—.

17. The compound of claim 1, or a pharmaceutically acceptable salt thereof, wherein:
(i) Z is $Z^2$;
 $A^{21}$ is —O—; and
 $A^{26}$ is C; or
(ii) Z is $Z^2$;
 $A^{20}$ is N;
 $A^{22}$ is —$NR^2$— or —O—; and
 $A^{26}$ is C.

18. The compound of claim 17, or a pharmaceutically acceptable salt thereof, wherein:
Z is $Z^2$;
$A^{21}$ is —O—; and
$A^{26}$ is C.

19. The compound of claim 1, or a pharmaceutically acceptable salt thereof, wherein:
(i) $A^{13}$ is $CR^2$;
 $A^{14}$ is —$NR^2$—;
 $A^{15}$ is —C(O)—;
 $A^{16}$ is $CR^2$;
 $A^{17}$ is $CR^2$;
 $A^{18}$ is $CR^2$;
 $A^{19}$ is C;
 $A^{20}$ is —$C(R^2)_2$—;
 $A^{21}$ is —O—;
 $A^{22}$ is —$C(R^2)_2$—;
 $A^{23}$ is C;
 $A^{24}$ is $CR^2$;
 $A^{25}$ is $CR^2$;
 $A^{26}$ is C; and
  each $R^2$ is independently H, halogen, =O, $C_1$-$C_6$ alkyl, acyl, C(O)OH, C(O)O(alkyl), $NH_2$, OH, O($C_1$-$C_6$ alkyl), cycloalkyl, non-aromatic heterocyclyl, aryl, or heteroaryl, wherein each $C_1$-$C_6$ alkyl, C(O)O(alkyl), $NH_2$, O($C_1$-$C_6$ alkyl), cycloalkyl, non-aromatic heterocyclyl, aryl, and heteroaryl is unsubstituted; or
(ii) $A^{13}$ is $CR^2$;
 $A^{14}$ is —$NR^2$—;
 $A^{15}$ is —C(O)—;
 $A^{16}$ is $CR^2$;
 $A^{17}$ is $CR^2$;
 $A^{18}$ is $CR^2$;
 $A^{19}$ is C;
 $A^{20}$ is N;
 $A^{21}$ is $CR^2$;
 $A^{22}$ is —$NR^2$— or —O—;
 $A^{23}$ is C;
 $A^{24}$ is $CR^2$;
 $A^{25}$ is $CR^2$;
 $A^{26}$ is C; and
  each $R^2$ is independently H, halogen, =O, $C_1$-$C_6$ alkyl, acyl, C(O)OH, C(O)O(alkyl), $NH_2$, OH, O($C_1$-$C_6$ alkyl), cycloalkyl, non-aromatic heterocyclyl, aryl, or heteroaryl, wherein each $C_1$-$C_6$ alkyl, C(O)O(alkyl), $NH_2$, O($C_1$-$C_6$ alkyl), cycloalkyl, non-aromatic heterocyclyl, aryl, and heteroaryl is unsubstituted.

20. The compound of claim 19, or a pharmaceutically acceptable salt thereof, wherein each $R^2$, except for the $R^2$ of $A^{14}$, is independently H.

21. The compound of claim 1, wherein the compound is selected from the group consisting of:

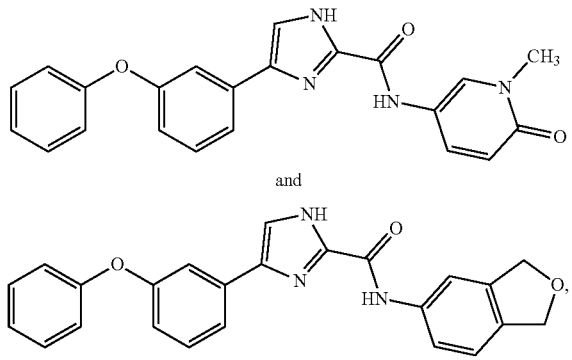

or a pharmaceutically acceptable salt thereof.

22. A pharmaceutical composition comprising a pharmaceutically acceptable diluent or carrier and a compound of claim 1, or a pharmaceutically acceptable salt thereof.

23. A method for treating a condition in an animal in need thereof, wherein the method comprises administering to the animal an effective amount of a compound of claim 1, or a pharmaceutically acceptable salt thereof;
  wherein the condition is selected from the group consisting of arthritis, diabetes, and inflammatory bowel disease.

24. The method of claim 23, wherein the condition is arthritis.

25. The method of claim 24, wherein the arthritis is psoriatic arthritis or rheumatoid arthritis.

26. The method of claim 23, wherein the condition is diabetes.

27. The method of claim 26, wherein the diabetes is selected from the group consisting of atherosclerosis associated with diabetes, deep vein thrombosis associated with diabetes, diabetic nephropathy, diabetic neuropathy, and diabetic retinopathy.

28. The method of claim 23, wherein the condition is inflammatory bowel disease.

29. The method of claim 28, wherein the inflammatory bowel disease is Crohn's disease.

30. The method of claim 28, wherein the inflammatory bowel disease is ulcerative colitis.

31. The method of claim 23, wherein the compound is selected from the group consisting of:

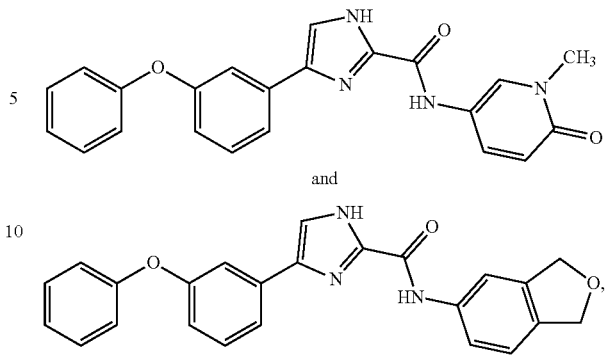

or a pharmaceutically acceptable salt thereof.